(12) United States Patent
Hamilton et al.

(10) Patent No.: US 12,145,990 B2
(45) Date of Patent: **\*Nov. 19, 2024**

(54) T CELL MODIFICATION AND USE THEREOF

(71) Applicant: ADAPTIMMUNE LIMITED, Oxfordshire (GB)

(72) Inventors: Garth Hamilton, Abingdon (GB); Jonathan Silk, Abingdon (GB); Claire Gueguen, Abingdon (GB)

(73) Assignee: ADAPTIMMUNE LIMITED, Abingdon (GB)

( * ) Notice: Subject to any disclaimer, the term of this patent is extended or adjusted under 35 U.S.C. 154(b) by 397 days.

This patent is subject to a terminal disclaimer.

(21) Appl. No.: 17/468,225

(22) Filed: Sep. 7, 2021

(65) Prior Publication Data
US 2022/0064305 A1 Mar. 3, 2022

Related U.S. Application Data

(63) Continuation of application No. 15/998,475, filed on Aug. 15, 2018, now Pat. No. 11,111,301.

(30) Foreign Application Priority Data

Aug. 15, 2017 (GB) ..................................... 1713078

(51) Int. Cl.
| | |
|---|---|
| *C07K 16/28* | (2006.01) |
| *A61K 39/00* | (2006.01) |
| *A61P 35/00* | (2006.01) |
| *C07K 14/47* | (2006.01) |
| *C07K 14/54* | (2006.01) |
| *C07K 14/725* | (2006.01) |
| *C07K 16/24* | (2006.01) |
| *C07K 16/30* | (2006.01) |
| *C12N 5/0783* | (2010.01) |

(52) U.S. Cl.
CPC ...... *C07K 16/2833* (2013.01); *A61K 39/0011* (2013.01); *A61P 35/00* (2018.01); *C07K 14/4748* (2013.01); *C07K 14/5418* (2013.01); *C07K 14/7051* (2013.01); *C07K 16/244* (2013.01); *C07K 16/30* (2013.01); *C12N 5/0636* (2013.01); *A61K 2039/5156* (2013.01); *A61K 2039/5158* (2013.01); *C07K 2317/622* (2013.01); *C07K 2319/03* (2013.01); *C07K 2319/33* (2013.01)

(58) Field of Classification Search
CPC ................................................ C07K 16/2833
See application file for complete search history.

(56) References Cited

U.S. PATENT DOCUMENTS

| | | | |
|---|---|---|---|
| 5,837,510 A | 11/1998 | Goldsmith et al. | |
| 11,111,301 B2 | 9/2021 | Hamilton et al. | |
| 2012/0071859 A1 | 3/2012 | Morgan et al. | |
| 2019/0038671 A1 | 2/2019 | Fan et al. | |
| 2019/0100592 A1 | 4/2019 | Hamilton et al. | |
| 2020/0010803 A1 | 1/2020 | Adusumilli | |
| 2020/0255505 A1 | 8/2020 | Staley et al. | |
| 2021/0032661 A1 | 2/2021 | Powell et al. | |
| 2021/0252059 A1 | 8/2021 | Pu et al. | |

FOREIGN PATENT DOCUMENTS

| | | |
|---|---|---|
| CN | 106086073 | 11/2016 |
| CN | 107207615 | 9/2017 |
| CN | 109328196 | 2/2019 |
| CN | 110325633 | 10/2019 |
| CN | 112175998 | 1/2021 |
| CN | 112210539 | 1/2021 |
| CN | 112210540 | 1/2021 |
| CN | 112226462 | 1/2021 |
| CN | 112980886 | 6/2021 |
| CN | 113164519 | 7/2021 |
| CN | 113677352 | 11/2021 |
| CN | 113924103 | 1/2022 |
| CN | 116286665 | 6/2023 |
| EP | 1143013 A1 | 10/2001 |
| JP | H10179181 A | 7/1998 |
| WO | WO 2013126726 | 8/2013 |

(Continued)

OTHER PUBLICATIONS

Markley et al., "IL-7 and IL-21 are superior to IL-2 and IL-15 in promoting human T cell-mediated rejection of systemic lymphoma in immunodeficient mice," Blood, Apr. 29, 2010, vol. 115, issue 17, pp. 3508-3519.

Zhang et al., "Improving adoptive T cell therapy by targeting and controlling IL-12 expression to the tumor environment," Molecular Therapy, vol. 19, No. 4, pp. 751-759, Apr. 2011.

Overwijk et al., "Tumor regression and autoimmunity after reversal of a functionally tolerant state of self-reactive CD8+ T cells," The Journal of Experimental Medicine, vol. 198, No. 4, pp. 569-580, Aug. 18, 2003.

(Continued)

*Primary Examiner* — Anoop K Singh
*Assistant Examiner* — David A Montanari
(74) *Attorney, Agent, or Firm* — Sheppard Mullin Richter & Hampton LLP

(57) ABSTRACT

This invention relates to modified T cells that inducibly express a bioactive molecule, such as IL-7, and constitutively expresses an antigen receptor, such as a T cell receptor or chimeric antigen receptor that binds to a tumour antigen. The modified T cells may comprise a nucleic acid construct that comprises a first nucleotide sequence encoding the bioactive molecule, a second nucleotide sequence encoding the antigen receptor; an inducible promoter operably linked to the first nucleotide sequence and a constitutive promoter operably linked to the second nucleotide. Nucleic acid constructs and vectors are provided, as well as T cells comprising such constructs and vectors and therapeutic methods and uses thereof.

19 Claims, 17 Drawing Sheets

Specification includes a Sequence Listing.

(56) References Cited

FOREIGN PATENT DOCUMENTS

| WO | 2016073755 A2 | 5/2016 |
|---|---|---|
| WO | 2016126608 | 8/2016 |
| WO | WO 2017186121 | 11/2017 |
| WO | 2018050225 | 3/2018 |
| WO | WO 2019034703 | 2/2019 |
| WO | WO 2021028359 | 2/2021 |
| WO | WO 2021109977 | 6/2021 |
| WO | WO 2021244654 | 6/2021 |
| WO | WO 2021259334 | 12/2021 |

OTHER PUBLICATIONS

Kouskoff et al., "Cassette vectors directing expression of T cell receptor genes in transgenic mice," Journal of Immunological Methods, vol. 180, pp. 273-280, 1995.

Chmielewski et al., "IL-12 Release by Engineered T Cells Expressing Chimeric Antigen Receptors Can Effectively Muster an Antigen-Independent Macrophage Response on Tumor Cells That Have Shut Down Tumor Antigen Expression", Cancer Research, 71 (17), 5697-5706 (2011).

Chmielewski et al.,"Of CARS and TRUCKs: chimeric antigen receptor {CAR) T cells engineered with an inducible cytokine to modulate the tumor stroma" Immunological Reviews, 257 (1), 83-90 (2014).

Pellgrini et al., "Adjuvant IL-7 antagonizes multiple cellular and molecular inhibitory networks to enhance Immunotherapies", Nature Medicine, 15 (5), 528-536 (2009).

Partial Search Report for International Application No. PCT/EP2018/072148, dated Dec. 17, 2018.

Choo et al., 2016, PLOS One, vol. 119(9), pp. 1-15 (Year: 2016).

Dolgin E., 2017, Cancer Discovery, vol. 7, pp. 926 (Year: 2017).

Engelhardt et al. (2006, J. Neural. Transm., vol. 113, pp. 477-485) (Year: 2006).

Kayser et al. (2015, OncoImmunology, vol. 4(5), pp. 1-13) (Year: 2015).

Shum et al. (epub Aug. 22, 2017, Cancer Discovery, pp. 1-10 (Year: 2017).

Singh et al., 2016, Oncoimmunology, vol. 5(1), pp. 1-13 (Year: 2016).

Xie et al. (2010, J. Experimental Med., vol. 207(3), pp. 651-667) (Year: 2010).

R1_"Basics of Medicinal Microorganisms" Jan. 31, 2017 Editor-in-Chief Chen Mingqi, China Medical Science and Technology Press p. 187 "Cytokines" 1-39.

SEQUENCE LISTING

<160> NUMBER OF SEQ ID NOS: 24

<210> SEQ ID NO 1
<211> LENGTH: 1050
<212> TYPE: DNA
<213> ORGANISM: Artificial Sequence
<220> FEATURE:
<223> OTHER INFORMATION: NFAT IL-7 inducible cassette

<400> SEQUENCE: 1

```
accggttcaa ttgccgaccc ctcccccaa cttctcgggg actgtgggcg atgtgcgctc       60
tgcccactga cgggcaccgg agcctcacga tgcatgatat cggcctaact ggccggtacc      120
tgagctcgct agcggaggaa aaactgtttc atacagaagg cgtggaggaa aaactgtttc      180
atacagaagg cgtggaggaa aaactgtttc atacagaagg cgtgacgtct aggcgtgtac      240
ggtgggaggc ctatataagc agagctcgtt tagtgaaccg tcagatcgcc tggagacgcc      300
atccacgctg ttttgacctc catagaagac accgggaccg atccagcctc tcgacattcg      360
ttggatccat atggccgcca ccatgttcca tgtttctttt aggtatatct ttggacttcc      420
tcccctgatc cttgttctgt tgccagtagc atcatctgat tgtgatattg aaggtaaaga      480
tggcaaacaa tatgagagtg ttctaatggt cagcatcgat caattattgg acagcatgaa      540
agaaattggt agcaattgcc tgaataatga atttaacttt tttaaaagac atatctgtga      600
tgctaataag gaaggtatgt ttttattccg tgctgctcgc aagttgaggc aatttcttaa      660
aatgaatagc actggtgatt tgatctcca cttattaaaa gtttcagaag cacaacaat       720
actgttgaac tgcactggcc aggttaaagg aagaaaacca gctgccctgg gtgaagccca      780
accaacaaag agtttggaag aaaataaatc tttaaaggaa cagaaaaaac tgaatgactt      840
gtgtttccta aagagactat tacaagagat aaaaacttgt tggaataaaa ttttgatggg      900
cactaaagaa cactgactcg agaacttgtt tattgcagct tataatggtt acaaataaag      960
caatagcatc acaaatttca caaataaagc atttttttca ctgcattcta gttgtggttt     1020
gtccaaactc atcaatgtat cttaacgcgt                                      1050
```

<210> SEQ ID NO 2
<211> LENGTH: 534
<212> TYPE: DNA
<213> ORGANISM: Artificial Sequence
<220> FEATURE:
<223> OTHER INFORMATION: codon optimised IL-7

<400> SEQUENCE: 2

```
atgttccatg tttctttag gtatatcttt ggacttcctc ccctgatcct tgttctgttg       60
```

```
ccagtagcat catctgattg tgatattgaa ggtaaagatg gcaaacaata tgagagtgtt      120
ctaatggtca gcatcgatca attattggac agcatgaaag aaattggtag caattgcctg      180
aataatgaat ttaactttt taaaagacat atctgtgatg ctaataagga aggtatgttt      240
ttattccgtg ctgctcgcaa gttgaggcaa tttcttaaaa tgaatagcac tggtgatttt      300
gatctccact tattaaaagt ttcagaaggc acaacaatac tgttgaactg cactggccag      360
gttaaaggaa gaaaaccagc tgccctgggt gaagcccaac caacaaagag tttggaagaa      420
aataaatctt taaaggaaca gaaaaaactg aatgacttgt gtttcctaaa gagactatta      480
caagagataa aaacttgttg gaataaaatt ttgatgggca ctaaagaaca ctga            534
```

<210> SEQ ID NO 3
<211> LENGTH: 177
<212> TYPE: PRT
<213> ORGANISM: Artificial Sequence
<220> FEATURE:
<223> OTHER INFORMATION: Codon opotimised IL-7

<400> SEQUENCE: 3

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 4
<211> LENGTH: 1854
<212> TYPE: DNA
<213> ORGANISM: Artificial Sequence
<220> FEATURE:
<223> OTHER INFORMATION: sequence between NheI and SalI sites

<400> SEQUENCE: 4

```
atggagaccc tgctgggcct gctgatcctg tggctgcagc tccagtgggt gtccagcaag      60
caggaggtga cccagatccc tgccgccctg agcgtgcccg agggcgagaa cctggtgctg      120
aactgcagct tcaccgactc cgccatctac aacctgcagt ggttccggca ggaccccggc      180
aagggcctga ccagcctgct gctgatccag agcagccagc gggagcagac cagcggacgg      240
```

-continued

```
ctgaacgcca gcctggacaa gagcagcggc cggagcaccc tgtacatcgc cgccagccag      300
cccggcgaca gcgccaccta cctgtgcgct gtgcggcctc tgtacggcgg cagctacatc      360
cccaccttcg gcagaggcac cagcctgatc gtgcacccct acatccagaa ccccgacccc      420
gccgtgtacc agctgcggga cagcaagagc agcgacaagt ctgtgtgcct gttcaccgac      480
ttcgacagcc agaccaatgt gagccagagc aaggacagcg acgtgtacat caccgacaag      540
accgtgctgg acatgcggag catggacttc aagagcaaca cgccgtggc ctggagcaac       600 aagagcgact cgcctgcgc caacgccttc aacaacagca ttatccccga ggacaccttc       660
ttccccagcc ccgagagcag ctgcgacgtg aaactggtgg agaagagctt cgagaccgac      720
accaacctga acttccagaa cctgagcgtg atcggcttca atcctgct gctgaaggtg        780 gccggattca acctgctgat gaccctgcgg ctgtggagca cggctcccg ggccaagaga       840 agcggatccg gcgccaccaa cttcagcctg ctgaagcagg ccggagacgt ggaagaaaac     900
cctggcccta ggatgagcat cggcctgctg tgctgcgccg ccctgagcct gctgtgggca     960
ggacccgtga acgccggagt gacccagacc cccaagttcc aggtgctgaa aaccggccag    1020
agcatgaccc tgcagtgcgc ccaggacatg aaccacgagt acatgagctg gtatcggcag    1080
gaccccggca tgggcctgcg gctgatccac tactctgtgg agccggaat caccgaccag     1140 ggcgaggtgc ccaacggcta caatgtgagc cggagcacca ccgaggactt cccctgcgg     1200 ctgctgagcg ctgccccag ccagaccagc gtgtacttct cgccagcag ctatgtgggc      1260 aacaccggcg agctgttctt cggcgagggc tccaggctga ccgtgctgga ggacctgaag    1320
aacgtgttcc ccccgaggt ggccgtgttc gagcccagcg aggccgagat cagccacacc     1380
cagaaggcca cactggtgtg tctggccacc ggcttctacc ccgaccacgt ggagctgtcc    1440
tggtgggtga acggcaagga ggtgcacagc ggcgtgtcta ccgaccccca gcccctgaag    1500
gagcagcccg ccctgaacga cagccggtac tgcctgtcct ccagactgag agtgagcgcc   1560
accttctggc agaacccccg gaaccacttc cggtgccagg tgcagttcta cggcctgagc    1620
gagaacgacg agtggaccca ggaccgggcc aagcccgtga cccagattgt gagcgccgag   1680
gcctggggca gggccgactg cggcttcacc agcgagagct accagcaggg cgtgctgagc    1740
gccaccatcc tgtacgagat cctgctgggc aaggccaccc tgtacgccgt gctggtgtct   1800
gccctggtgc tgatggctat ggtgaagcgg aaggacagcc ggggctaagt cgac         1854
```

<210> SEQ ID NO 5
<211> LENGTH: 616
<212> TYPE: PRT
<213> ORGANISM: Artificial Sequence
<220> FEATURE:
<223> OTHER INFORMATION: TCR1

<400> SEQUENCE: 5

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

```
Leu Asn Ala Ser Leu Asp Lys Ser Ser Gly Arg Ser Thr Leu Tyr Ile
            85                  90                  95

Ala Ala Ser Gln Pro Gly Asp Ser Ala Thr Tyr Leu Cys Ala Val Arg
            100                 105                 110

Pro Leu Tyr Gly Gly Ser Tyr Ile Pro Thr Phe Gly Arg Gly Thr Ser
            115                 120                 125

Leu Ile Val His Pro Tyr Ile Gln Asn Pro Asp Pro Ala Val Tyr Gln
            130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
            165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
            245                 250                 255

Leu Leu Lys Val Ala Gly Phe Asn Leu Leu Met Thr Leu Arg Leu Trp
            260                 265                 270

Ser Ser Gly Ser Arg Ala Lys Arg Ser Gly Ser Gly Ala Thr Asn Phe
            275                 280                 285

Ser Leu Leu Lys Gln Ala Gly Asp Val Glu Glu Asn Pro Gly Pro Arg
            290                 295                 300

Met Ser Ile Gly Leu Leu Cys Cys Ala Ala Leu Ser Leu Leu Trp Ala
305                 310                 315                 320

Gly Pro Val Asn Ala Gly Val Thr Gln Thr Pro Lys Phe Gln Val Leu
            325                 330                 335

Lys Thr Gly Gln Ser Met Thr Leu Gln Cys Ala Gln Asp Met Asn His
            340                 345                 350

Glu Tyr Met Ser Trp Tyr Arg Gln Asp Pro Gly Met Gly Leu Arg Leu
            355                 360                 365

Ile His Tyr Ser Val Gly Ala Gly Ile Thr Asp Gln Gly Glu Val Pro
            370                 375                 380

Asn Gly Tyr Asn Val Ser Arg Ser Thr Thr Glu Asp Phe Pro Leu Arg
385                 390                 395                 400

Leu Leu Ser Ala Ala Pro Ser Gln Thr Ser Val Tyr Phe Cys Ala Ser
            405                 410                 415

Ser Tyr Val Gly Asn Thr Gly Glu Leu Phe Phe Gly Glu Gly Ser Arg
            420                 425                 430

Leu Thr Val Leu Glu Asp Leu Lys Asn Val Phe Pro Pro Glu Val Ala
            435                 440                 445

Val Phe Glu Pro Ser Glu Ala Glu Ile Ser His Thr Gln Lys Ala Thr
450                 455                 460

Leu Val Cys Leu Ala Thr Gly Phe Tyr Pro Asp His Val Glu Leu Ser
465                 470                 475                 480

Trp Trp Val Asn Gly Lys Glu Val His Ser Gly Val Ser Thr Asp Pro
            485                 490                 495
```

```
Gln Pro Leu Lys Glu Gln Pro Ala Leu Asn Asp Ser Arg Tyr Cys Leu
            500                 505                 510

Ser Ser Arg Leu Arg Val Ser Ala Thr Phe Trp Gln Asn Pro Arg Asn
        515                 520                 525

His Phe Arg Cys Gln Val Gln Phe Tyr Gly Leu Ser Glu Asn Asp Glu
    530                 535                 540

Trp Thr Gln Asp Arg Ala Lys Pro Val Thr Gln Ile Val Ser Ala Glu
545                 550                 555                 560

Ala Trp Gly Arg Ala Asp Cys Gly Phe Thr Ser Glu Ser Tyr Gln Gln
                565                 570                 575

Gly Val Leu Ser Ala Thr Ile Leu Tyr Glu Ile Leu Leu Gly Lys Ala
                580                 585                 590

Thr Leu Tyr Ala Val Leu Val Ser Ala Leu Val Leu Met Ala Met Val
            595                 600                 605

Lys Arg Lys Asp Ser Arg Gly Val
            610                 615

<210> SEQ ID NO 6
<211> LENGTH: 615
<212> TYPE: PRT
<213> ORGANISM: Artificial Sequence
<220> FEATURE:
<223> OTHER INFORMATION: TCR1 CDS

<400> SEQUENCE: 6

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Leu Tyr Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240
```

```
Thr Asn Leu Asn Phe Gln Asn Leu Ser Val Ile Gly Phe Arg Ile Leu
                245                 250                 255

Leu Leu Lys Val Ala Gly Phe Asn Leu Met Thr Leu Arg Leu Trp
        260                 265                 270

Ser Ser Gly Ser Arg Ala Lys Arg Ser Gly Ser Gly Ala Thr Asn Phe
            275                 280                 285

Ser Leu Leu Lys Gln Ala Gly Asp Val Glu Asn Pro Gly Pro Arg
        290                 295                 300

Met Ser Ile Gly Leu Leu Cys Cys Ala Ala Leu Ser Leu Leu Trp Ala
305                 310                 315                 320

Gly Pro Val Asn Ala Gly Val Thr Gln Thr Pro Lys Phe Gln Val Leu
                325                 330                 335

Lys Thr Gly Gln Ser Met Thr Leu Gln Cys Ala Gln Asp Met Asn His
            340                 345                 350

Glu Tyr Met Ser Trp Tyr Arg Gln Asp Pro Gly Met Gly Leu Arg Leu
        355                 360                 365

Ile His Tyr Ser Val Gly Ala Gly Ile Thr Asp Gln Gly Glu Val Pro
    370                 375                 380

Asn Gly Tyr Asn Val Ser Arg Ser Thr Thr Glu Asp Phe Pro Leu Arg
385                 390                 395                 400

Leu Leu Ser Ala Ala Pro Ser Gln Thr Ser Val Tyr Phe Cys Ala Ser
                405                 410                 415

Ser Tyr Val Gly Asn Thr Gly Glu Leu Phe Phe Gly Glu Gly Ser Arg
            420                 425                 430

Leu Thr Val Leu Glu Asp Leu Lys Asn Val Phe Pro Pro Glu Val Ala
        435                 440                 445

Val Phe Glu Pro Ser Glu Ala Glu Ile Ser His Thr Gln Lys Ala Thr
    450                 455                 460

Leu Val Cys Leu Ala Thr Gly Phe Tyr Pro Asp His Val Glu Leu Ser
465                 470                 475                 480

Trp Trp Val Asn Gly Lys Glu Val His Ser Gly Val Ser Thr Asp Pro
                485                 490                 495

Gln Pro Leu Lys Glu Gln Pro Ala Leu Asn Asp Ser Arg Tyr Cys Leu
            500                 505                 510

Ser Ser Arg Leu Arg Val Ser Ala Thr Phe Trp Gln Asn Pro Arg Asn
        515                 520                 525

His Phe Arg Cys Gln Val Gln Phe Tyr Gly Leu Ser Glu Asn Asp Glu
    530                 535                 540

Trp Thr Gln Asp Arg Ala Lys Pro Val Thr Gln Ile Val Ser Ala Glu
545                 550                 555                 560

Ala Trp Gly Arg Ala Asp Cys Gly Phe Thr Ser Glu Ser Tyr Gln Gln
                565                 570                 575

Gly Val Leu Ser Ala Thr Ile Leu Tyr Glu Ile Leu Leu Gly Lys Ala
            580                 585                 590

Thr Leu Tyr Ala Val Leu Val Ser Ala Leu Val Leu Met Ala Met Val
        595                 600                 605

Lys Arg Lys Asp Ser Arg Gly
610                 615

<210> SEQ ID NO 7
<211> LENGTH: 4012
<212> TYPE: DNA
<213> ORGANISM: Artificial Sequence
<220> FEATURE:
<223> OTHER INFORMATION: sequence spanning hte region between the MluI
``` and SalI restriction sites.

<400> SEQUENCE: 7

| | | | | | |
|---|---|---|---|---|---|
| acgcgttaag | atacattgat | gagtttggac | aaaccacaac | tagaatgcag | tgaaaaaaat | 60 |
| gctttatttg | tgaaatttgt | gatgctattg | ctttatttgt | aaccattata | agctgcaata | 120 |
| aacaagttct | cgagtcagtg | ctctttggtg | cccatcagga | tcttgttcca | gcaggtcttg | 180 |
| atttcctgca | gcagccgctt | caggaagcac | aggtcgttca | gtttcttctg | ctctttcagg | 240 |
| gacttgttct | cttccaggct | cttggtaggc | tgggcttctc | ccagggcggc | aggctttctg | 300 |
| cccttcactt | ggccggtgca | attcagcagg | atggtggtgc | cctcggacac | tttcagcaga | 360 |
| tgcaggtcga | agtcgccggt | gctgttcatc | ttcaggaact | gccgcagctt | tctggcggct | 420 |
| ctgaacagga | acatgccttc | tttgttggcg | tcgcagatgt | gccgcttgaa | gaagttgaac | 480 |
| tcgttgttca | ggcagttgct | gccgatttcc | ttcatgctgt | ccagcagctg | gtcgatggac | 540 |
| accatcagca | cgctctcgta | ctgcttgccg | tccttgccct | cgatgtcgca | gtcgctgctg | 600 |
| gccacaggca | gcagcaccag | gatcagggggg | ggcaggccga | agatgtaccg | gaaggacacg | 660 |
| tggaacatgg | tggcggccat | atggatccaa | cgaatgtcga | gaggctggat | cggtcccggt | 720 |
| gtcttctatg | gaggtcaaaa | cagcgtggat | ggcgtctcca | ggcgatctga | cggttcacta | 780 |
| aacgagctct | gcttatatag | gcctcccacc | gtacacgcct | agacgtcacg | ccttctgtat | 840 |
| gaaacagttt | ttcctccacg | ccttctgtat | gaaacagttt | ttcctccacg | ccttctgtat | 900 |
| gaaacagttt | ttcctccgct | agcgagctca | ggtaccggcc | agttaggccg | atatcatgca | 960 |
| tcgtgaggct | ccggtgcccg | tcagtgggca | gagcgcacat | cgcccacagt | ccccgagaag | 1020 |
| ttggggggag | gggtcggcaa | ttgaaccggt | gcctagagaa | ggtggcgcgg | ggtaaactgg | 1080 |
| gaaagtgatg | tcgtgtactg | gctccgcctt | tttcccgagg | gtgggggaga | accgtatata | 1140 |
| agtgcagtag | tcgccgtgaa | cgttctttttt | cgcaacgggt | ttgccgccag | aacacaggta | 1200 |
| agtgccgtgt | gtggttcccg | cgggcctggc | ctctttacgg | gttatggccc | ttgcgtgcct | 1260 |
| tgaattactt | ccacctggct | gcagtacgtg | attcttgatc | ccgagcttcg | ggttggaagt | 1320 |
| gggtgggaga | gttcgaggcc | ttgcgcttaa | ggagcccctt | cgcctcgtgc | ttgagttgag | 1380 |
| gcctggcctg | ggcgctgggg | ccgccgcgtg | cgaatctggt | ggcaccttcg | cgcctgtctc | 1440 |
| gctgctttcg | ataagtctct | agccatttaa | aatttttgat | gacctgctgc | gacgcttttt | 1500 |
| ttctggcaag | atagtcttgt | aaatgcgggc | caagatctgc | acactggtat | tcggttttt | 1560 |
| ggggccgcgg | gcggcgacgg | ggcccgtgcg | tcccagcgca | catgttcggc | gaggcggggc | 1620 |
| ctgcgagcgc | ggccaccgag | aatcggacgg | gggtagtctc | aagctggccg | gcctgctctg | 1680 |
| gtgcctggcc | tcgcgccgcc | gtgtatcgcc | ccgcccctggg | cggcaaggct | ggcccggtcg | 1740 |
| gcaccagttg | cgtgagcgga | aagatggccg | cttcccggcc | ctgctgcagg | gagctcaaaa | 1800 |
| tggaggacgc | ggcgctcggg | agagcgggcg | ggtgagtcac | ccacacaaag | gaaaagggcc | 1860 |
| tttccgtcct | cagccgtcgc | ttcatgtgac | tccactgagt | accgggcgcc | gtccaggcac | 1920 |
| ctcgattagt | tctcgtgctt | ttggagtacg | tcgtctttag | gttgggggga | ggggttttat | 1980 |
| gcgatggagt | ttccccacac | tgagtgggtg | gagactgaag | ttaggccagc | ttggcacttg | 2040 |
| atgtaattct | ccttggaatt | tgccctttttt | gagtttggat | cttggttcat | tctcaagcct | 2100 |
| cagacagtgg | ttcaaagttt | ttttcttcca | tttcaggtgt | cgtgagctag | ccgccaccat | 2160 |
| ggagaccctg | ctgggcctgc | tgatcctgtg | gctgcagctc | cagtgggtgt | ccagcaagca | 2220 |
| ggaggtgacc | cagatccctg | ccgccctgag | cgtgcccgag | ggcgagaacc | tggtgctgaa | 2280 |

```
ctgcagcttc accgactccg ccatctacaa cctgcagtgg ttccggcagg accccggcaa    2340
gggcctgacc agcctgctgc tgatccgaga cagccagcgg gagcagacca gcggacggct    2400
gaacgccagc ctggacaaga gcagcggccg gagcaccctg tacatcgccg ccagccagcc    2460
cggcgacagc gccacctacc tgtgcgctgt gcggcctctg tacggcggca gctacatccc    2520
caccttcggc agaggcacca gcctgatcgt gcacccctac atccagaacc ccgaccccgc    2580
cgtgtaccag ctgcgggaca gcaagagcag cgacaagtct gtgtgcctgt tcaccgactt    2640
cgacagccag accaatgtga ccagagcaa ggacagcgac gtgtacatca ccgacaagac    2700
cgtgctggac atgcggagca tggacttcaa gagcaacagc gccgtggcct ggagcaacaa    2760
gagcgacttc gcctgcgcca acgccttcaa caacagcatt atccccgagg acaccttctt    2820
ccccagcccc gagagcagct cgacgtgaa actggtggag aagagcttcg agaccgacac    2880
caacctgaac ttccagaacc tgagcgtgat cggcttcaga atcctgctgc tgaaggtggc    2940
cggattcaac ctgctgatga ccctgcggct gtggagcagc ggctcccggg ccaagagaag    3000
cggatccggc gccaccaact tcagcctgct gaagcaggcc ggagacgtgg aagaaaaccc    3060
tggccctagg atgagcatcg gcctgctgtg ctgcgccgcc ctgagcctgc tgtgggcagg    3120
acccgtgaac gccggagtga cccagacccc caagttccag gtgctgaaaa ccggccagag    3180 catgacccctg cagtgcgccc aggacatgaa ccacgagtac atgagctggt atcggcagga    3240
ccccggcatg ggcctgcggc tgatccacta ctctgtggga gccggaatca ccgaccaggg    3300
cgaggtgccc aacggctaca atgtgagccg gagcaccacc gaggacttcc ccctgcggct    3360
gctgagcgct gcccccagcc agaccagcgt gtacttctgc gccagcagct atgtgggcaa    3420
caccggcgag ctgttcttcg gcagggctc caggctgacc gtgctggagg acctgaagaa    3480
cgtgttcccc cccgaggtgg ccgtgttcga gcccagcgag gccgagatca gccacaccca    3540
gaaggccaca ctggtgtgtc tggccaccgg cttctacccc gaccacgtgg agctgtcctg    3600
gtgggtgaac ggcaaggagg tgcacagcgg cgtgtctacc gaccccagc ccctgaagga    3660 gcagcccgcc ctgaacgaca gccggtactg cctgtcctcc agactgagag tgagcgccac    3720
cttctggcag aaccccggga accacttccg gtgccaggtg cagttctacg gcctgagcga    3780
gaacgacgag tggacccagg accgggccaa gcccgtgacc cagattgtga gcgccgaggc    3840
ctggggcagg gccgactgcg gcttcaccag cgagagctac cagcagggcg tgctgagcgc    3900
caccatcctg tacgagatcc tgctgggcaa ggccaccctg tacgccgtgc tggtgtctgc    3960
cctggtgctg atggctatgg tgaagcggaa ggacagccgg ggctaagtcg ac            4012
```

<210> SEQ ID NO 8
<211> LENGTH: 2484
<212> TYPE: DNA
<213> ORGANISM: Artificial Sequence
<220> FEATURE:
<223> OTHER INFORMATION: Consitutive IL-7_T2A_TCR1 covering the region
      between the NheI and SalI restriction sites

<400> SEQUENCE: 8

```
gctagcgccg ccaccatgtt ccacgtgtcc ttccggtaca tcttcggcct gcccccctg      60 atcctggtgc tgctgcctgt ggccagcagc gactgcgaca tcgagggcaa ggacggcaag    120
cagtacgaga gcgtgctgat ggtgtccatc gaccagctgc tggacagcat gaaggaaatc    180
ggcagcaact gcctgaacaa cgagttcaac ttcttcaagc ggcacatctg cgacgccaac    240
aaagaaggca tgttcctgtt cagagccgcc agaaagctgc ggcagttcct gaagatgaac    300
```

```
agcaccggcg acttcgacct gcatctgctg aaagtgtccg agggcaccac catcctgctg    360
aattgcaccg gccaagtgaa gggcagaaag cctgccgccc tgggagaagc ccagcctacc    420
aagagcctgg aagagaacaa gtccctgaaa gagcagaaga aactgaacga cctgtgcttc    480
ctgaagcggc tgctgcagga aatcaagacc tgctggaaca agatcctgat gggcaccaaa    540
gagcacggaa gcagagccaa gagaagcggc tctggcgagg cagaggcag cctgctgaca     600 tgtggcgacg tggaagaaaa ccctggccct atggagaccc tgctgggcct gctgatcctg    660
tggctgcagc tccagtgggt gtccagcaag caggaggtga cccagatccc tgccgccctg    720
agcgtgcccg agggcgagaa cctggtgctg aactgcagct tcaccgactc cgccatctac    780
aacctgcagt ggttccggca ggaccccggc aagggcctga ccagcctgct gctgatccag    840
agcagccagc gggagcagac cagcggacgg ctgaacgcca gcctggacaa gagcagcggc    900
cggagcaccc tgtacatcgc cgccagccag cccggcgaca cgccacccta cctgtgcgct    960
gtgcggcctc tgtacggcgg cagctacatc cccaccttcg gcagaggcac cagcctgatc   1020
gtgcacccct acatccagaa ccccgacccc gccgtgtacc agctgcggga cagcaagagc   1080
agcgacaagt ctgtgtgcct gttcaccgac ttcgacagcc agaccaatgt gagccagagc   1140
aaggacagcg acgtgtacat caccgacaag accgtgctgg acatgcggag catggacttc   1200
aagagcaaca cgccgtggc ctggagcaac aagagcgact cgcctgcgc caacgccttc    1260 aacaacagca ttatccccga ggacaccttc ttccccagcc ccgagagcag ctgcgacgtg   1320
aaactggtgg agaagagctt cgagaccgac accaacctga acttccagaa cctgagcgtg   1380
atcggcttca gaatcctgct gctgaaggtg gccggattca acctgctgat gaccctgcgg   1440
ctgtggagca gcggctcccg ggccaagaga agcggatccg gcgccaccaa cttcagcctg   1500
ctgaagcagg ccggagacgt ggaagaaaac cctggcccta ggatgagcat cggcctgctg   1560
tgctgcgccg ccctgagcct gctgtgggca ggaccgtga acgccggagt gacccagacc   1620
cccaagttcc aggtgctgaa aaccggccag agcatgaccc tgcagtgcgc ccaggacatg   1680
aaccacgagt acatgagctg gtatcggcag gaccccggca tgggcctgcg gctgatccac   1740
tactctgtgg gagccggaat caccgaccag ggcgaggtgc ccaacggcta caatgtgagc   1800
cggagcacca ccgaggactt ccccctgcgg ctgctgagcg ctgccccag ccagaccagc    1860 gtgtacttct gcgccagcag ctatgtgggc aacaccggcg agctgttctt cggcgagggc   1920
tccaggctga ccgtgctgga ggacctgaag aacgtgttcc ccccgaggt ggccgtgttc    1980 gagcccagcg aggccgagat cagccacacc cagaaggcca cactggtgtg tctggccacc   2040
ggcttctacc ccgaccacgt ggagctgtcc tggtgggtga acggcaagga ggtgcacagc   2100
ggcgtgtcta ccgaccccca gccctgaag agcagcccg ccctgaacga cagccggtac     2160
tgcctgtcct ccagactgag agtgagcgcc accttctggc agaaccccg gaaccacttc    2220 cggtgccagg tgcagttcta cggcctgagc gagaacgacg agtggaccca ggaccgggcc   2280
aagcccgtga cccagattgt gagcgccgag gcctggggca gggccgactg cggcttcacc   2340
agcgagagct accagcaggg cgtgctgagc gccaccatcc tgtacgagat cctgctgggc   2400
aaggccaccc tgtacgccgt gctggtgtct gccctggtgc tgatggctat ggtgaagcgg   2460
aaggacagcc ggggctaagt cgac                                          2484
```

<210> SEQ ID NO 9
<211> LENGTH: 820
<212> TYPE: PRT

<213> ORGANISM: Artificial Sequence
<220> FEATURE:
<223> OTHER INFORMATION: Constitutive IL-7_TCR1

<400> SEQUENCE: 9

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His Gly Ser Arg Ala Lys Arg Ser Gly Ser Gly Glu Gly Arg Gly Ser
            180                 185                 190

Leu Leu Thr Cys Gly Asp Val Glu Glu Asn Pro Gly Pro Met Glu Thr
        195                 200                 205

Leu Leu Gly Leu Leu Ile Leu Trp Leu Gln Leu Gln Trp Val Ser Ser
    210                 215                 220

Lys Gln Glu Val Thr Gln Ile Pro Ala Ala Leu Ser Val Pro Glu Gly
225                 230                 235                 240

Glu Asn Leu Val Leu Asn Cys Ser Phe Thr Asp Ser Ala Ile Tyr Asn
                245                 250                 255

Leu Gln Trp Phe Arg Gln Asp Pro Gly Lys Gly Leu Thr Ser Leu Leu
            260                 265                 270

Leu Ile Gln Ser Ser Gln Arg Glu Gln Thr Ser Gly Arg Leu Asn Ala
        275                 280                 285

Ser Leu Asp Lys Ser Ser Gly Arg Ser Thr Leu Tyr Ile Ala Ala Ser
    290                 295                 300

Gln Pro Gly Asp Ser Ala Thr Tyr Leu Cys Ala Val Arg Pro Leu Tyr
305                 310                 315                 320

Gly Gly Ser Tyr Ile Pro Thr Phe Gly Arg Gly Thr Ser Leu Ile Val
                325                 330                 335

His Pro Tyr Ile Gln Asn Pro Asp Pro Ala Val Tyr Gln Leu Arg Asp
            340                 345                 350

Ser Lys Ser Ser Asp Lys Ser Val Cys Leu Phe Thr Asp Phe Asp Ser
        355                 360                 365

Gln Thr Asn Val Ser Gln Ser Lys Asp Ser Asp Val Tyr Ile Thr Asp
    370                 375                 380

Lys Thr Val Leu Asp Met Arg Ser Met Asp Phe Lys Ser Asn Ser Ala
```

-continued

```
            385                 390                 395                 400
        Val Ala Trp Ser Asn Lys Ser Asp Phe Ala Cys Ala Asn Ala Phe Asn
                        405                 410                 415

Asn Ser Ile Ile Pro Glu Asp Thr Phe Phe Pro Ser Pro Glu Ser Ser
                        420                 425                 430

Cys Asp Val Lys Leu Val Glu Lys Ser Phe Glu Thr Asp Thr Asn Leu
                        435                 440                 445

Asn Phe Gln Asn Leu Ser Val Ile Gly Phe Arg Ile Leu Leu Leu Lys
                        450                 455                 460

Val Ala Gly Phe Asn Leu Leu Met Thr Leu Arg Leu Trp Ser Ser Gly
        465                 470                 475                 480

Ser Arg Ala Lys Arg Ser Gly Ser Gly Ala Thr Asn Phe Ser Leu Leu
                        485                 490                 495

Lys Gln Ala Gly Asp Val Glu Glu Asn Pro Gly Pro Arg Met Ser Ile
                        500                 505                 510

Gly Leu Leu Cys Cys Ala Ala Leu Ser Leu Leu Trp Ala Gly Pro Val
                        515                 520                 525

Asn Ala Gly Val Thr Gln Thr Pro Lys Phe Gln Val Leu Lys Thr Gly
                        530                 535                 540

Gln Ser Met Thr Leu Gln Cys Ala Gln Asp Met Asn His Glu Tyr Met
        545                 550                 555                 560

Ser Trp Tyr Arg Gln Asp Pro Gly Met Gly Leu Arg Leu Ile His Tyr
                        565                 570                 575

Ser Val Gly Ala Gly Ile Thr Asp Gln Gly Glu Val Pro Asn Gly Tyr
                        580                 585                 590

Asn Val Ser Arg Ser Thr Thr Glu Asp Phe Pro Leu Arg Leu Leu Ser
                        595                 600                 605

Ala Ala Pro Ser Gln Thr Ser Val Tyr Phe Cys Ala Ser Ser Tyr Val
                        610                 615                 620

Gly Asn Thr Gly Glu Leu Phe Phe Gly Glu Gly Ser Arg Leu Thr Val
        625                 630                 635                 640

Leu Glu Asp Leu Lys Asn Val Phe Pro Pro Glu Val Ala Val Phe Glu
                        645                 650                 655

Pro Ser Glu Ala Glu Ile Ser His Thr Gln Lys Ala Thr Leu Val Cys
                        660                 665                 670

Leu Ala Thr Gly Phe Tyr Pro Asp His Val Glu Leu Ser Trp Trp Val
                        675                 680                 685

Asn Gly Lys Glu Val His Ser Gly Val Ser Thr Asp Pro Gln Pro Leu
        690                 695                 700

Lys Glu Gln Pro Ala Leu Asn Asp Ser Arg Tyr Cys Leu Ser Ser Arg
        705                 710                 715                 720

Leu Arg Val Ser Ala Thr Phe Trp Gln Asn Pro Arg Asn His Phe Arg
                        725                 730                 735

Cys Gln Val Gln Phe Tyr Gly Leu Ser Glu Asn Asp Glu Trp Thr Gln
                        740                 745                 750

Asp Arg Ala Lys Pro Val Thr Gln Ile Val Ser Ala Glu Ala Trp Gly
                        755                 760                 765

Arg Ala Asp Cys Gly Phe Thr Ser Glu Ser Tyr Gln Gln Gly Val Leu
                        770                 775                 780

Ser Ala Thr Ile Leu Tyr Glu Ile Leu Leu Gly Lys Ala Thr Leu Tyr
        785                 790                 795                 800

Ala Val Leu Val Ser Ala Leu Val Leu Met Ala Met Val Lys Arg Lys
                        805                 810                 815
```

Asp Ser Arg Gly
        820

<210> SEQ ID NO 10
<211> LENGTH: 4021
<212> TYPE: DNA
<213> ORGANISM: Artificial Sequence
<220> FEATURE:
<223> OTHER INFORMATION: Sense strand sequence spanning the region
      between the MluI and SalI restriction sites

<400> SEQUENCE: 10

| | | | | | |
|---|---|---|---|---|---|
| acgcgttaag | atacattgat | gagtttggac | aaaccacaac | tagaatgcag | tgaaaaaaat | 60 |
| gctttatttg | tgaaatttgt | gatgctattg | ctttatttgt | aaccattata | agctgcaata | 120 |
| aacaagttct | cgagtcagtg | ctctttggtg | cccatcagga | tcttgttcca | gcaggtcttg | 180 |
| atttcctgca | gcagccgctt | caggaagcac | aggtcgttca | gtttcttctg | ctctttcagg | 240 |
| gacttgttct | cttccaggct | cttggtaggc | tgggcttctc | ccagggcggc | aggctttctg | 300 |
| cccttcactt | ggccggtgca | attcagcagg | atggtggtgc | cctcggacac | tttcagcaga | 360 |
| tgcaggtcga | agtcgccggt | gctgttcatc | ttcaggaact | gccgcagctt | tctggcggct | 420 |
| ctgaacagga | acatgccttc | tttgttggcg | tcgcagatgt | gccgcttgaa | gaagttgaac | 480 |
| tcgttgttca | ggcagttgct | gccgatttcc | ttcatgctgt | ccagcagctg | gtcgatggac | 540 |
| accatcagca | cgctctcgta | ctgcttgccg | tccttgccct | cgatgtcgca | gtcgctgctg | 600 |
| gccacaggca | gcagcaccag | gatcaggggg | ggcaggccga | agatgtaccg | gaaggacacg | 660 |
| tggaacatgg | tggcggccat | atggatccaa | cgaatgtcga | gaggctggat | cggtcccggt | 720 |
| gtcttctatg | gaggtcaaaa | cagcgtggat | ggcgtctcca | ggcgatctga | cggttcacta | 780 |
| aacgagctct | gcttatatag | acctcccacc | gtacacgcct | agacgtcacg | ccttctgtat | 840 |
| gaaacagttt | ttcctccacg | ccttctgtat | gaaacagttt | ttcctccacg | ccttctgtat | 900 |
| gaaacagttt | ttcctccgct | agcgagctca | ggtaccggcc | agttaggccg | atatcatgca | 960 |
| tcgtgaggct | ccggtgcccg | tcagtgggca | gagcgcacat | cgcccacagt | ccccgagaag | 1020 |
| ttgggggggag | gggtcggcaa | ttgaaccggt | gcctagagaa | ggtggcgcgg | ggtaaactgg | 1080 |
| gaaagtgatg | tcgtgtactg | gctccgcctt | tttcccgagg | gtgggggaga | accgtatata | 1140 |
| agtgcagtag | tcgccgtgaa | cgttcttttt | cgcaacgggt | ttgccgccag | aacacaggta | 1200 |
| agtgccgtgt | gtggttcccg | cgggcctggc | ctctttacgg | gttatggccc | ttgcgtgcct | 1260 |
| tgaattactt | ccacctggct | gcagtacgtg | attcttgatc | ccgagcttcg | ggttggaagt | 1320 |
| gggtgggaga | gttcgaggcc | ttgcgcttaa | ggagcccctt | cgcctcgtgc | ttgagttgag | 1380 |
| gcctggcctg | ggcgctgggg | ccgccgcgtg | cgaatctggt | ggcaccttcg | cgcctgtctc | 1440 |
| gctgctttcg | ataagtctct | agccatttaa | aattttgat | gacctgctgc | gacgcttttt | 1500 |
| ttctggcaag | atagtcttgt | aaatgcgggc | caagatctgc | acactggtat | ttcggttttt | 1560 |
| ggggccgcgg | gcggcgacgg | ggcccgtgcg | tcccagcgca | catgttcggc | gaggcgggc | 1620 |
| ctgcgagcgc | ggccaccgag | aatcggacgg | gggtagtctc | aagctggccg | gcctgctctg | 1680 |
| gtgcctggcc | tcgcgccgcc | gtgtatcgcc | ccgccctggg | cggcaaggct | ggcccggtcg | 1740 |
| gcaccagttg | cgtgagcgga | aagatggccg | cttcccggcc | ctgctgcagg | gagctcaaaa | 1800 |
| tggaggacgc | ggcgctcggg | agagcgggcg | ggtgagtcac | ccacacaaag | gaaaagggcc | 1860 |
| tttccgtcct | cagccgtcgc | ttcatgtgac | tccactgagt | accgggcgcc | gtccaggcac | 1920 |

```
ctcgattagt tctcgtgctt ttggagtacg tcgtctttag gttgggggga ggggtttat      1980
gcgatggagt ttccccacac tgagtgggtg gagactgaag ttaggccagc ttggcacttg      2040
atgtaattct ccttggaatt tgcccttttt gagtttggat cttggttcat tctcaagcct     2100
cagacagtgg ttcaaagttt ttttcttcca tttcaggtgt cgtgagctag ccgccaccat     2160
gaagaagcac ctgaccacct ttctcgtgat cctgtggctg tacttctacc ggggcaacgg     2220
caagaaccag gtggaacaga gcccccagag cctgatcatc ctggaaggca agaactgcac     2280
cctgcagtgc aactacaccg tgtccccctt cagcaacctg cggtggtaca agcaggacac     2340
cggcagaggc cctgtgtccc tgaccatcct gaccttcagc gagaacacca gagcaacgg     2400
ccggtacacc gccaccctgg acgccgatac aaagcagagc agcctgcaca tcaccgccag     2460
ccagctgagc gatagcgcca gctacatctg cgtggtgtcc ggcggcacag acagctgggg     2520
caagctgcag tttggcgccg aacacaggt ggtcgtgacc cccgacatcc agaaccctga     2580
ccctgccgtg taccagctgc gggacagcaa gagcagcgac aagagcgtgt gcctgttcac     2640
cgacttcgac agccagacca cgtgtccca gagcaaggac agcgacgtgt acatcaccga     2700
caagaccgtg ctggacatgc ggagcatgga cttcaagagc aatagcgccg tggcctggtc     2760
caacaagagc gacttcgcct gcgccaacgc cttcaacaac agcattatcc ccgaggacac     2820
attcttccca agccccgaga gcagctgcga cgtcaagctg gtggaaaaga gcttcgagac     2880
agacaccaac ctgaacttcc agaacctgag cgtgatcggc ttcagaatcc tgctgctgaa     2940
ggtggccggc ttcaacctgc tgatgaccct gagactgtgg tccagcggca gccgggccaa     3000
gagatctgga tccggcgcta ccaactttag cctgctgaag caggccgggg acgtggaaga     3060
aaaccctggc cctaggatgg ccagcctgct gttcttctgc ggcgccttct acctgctggg     3120
caccggctct atggatgccg acgtgaccca gaccccccgg aacagaatca ccaagaccgg     3180
caagcggatc atgctggaat gctcccagac caagggccac gaccggatgt actggtacag     3240
acaggacct ggcctgggcc tgcggctgat ctactacagc ttcgacgtga aggacatcaa     3300
caagggcgag atcagcgacg gctacagcgt gtccagacag gctcaggcca agttcagcct     3360
gtccctggaa agcgccatcc caaccgac cgccctgtac ttttgtgcca caagcggcca     3420
gggcgcctac gaggagcagt tctttggccc tggcacccgg ctgacagtgc tggaagatct     3480
gaagaacgtg ttccccccag aggtggccgt gttcgagcct tctgaggccg aaatcagcca     3540
cacccagaaa gccacactcg tgtgtctggc caccggcttc taccccgacc acgtggaact     3600
gtcttggtgg gtcaacggca aagaggtgca cagcggcgtg tccaccgatc cccagcctct     3660
gaaagaacag cccgccctga acgacagccg gtactgcctg agcagcagac tgagagtgtc     3720
cgccaccttc tggcagaacc ccagaaacca cttcagatgc caggtgcagt tttacggcct     3780
gagcgagaac gacgagtgga cccaggacag agccaagccc gtgacacaga tcgtgtctgc     3840
cgaagcttgg gggcgcgccg attgtggctt taccagcgag agctaccagc agggcgtgct     3900
gagcgccacc atcctgtacg agatcctgct gggaaaggcc acactgtacg ccgtgctggt     3960
gtctgccctg gtgctgatgg ccatggtcaa gcggaaggac agccggggct aataagtcga     4020
c                                                                     4021
```

<210> SEQ ID NO 11
<211> LENGTH: 617
<212> TYPE: PRT
<213> ORGANISM: Artificial Sequence
<220> FEATURE:
<223> OTHER INFORMATION: TCR2

<400> SEQUENCE: 11

| | | | | | | | | | | | | | | |
|---|---|---|---|---|---|---|---|---|---|---|---|---|---|---|
| Met | Lys | Lys | His | Leu | Thr | Thr | Phe | Leu | Val | Ile | Leu | Trp | Leu | Tyr | Phe |
| 1 | | | | 5 | | | | | 10 | | | | | 15 | |

| Tyr | Arg | Gly | Asn | Gly | Lys | Asn | Gln | Val | Glu | Gln | Ser | Pro | Gln | Ser | Leu |
|---|---|---|---|---|---|---|---|---|---|---|---|---|---|---|---|
| | | | 20 | | | | | 25 | | | | | 30 | | |

| Ile | Ile | Leu | Glu | Gly | Lys | Asn | Cys | Thr | Leu | Gln | Cys | Asn | Tyr | Thr | Val |
| | | | | 35 | | | | | 40 | | | | | 45 | |

| Ser | Pro | Phe | Ser | Asn | Leu | Arg | Trp | Tyr | Lys | Gln | Asp | Thr | Gly | Arg | Gly |
| | 50 | | | | | 55 | | | | | 60 | | | | |

| Pro | Val | Ser | Leu | Thr | Ile | Leu | Thr | Phe | Ser | Glu | Asn | Thr | Lys | Ser | Asn |
| 65 | | | | | 70 | | | | | 75 | | | | | 80 |

| Gly | Arg | Tyr | Thr | Ala | Thr | Leu | Asp | Ala | Asp | Thr | Lys | Gln | Ser | Ser | Leu |
| | | | | 85 | | | | | 90 | | | | | 95 | |

| His | Ile | Thr | Ala | Ser | Gln | Leu | Ser | Asp | Ser | Ala | Ser | Tyr | Ile | Cys | Val |
| | | | | 100 | | | | | 105 | | | | | 110 | |

| Val | Ser | Gly | Gly | Thr | Asp | Ser | Trp | Gly | Lys | Leu | Gln | Phe | Gly | Ala | Gly |
| | | | 115 | | | | | 120 | | | | | 125 | | |

| Thr | Gln | Val | Val | Val | Thr | Pro | Asp | Ile | Gln | Asn | Pro | Asp | Pro | Ala | Val |
| 130 | | | | | 135 | | | | | 140 | | | | | |

| Tyr | Gln | Leu | Arg | Asp | Ser | Lys | Ser | Ser | Asp | Lys | Ser | Val | Cys | Leu | Phe |
| 145 | | | | | 150 | | | | | 155 | | | | | 160 |

| Thr | Asp | Phe | Asp | Ser | Gln | Thr | Asn | Val | Ser | Gln | Ser | Lys | Asp | Ser | Asp |
| | | | | 165 | | | | | 170 | | | | | 175 | |

| Val | Tyr | Ile | Thr | Asp | Lys | Thr | Val | Leu | Asp | Met | Arg | Ser | Met | Asp | Phe |
| | | | 180 | | | | | 185 | | | | | 190 | | |

| Lys | Ser | Asn | Ser | Ala | Val | Ala | Trp | Ser | Asn | Lys | Ser | Asp | Phe | Ala | Cys |
| | | 195 | | | | | 200 | | | | | 205 | | | |

| Ala | Asn | Ala | Phe | Asn | Asn | Ser | Ile | Ile | Pro | Glu | Asp | Thr | Phe | Phe | Pro |
| 210 | | | | | 215 | | | | | 220 | | | | | |

| Ser | Pro | Glu | Ser | Ser | Cys | Asp | Val | Lys | Leu | Val | Glu | Lys | Ser | Phe | Glu |
| 225 | | | | | 230 | | | | | 235 | | | | | 240 |

| Thr | Asp | Thr | Asn | Leu | Asn | Phe | Gln | Asn | Leu | Ser | Val | Ile | Gly | Phe | Arg |
| | | | | 245 | | | | | 250 | | | | | 255 | |

| Ile | Leu | Leu | Leu | Lys | Val | Ala | Gly | Phe | Asn | Leu | Leu | Met | Thr | Leu | Arg |
| | | | 260 | | | | | 265 | | | | | 270 | | |

| Leu | Trp | Ser | Ser | Gly | Ser | Arg | Ala | Lys | Arg | Ser | Gly | Ser | Gly | Ala | Thr |
| | | 275 | | | | | 280 | | | | | 285 | | | |

| Asn | Phe | Ser | Leu | Leu | Lys | Gln | Ala | Gly | Asp | Val | Glu | Glu | Asn | Pro | Gly |
| 290 | | | | | 295 | | | | | 300 | | | | | |

| Pro | Arg | Met | Ala | Ser | Leu | Leu | Phe | Phe | Cys | Gly | Ala | Phe | Tyr | Leu | Leu |
| 305 | | | | | 310 | | | | | 315 | | | | | 320 |

| Gly | Thr | Gly | Ser | Met | Asp | Ala | Asp | Val | Thr | Gln | Thr | Pro | Arg | Asn | Arg |
| | | | | 325 | | | | | 330 | | | | | 335 | |

| Ile | Thr | Lys | Thr | Gly | Lys | Arg | Ile | Met | Leu | Glu | Cys | Ser | Gln | Thr | Lys |
| | | | 340 | | | | | 345 | | | | | 350 | | |

| Gly | His | Asp | Arg | Met | Tyr | Trp | Tyr | Arg | Gln | Asp | Pro | Gly | Leu | Gly | Leu |
| | | 355 | | | | | 360 | | | | | 365 | | | |

| Arg | Leu | Ile | Tyr | Tyr | Ser | Phe | Asp | Val | Lys | Asp | Ile | Asn | Lys | Gly | Glu |
| 370 | | | | | 375 | | | | | 380 | | | | | |

| Ile | Ser | Asp | Gly | Tyr | Ser | Val | Ser | Arg | Gln | Ala | Gln | Ala | Lys | Phe | Ser |
| 385 | | | | | 390 | | | | | 395 | | | | | 400 |

| Leu | Ser | Leu | Glu | Ser | Ala | Ile | Pro | Asn | Gln | Thr | Ala | Leu | Tyr | Phe | Cys |

```
            405                 410                 415
Ala Thr Ser Gly Gln Gly Ala Tyr Glu Glu Gln Phe Phe Gly Pro Gly
        420                 425                 430

Thr Arg Leu Thr Val Leu Glu Asp Leu Lys Asn Val Phe Pro Pro Glu
            435                 440                 445

Val Ala Val Phe Glu Pro Ser Glu Ala Glu Ile Ser His Thr Gln Lys
    450                 455                 460

Ala Thr Leu Val Cys Leu Ala Thr Gly Phe Tyr Pro Asp His Val Glu
465                 470                 475                 480

Leu Ser Trp Trp Val Asn Gly Lys Glu Val His Ser Gly Val Ser Thr
                485                 490                 495

Asp Pro Gln Pro Leu Lys Glu Gln Pro Ala Leu Asn Asp Ser Arg Tyr
            500                 505                 510

Cys Leu Ser Ser Arg Leu Arg Val Ser Ala Thr Phe Trp Gln Asn Pro
        515                 520                 525

Arg Asn His Phe Arg Cys Gln Val Gln Phe Tyr Gly Leu Ser Glu Asn
    530                 535                 540

Asp Glu Trp Thr Gln Asp Arg Ala Lys Pro Val Thr Gln Ile Val Ser
545                 550                 555                 560

Ala Glu Ala Trp Gly Arg Ala Asp Cys Gly Phe Thr Ser Glu Ser Tyr
                565                 570                 575

Gln Gln Gly Val Leu Ser Ala Thr Ile Leu Tyr Glu Ile Leu Leu Gly
            580                 585                 590

Lys Ala Thr Leu Tyr Ala Val Leu Val Ser Ala Leu Val Leu Met Ala
        595                 600                 605

Met Val Lys Arg Lys Asp Ser Arg Gly
    610                 615

<210> SEQ ID NO 12
<211> LENGTH: 2512
<212> TYPE: DNA
<213> ORGANISM: Artificial Sequence
<220> FEATURE:
<223> OTHER INFORMATION: Sequence covering the region between the NheI
      and SalI restriction sites

<400> SEQUENCE: 12
gctagcgccg ccaccatgtt ccacgtgtcc ttccggtaca tcttcggcct gccccccctg      60
atcctggtgc tgctgcctgt ggccagcagc gactgcgaca tcgagggcaa ggacggcaag     120
cagtacgaga gcgtgctgat ggtgtccatc gaccagctgc tggacagcat gaaggaaatc     180
ggcagcaact gcctgaacaa cgagttcaac ttcttcaagc ggcacatctg cgacgccaac     240
aaagaaggca tgttcctgtt cagagccgcc agaaagctgc ggcagttcct gaagatgaac     300
agcaccggcg acttcgacct gcatctgctg aaagtgtccg agggcaccac catcctgctg     360
aattgcaccg ccaagtgaa gggcagaaag cctgccgccc tgggagaagc ccagcctacc     420
aagagcctgg aagagaacaa gtccctgaaa gagcagaaga actgaacga cctgtgcttc     480 ctgaagcggc tgctgcagga aatcaagacc tgctggaaca agatcctgat gggcaccaaa     540
gagcacggaa gcagagccaa gagaagcggc tctggcgcgc cgtgaagca gcccctgaac     600 ttcgacctgc tgaaactggc cggcgacgtg gaaagcaacc tggccctat gaagaagcac     660 ctgaccacct ttctcgtgat cctgtggctg tacttctacc ggggcaacgg caagaaccag     720
gtggaacaga gccccagag cctgatcatc ctggaaggca gaactgcac tctgcagtgc     780 aactacaccg tgtcccccct tcagcaacctg cgctggtaca gcaggatac cggcagaggc     840
```

```
cctgtgtccc tgaccatcct gaccttcagc gagaacacca agagcaacgg ccggtacacc   900
gccaccctgg acgccgatac aaagcagagc agcctgcaca tcaccgcctc ccagctgagc   960
gatagcgcca gctacatctg cgtggtgtcc ggcggcacag acagctgggg caagctgcag  1020
tttggcgccg aacacaggt ggtcgtgacc cccgacatcc agaaccctga ccctgccgtg  1080
taccagctgc gggacagcaa gagcagcgac aagagcgtgt gcctgttcac cgacttcgac  1140
tcccagacca acgtgtccca gagcaaggac agcgacgtgt acatcaccga caagaccgtg  1200
ctggatatgc ggagcatgga cttcaagagc aatagcgccg tggcctggtc taacaagagc  1260
gacttcgcct cgccaacgc cttcaacaac agcattatcc ccgaggacac attcttccca  1320
agccccgaga gcagctgcga cgtgaaactg gtggaaaaga gcttcgagac agacaccaac  1380
ctgaatttcc agaacctgag cgtgatcggc ttccggatcc tgctgctgaa ggtggccgga  1440
ttcaacctgc tgatgaccct gcggctgtgg tcctctggct ctcgggccaa gagaagcggc  1500
agcggcgcca ccaatttcag cctgctgaag caggcagggg atgtggaaga aatcccggc  1560
cctagaatgg cctccctgct gttttttctgc ggcgccttct acctgctggg gaccggcagc  1620
atggacgctg acgtgaccca gaccccccgg aacagaatca ccaagaccgg caagcggatc  1680
atgctggaat gcagccagac aaagggccac gaccggatgt actggtacag acaggatcca  1740
ggactgggcc tgaggctgat ctactacagc ttcgatgtga aggacatcaa caagggcgag  1800
atcagcgacg gctacagcgt gtccagacag gcccaggcca agttctccct gagcctggaa  1860
agcgccatcc ccaaccagac cgccctgtac ttttgtgcca caagcggcca gggcgcctac  1920
gaggaacagt tctttggccc tggcaccccgg ctgacagtgc tggaagatct gaagaacgtg  1980
ttccccccag aggtggcagt gttcgagcct agcgaggccg agatctccca cacccagaaa  2040
gccacactcg tgtgtctggc caccggattc taccccgacc atgtggaact gtcttggtgg  2100
gtcaacggca agaggtgca cagcggcgtg tccaccgatc cccagccct gaaagaacag  2160
cccgccctga cgacagccg gtactgcctg agcagcagac tgagagtgtc cgccaccttc  2220
tggcagaacc ccagaaatca cttcagatgc caggtgcagt tttacggcct gagcgagaac  2280
gacgagtgga cccaggatag ggccaagccc gtgactcaga tcgtgtctgc cgaagcctgg  2340
ggcagagccg attgcggctt taccagcgag agctaccagc agggcgtgct gagcgccacc  2400
atcctgtacg agatcctgct gggcaaggcc acactgtacg ccgtgctggt gtctgccctg  2460
gtgctgatgg ccatggtcaa gcggaaggac agccgggggct gatgaggtcg ac          2512
```

<210> SEQ ID NO 13
<211> LENGTH: 828
<212> TYPE: PRT
<213> ORGANISM: Artificial Sequence
<220> FEATURE:
<223> OTHER INFORMATION: Constitutive IL-7_TCR2

<400> SEQUENCE: 13

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

-continued

Asn Phe Phe Lys Arg His Ile Cys Asp Ala Asn Lys Glu Gly Met Phe
 65                  70                  75                  80

Leu Phe Arg Ala Ala Arg Lys Leu Arg Gln Phe Leu Lys Met Asn Ser
             85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His Gly Ser Arg Ala Lys Arg Ser Gly Ser Gly Ala Pro Val Lys Gln
            180                 185                 190

Thr Leu Asn Phe Asp Leu Leu Lys Leu Ala Gly Asp Val Glu Ser Asn
        195                 200                 205

Pro Gly Pro Met Lys Lys His Leu Thr Thr Phe Leu Val Ile Leu Trp
210                 215                 220

Leu Tyr Phe Tyr Arg Gly Asn Gly Lys Asn Gln Val Glu Gln Ser Pro
225                 230                 235                 240

Gln Ser Leu Ile Ile Leu Glu Gly Lys Asn Cys Thr Leu Gln Cys Asn
                245                 250                 255

Tyr Thr Val Ser Pro Phe Ser Asn Leu Arg Trp Tyr Lys Gln Asp Thr
            260                 265                 270

Gly Arg Gly Pro Val Ser Leu Thr Ile Leu Thr Phe Ser Glu Asn Thr
        275                 280                 285

Lys Ser Asn Gly Arg Tyr Thr Ala Thr Leu Asp Ala Asp Thr Lys Gln
    290                 295                 300

Ser Ser Leu His Ile Thr Ala Ser Gln Leu Ser Asp Ser Ala Ser Tyr
305                 310                 315                 320

Ile Cys Val Val Ser Gly Gly Thr Asp Ser Trp Gly Lys Leu Gln Phe
                325                 330                 335

Gly Ala Gly Thr Gln Val Val Val Thr Pro Asp Ile Gln Asn Pro Asp
            340                 345                 350

Pro Ala Val Tyr Gln Leu Arg Asp Ser Lys Ser Ser Asp Lys Ser Val
        355                 360                 365

Cys Leu Phe Thr Asp Phe Asp Ser Gln Thr Asn Val Ser Gln Ser Lys
    370                 375                 380

Asp Ser Asp Val Tyr Ile Thr Asp Lys Thr Val Leu Asp Met Arg Ser
385                 390                 395                 400

Met Asp Phe Lys Ser Asn Ser Ala Val Ala Trp Ser Asn Lys Ser Asp
                405                 410                 415

Phe Ala Cys Ala Asn Ala Phe Asn Asn Ser Ile Ile Pro Glu Asp Thr
            420                 425                 430

Phe Phe Pro Ser Pro Glu Ser Ser Cys Asp Val Lys Leu Val Glu Lys
        435                 440                 445

Ser Phe Glu Thr Asp Thr Asn Leu Asn Phe Gln Asn Leu Ser Val Ile
    450                 455                 460

Gly Phe Arg Ile Leu Leu Leu Lys Val Ala Gly Phe Asn Leu Leu Met
465                 470                 475                 480

Thr Leu Arg Leu Trp Ser Ser Gly Ser Arg Ala Lys Arg Ser Gly Ser

```
            485                 490                 495
Gly Ala Thr Asn Phe Ser Leu Leu Lys Gln Ala Gly Asp Val Glu Glu
            500                 505                 510

Asn Pro Gly Pro Arg Met Ala Ser Leu Leu Phe Phe Cys Gly Ala Phe
            515                 520                 525

Tyr Leu Leu Gly Thr Gly Ser Met Asp Ala Asp Val Thr Gln Thr Pro
            530                 535                 540

Arg Asn Arg Ile Thr Lys Thr Gly Lys Arg Ile Met Leu Glu Cys Ser
545                 550                 555                 560

Gln Thr Lys Gly His Asp Arg Met Tyr Trp Tyr Arg Gln Asp Pro Gly
                565                 570                 575

Leu Gly Leu Arg Leu Ile Tyr Tyr Ser Phe Asp Val Lys Asp Ile Asn
                580                 585                 590

Lys Gly Glu Ile Ser Asp Gly Tyr Ser Val Ser Arg Gln Ala Gln Ala
                595                 600                 605

Lys Phe Ser Leu Ser Leu Glu Ser Ala Ile Pro Asn Gln Thr Ala Leu
            610                 615                 620

Tyr Phe Cys Ala Thr Ser Gly Gln Gly Ala Tyr Glu Glu Gln Phe Phe
625                 630                 635                 640

Gly Pro Gly Thr Arg Leu Thr Val Leu Glu Asp Leu Lys Asn Val Phe
                645                 650                 655

Pro Pro Glu Val Ala Val Phe Glu Pro Ser Glu Ala Glu Ile Ser His
                660                 665                 670

Thr Gln Lys Ala Thr Leu Val Cys Leu Ala Thr Gly Phe Tyr Pro Asp
                675                 680                 685

His Val Glu Leu Ser Trp Trp Val Asn Gly Lys Glu Val His Ser Gly
            690                 695                 700

Val Ser Thr Asp Pro Gln Pro Leu Lys Glu Gln Pro Ala Leu Asn Asp
705                 710                 715                 720

Ser Arg Tyr Cys Leu Ser Ser Arg Leu Arg Val Ser Ala Thr Phe Trp
                725                 730                 735

Gln Asn Pro Arg Asn His Phe Arg Cys Gln Val Gln Phe Tyr Gly Leu
                740                 745                 750

Ser Glu Asn Asp Glu Trp Thr Gln Asp Arg Ala Lys Pro Val Thr Gln
            755                 760                 765

Ile Val Ser Ala Glu Ala Trp Gly Arg Ala Asp Cys Gly Phe Thr Ser
            770                 775                 780

Glu Ser Tyr Gln Gln Gly Val Leu Ser Ala Thr Ile Leu Tyr Glu Ile
785                 790                 795                 800

Leu Leu Gly Lys Ala Thr Leu Tyr Ala Val Leu Val Ser Ala Leu Val
                805                 810                 815

Leu Met Ala Met Val Lys Arg Lys Asp Ser Arg Gly
            820                 825

<210> SEQ ID NO 14
<211> LENGTH: 30
<212> TYPE: DNA
<213> ORGANISM: Artificial Sequence
<220> FEATURE:
<223> OTHER INFORMATION: Human IL2 promoter NFAT TRE

<400> SEQUENCE: 14
ggaggaaaaa ctgtttcata cagaaggcgt                                        30

<210> SEQ ID NO 15
```

```
<211> LENGTH: 138
<212> TYPE: DNA
<213> ORGANISM: Artificial Sequence
<220> FEATURE:
<223> OTHER INFORMATION: Minimal CMV promoter

<400> SEQUENCE: 15
taggcgtgta cggtgggagg cctatataag cagagctcgt ttagtgaacc gtcagatcgc    60
ctggagacgc catccacgct gttttgacct ccatagaaga caccgggacc gatccagcct   120
ctcgacattc gttggatc                                                 138

<210> SEQ ID NO 16
<211> LENGTH: 12
<212> TYPE: DNA
<213> ORGANISM: Artificial Sequence
<220> FEATURE:
<223> OTHER INFORMATION: Kozak sequence

<400> SEQUENCE: 16
gccgccacca tg                                                        12

<210> SEQ ID NO 17
<211> LENGTH: 29
<212> TYPE: DNA
<213> ORGANISM: Artificial Sequence
<220> FEATURE:
<223> OTHER INFORMATION: NHEI_IL_7F

<400> SEQUENCE: 17
taatgctagc gccgccacca tgttccacg                                      29

<210> SEQ ID NO 18
<211> LENGTH: 73
<212> TYPE: DNA
<213> ORGANISM: Artificial Sequence
<220> FEATURE:
<223> OTHER INFORMATION: IL7T2AR

<400> SEQUENCE: 18
cagcaggctg cctctgccct cgccagagcc gcttctcttg gctctgcttc cgtgctcttt    60
ggtgcccatc agg                                                       73

<210> SEQ ID NO 19
<211> LENGTH: 20
<212> TYPE: DNA
<213> ORGANISM: Artificial Sequence
<220> FEATURE:
<223> OTHER INFORMATION: T2AF

<400> SEQUENCE: 19
agggcagagg cagcctgctg                                                20

<210> SEQ ID NO 20
<211> LENGTH: 40
<212> TYPE: DNA
<213> ORGANISM: Artificial Sequence
<220> FEATURE:
<223> OTHER INFORMATION: BETA_SAL_REVIII

<400> SEQUENCE: 20
attattgtcg acttagcccc ggctgtcctt ccgcttcacc                          40

<210> SEQ ID NO 21
<211> LENGTH: 34
```

```
<212> TYPE: DNA
<213> ORGANISM: Artificial Sequence
<220> FEATURE:
<223> OTHER INFORMATION: primer

<400> SEQUENCE: 21
taatgctagc gccgccacca tgttccacgt gtcc                                34

<210> SEQ ID NO 22
<211> LENGTH: 32
<212> TYPE: DNA
<213> ORGANISM: Artificial Sequence
<220> FEATURE:
<223> OTHER INFORMATION: primer

<400> SEQUENCE: 22
cttcacgggc gcgccagagc cgcttctctt gg                                  32

<210> SEQ ID NO 23
<211> LENGTH: 1054
<212> TYPE: DNA
<213> ORGANISM: Artificial Sequence
<220> FEATURE:
<223> OTHER INFORMATION: ADB967 selection

<400> SEQUENCE: 23
aggcaccggt tcaattgccg acccctcccc ccaacttctc ggggactgtg ggcgatgtgc    60
gctctgccca ctgacgggca ccggagcctc acgatgcatg atatcggcct aactggccgg   120
tacctgagct cgctagcgga ggaaaaactg tttcatacag aaggcgtgga ggaaaaactg   180
tttcatacag aaggcgtgga ggaaaaactg tttcatacag aaggcgtgac gtctaggcgt   240
gtacggtggg aggcctatat aagcagagct cgtttagtga accgtcagat cgcctggaga   300
cgccatccac gctgttttga cctccataga agacaccggg accgatccag cctctcgaca   360
ttcgttggat ccatatggcc gccaccatgt tccacgtgtc cttccggtac atcttcggcc   420
tgccccccct gatcctggtg ctgctgcctg tggccagcag cgactgcgac atcgagggca   480
aggacggcaa gcagtacgag agcgtgctga tggtgtccat cgaccagctg ctggacagca   540
tgaaggaaat cggcagcaac tgcctgaaca acgagttcaa cttcttcaag cggcacatct   600
gcgacgccaa caaagaaggc atgttcctgt tcagagccgc cagaaagctg cggcagttcc   660
tgaagatgaa cagcaccggc gacttcgacc tgcatctgct gaaagtgtcc gagggcacca   720
ccatcctgct gaattgcacc ggccaagtga agggcagaaa gcctgccgcc ctgggagaag   780
cccagcctac caagagcctg gaagagaaca gtccctgaa agagcagaag aaactgaacg   840
acctgtgctt cctgaagcgg ctgctgcagg aaatcaagac ctgctggaac aagatcctga   900
tgggcaccaa agagcactga ctcgagaact tgtttattgc agcttataat ggttacaaat   960
aaagcaatag catcacaaat ttcacaaata aagcattttt ttcactgcat tctagttgtg  1020
gtttgtccaa actcatcaat gtatcttaac gcgt                              1054

<210> SEQ ID NO 24
<211> LENGTH: 181
<212> TYPE: PRT
<213> ORGANISM: Artificial Sequence
<220> FEATURE:
<223> OTHER INFORMATION: Translation ORF/CDS

<400> SEQUENCE: 24

Met Ala Ala Thr Met Phe His Val Ser Phe Arg Tyr Ile Phe Gly Leu
1               5                   10                  15
```

```
Pro Pro Leu Ile Leu Val Leu Leu Pro Val Ala Ser Ser Asp Cys Asp
            20              25              30

Ile Glu Gly Lys Asp Gly Lys Gln Tyr Glu Ser Val Leu Met Val Ser
        35              40              45

Ile Asp Gln Leu Leu Asp Ser Met Lys Glu Ile Gly Ser Asn Cys Leu
 50              55              60

Asn Asn Glu Phe Asn Phe Phe Lys Arg His Ile Cys Asp Ala Asn Lys
65              70              75              80

Glu Gly Met Phe Leu Phe Arg Ala Ala Arg Lys Leu Arg Gln Phe Leu
            85              90              95

Lys Met Asn Ser Thr Gly Asp Phe Asp Leu His Leu Leu Lys Val Ser
            100             105             110

Glu Gly Thr Thr Ile Leu Leu Asn Cys Thr Gly Gln Val Lys Gly Arg
            115             120             125

Lys Pro Ala Ala Leu Gly Glu Ala Gln Pro Thr Lys Ser Leu Glu Glu
        130             135             140

Asn Lys Ser Leu Lys Glu Gln Lys Lys Leu Asn Asp Leu Cys Phe Leu
145             150             155             160

Lys Arg Leu Leu Gln Glu Ile Lys Thr Cys Trp Asn Lys Ile Leu Met
            165             170             175

Gly Thr Lys Glu His
            180
```

T CELL MODIFICATION AND USE THEREOF

CROSS REFERENCE TO RELATED APPLICATIONS

This application is a continuation application of U.S. application Ser. No. 15/998,475, filed Aug. 15, 2018, now U.S. Pat. No. 11,111,301, which claims priority to and the benefit of United Kingdom Application No. GB 1713078.2 filed Aug. 15, 2017, the disclosures of each of which are incorporated herein by reference in their entireties.

FIELD

The present invention relates to the modification of T cells to increase their cytotoxic activity and the use of modified T cells in immunotherapy, for example for the treatment of cancer.

BACKGROUND

T cells (or T lymphocytes) are found widely distributed within tissues and the tumour environment. T cells are distinguished from other lymphocytes by the presence of T cell receptors (TCRs) on the cell surface. The TCR is a multi-subunit transmembrane complex that mediates the antigen-specific activation of T cells. The TCR confers antigen specificity on the T cell, by recognising an antigen peptide ligand that is presented on the target cell by a major histocompatibility complex (MHC) molecule.

Although peptides derived from altered or mutated proteins in tumour target cells can be recognised as foreign by T cells expressing specific TCRs, many antigens on tumour cells are simply upregulated or overexpressed (so called self-antigens) and do not induce a functional T cell response. Therefore, studies have focused on identifying target tumour antigens which are expressed, or highly expressed, in the malignant but not the normal cell type. Examples of such targets include the cancer/testis (CT) antigen NY-ESO-1, which is expressed in a wide array of human cancers but shows restricted expression in normal tissues (Chen Y-T et al. Proc Natl Acad Sci USA. 1997; 94(5):1914-1918), and the MAGE-A family of CT antigens which are expressed in a very limited number of healthy tissues (Scanlan M. J. et al. Immunol Rev. 2002; 188:22-32).

Identification of such antigens has promoted the development of targeted T cell-based immunotherapy, which has the potential to provide specific and effective cancer therapy (Ho, W. Y. et al. Cancer Cell 2003; 3:1318-1328; Morris, E. C. et al. Clin. Exp. Immunol. 2003; 131:1-7; Rosenberg, S. A. Nature 2001; 411:380-384; Boon, T. and van der Bruggen P. J. Exp. Med. 1996; 183:725-729).

The intravenous administration of interleukin 7 (IL-7) has been proposed to improve outcomes in T cell-based immunotherapy. IL-7 is known to bolster the persistence of tumour-specific T-cells (Melchionda, F. et al. J. Clin. Invest. 2005; 115:1177-87), and T-cells genetically modified to either secrete IL-7 or overexpress the IL-7 receptor (in conjunction with administered IL-7) display enhanced antitumour efficacy in preclinical models (Vera, J. F. et al. Mol. Ther. 2009; 17:880-8, Markley, J. C. and Sadelain, M. Blood 2010; 115:3508-3519). However, systemic administration of cytokines to patients with cancer has caused significant toxicity (Sportes, C. et al. Clin. Cancer Res. 2010; 16:727-35, Conlon, K. C. t al. J. Clin. Oncol. 2015; 33:74-82, Brudno, J. N. et al. Blood 2016; 127:3321-31) Alternative approaches such as genetic modification of T-cells to secrete or trans-present cytokines (Hutton L. V. et al. Proc. Natl. Acad. Sci. USA 2016; 113:E7788-97) carry a risk of severe adverse events, including neurotoxicity and cytokine release syndrome from systemic accumulation of secreted cytokine (Zhang, L. et al. Clin. Cancer Res. 21; 21:2278-88), whereas T-cells that overexpress cytokine receptors do not eliminate the need for exogenous cytokine (Vera, J. F. et al. Mol. Ther. 2009; 17:880-8). Therefore a method for safely delivering cytokines, such as IL-7, and other bioactive molecules, to T-cells remains elusive.

SUMMARY

The present inventors have unexpectedly recognised that T cells containing a nucleic acid construct that provides constitutive expression of an antigen receptor and inducible expression of a bioactive molecule, such as Interleukin 7 (IL-7), upon T cell activation, display improved antitumour properties without the high toxicity that is observed when the bioactive molecule is expressed constitutively in T cells.

A first aspect of the invention provides a nucleic acid construct comprising:
  (i) a first nucleotide sequence encoding a bioactive molecule;
  (ii) a second nucleotide sequence encoding an antigen receptor;
  (iii) an inducible promoter operably linked to the first nucleotide sequence and
  (iv) a constitutive promoter operably linked to the second nucleotide.

Preferably the bioactive molecule is a cytokine, most preferably IL-7.

A second aspect of the invention provides a vector, for example a lentiviral vector, comprising a nucleic construct of the first aspect.

A third aspect of the invention provides a population of T cells comprising a nucleic construct or a vector according to the first or second aspect.

A fourth aspect of the invention provides a population of T cells which constitutively express a heterologous antigen receptor and inducibly express a bioactive molecule, such as IL-7, upon T cell activation.

A fifth aspect of the invention provides a pharmaceutical composition comprising a population of T cells according to the third or fourth aspects and a pharmaceutically acceptable excipient.

A fifth aspect of the invention provides a population of T cells according to the third or fourth aspects for use in a method of treatment of the human or animal body, for example a method of treatment of cancer in an individual. Related aspects provide the use of a population of T cells according to the third or fourth aspects in the manufacture of a medicament for the treatment of cancer in an individual and a method of treating cancer comprising administering to an individual with cancer a population of T cells according to the third or fourth aspects.

A sixth aspect of the invention provides a method of producing a population of modified T cells comprising:
  introducing a nucleic acid construct or a vector according to the first or second aspects into a population of T cells obtained from a donor individual to produce a population of modified T cells.

A seventh aspect of the invention provides a method of treating cancer in an individual in need thereof comprising:
  introducing a nucleic acid construct or a vector according to the first or second aspects into a population of T cells obtained from a donor individual to produce a population of modified T cells, and administering the population of modified T cells to a recipient individual.

The donor individual and the recipient individual may be the same (i.e. autologous treatment; the modified T cells are obtained from an individual who is subsequently treated with the modified T cells) or the donor individual and the recipient individual may be different (i.e. allogeneic treatment; the modified T cells are obtained from one individual and subsequently used to treat a different individual).

Other aspects and embodiments of the invention are described below.

DETAILED DESCRIPTION

Figure 1:
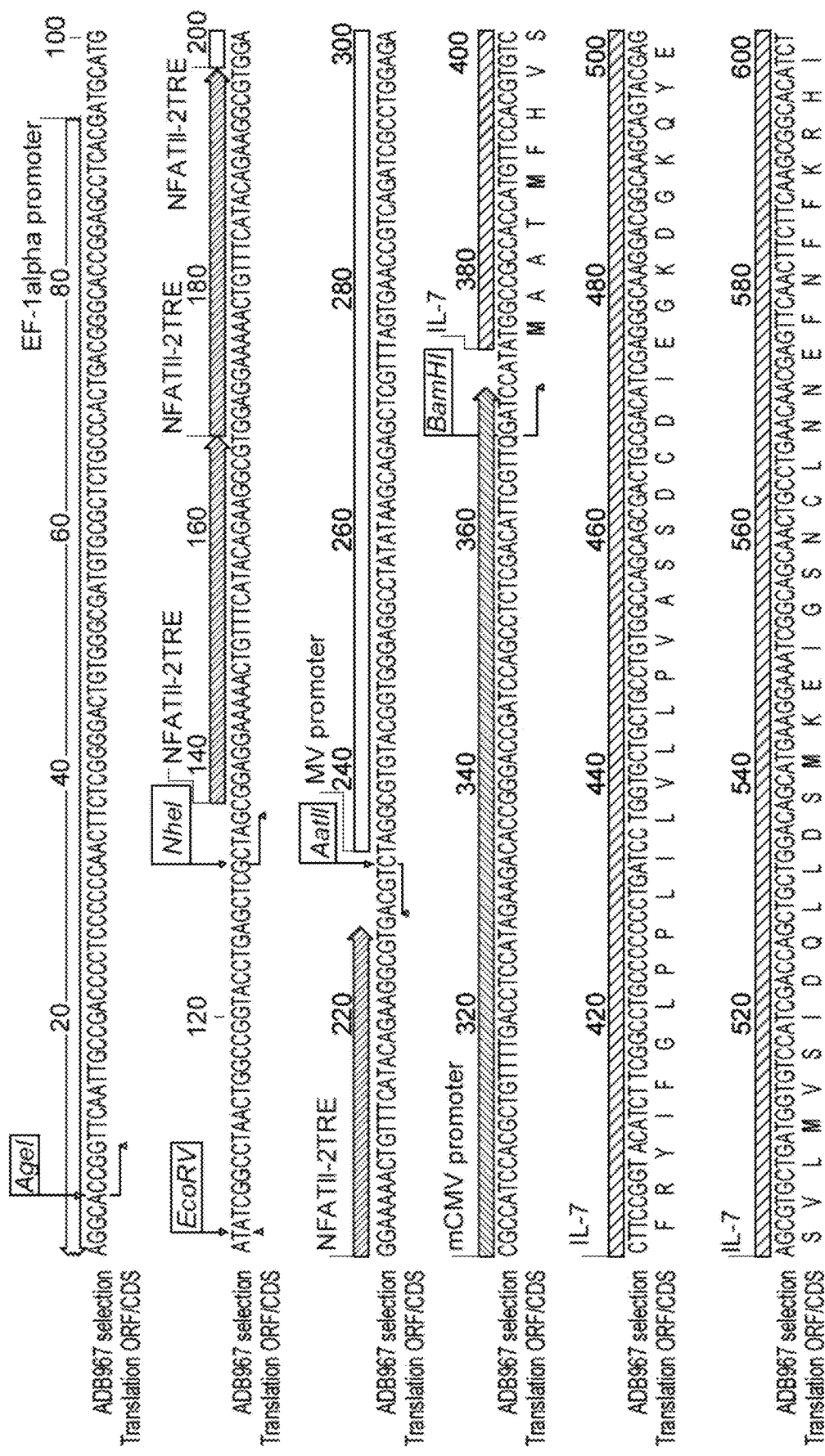
FIG. 1 shows the sequence and annotation of the NFAT inducible IL-7 expression insert. The sequence illustrated in a 5' to 3' orientation with individual components of the cassette highlighted. These include three copies of the NFAT IL-2 TRE GGAGGAAAAACTGTTTCATA-CAGAAGGCGT, minimal CMV promoter, IL-7 coding sequence (codon optimised) and the SV40 polyA.
Figure 1:
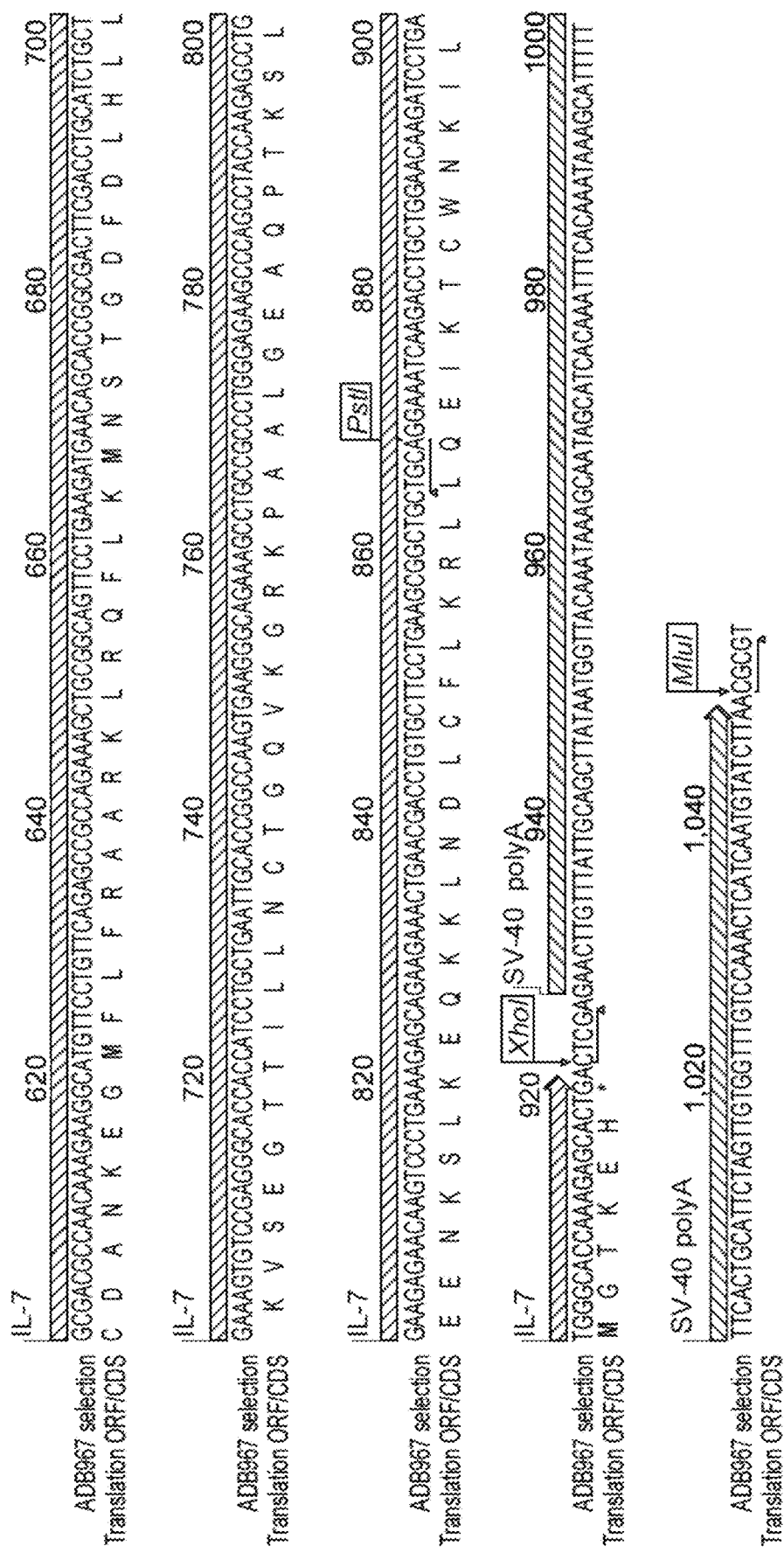

This invention relates to modified T cells that inducibly express a bioactive molecule, such as IL-7, and constitutively expresses an antigen receptor. The modified T cells may comprise a nucleic acid construct that comprises;
(i) a first nucleotide sequence encoding a bioactive molecule
(ii) a second nucleotide sequence encoding an antigen receptor;
(iii) an inducible promoter operably linked to the first nucleotide sequence and
(iv) a constitutive promoter operably linked to the second nucleotide.

T cells (also called T lymphocytes) are white blood cells that play a central role in cell-mediated immunity. T cells can be distinguished from other lymphocytes by the presence of a T cell receptor (TCR) on the cell surface. There are several types of T cells, each type having a distinct function.

T helper cells (TH cells) are known as CD4+ T cells because they express the CD4 surface glycoprotein. CD4+ T cells play an important role in the adaptive immune system and help the activity of other immune cells by releasing T cell cytokines and helping to suppress or regulate immune responses. They are essential for the activation and growth of cytotoxic T cells.

Cytotoxic T cells (Tc cells, CTLs, killer T cells) are known as CD8+ T cells because they express the CD8 surface glycoprotein. CD8+ T cells act to destroy virus-infected cells and tumour cells. Most CD8+ T cells express TCRs that can recognise a specific antigen displayed on the surface of infected or damaged cells by a class I MHC molecule. Specific binding of the TCR and CD8 glycoprotein to the antigen and MHC molecule leads to T cell-mediated destruction of the infected or damaged cells.

T cells for use as described herein may be CD4+ T cells; CD8+ T cells; or CD4+ T cells and CD8+ T cells. For example, the T cells may be a mixed population of CD4+ T cells and CD8+ T cells.

Suitable T cells for use as described herein may be obtained from a donor individual. In some embodiments, the donor individual may be the same person as the recipient individual to whom the T cells will be administered following modification and expansion as described herein (autologous treatment). In other embodiments, the donor individual may be a different person to the recipient individual to whom the T cells will be administered following modification and expansion as described herein (allogeneic treatment). For example, the donor individual may be a healthy individual who is human leukocyte antigen (HLA) matched (either before or after donation) with a recipient individual suffering from cancer.

A method described herein may comprise the step of obtaining T cells from a donor individual and/or isolating T cells from a sample obtained from a donor individual with cancer.

A population of T cells may be isolated from a blood sample. Suitable methods for the isolation of T cells are well known in the art and include, for example fluorescent activated cell sorting (FACS: see for example, Rheinherz et al (1979) PNAS 76 4061), cell panning (see for example, Lum et al (1982) Cell Immunol 72 122) and isolation using antibody coated magnetic beads (see, for example, Gaudernack et al 1986 J Immunol Methods 90 179). CD4+ and CD8+ T cells may be isolated from the population of peripheral blood mononuclear cells (PBMCs) obtained from a blood sample. PBMCs may be extracted from a blood sample using standard techniques. For example, ficoll may be used in combination with gradient centrifugation (Böyum A. Scand J Clin Lab Invest. 1968; 21(Suppl. 97):77-89), to separate whole blood into a top layer of plasma, followed by a layer of PBMCs and a bottom fraction of polymorphonuclear cells and erythrocytes. In some embodiments, the PBMCs may be depleted of CD14+ cells (monocytes).

Following isolation, the T cells may be activated. Suitable methods for activating T cells are well known in the art. For example, the isolated T cells may be exposed to a T cell receptor (TCR) agonist. Suitable TCR agonists include ligands, such as a peptide displayed on a class I or II MHC molecule on the surface of an antigen presenting cell, such as a dendritic cell, and soluble factors, such as anti-TCR antibodies.

An anti-TCR antibody may specifically bind to a component of the TCR, such as εCD3, αCD3 or αCD28. Anti-TCR antibodies suitable for TCR stimulation are well-known in the art (e.g. OKT3) and available from commercial suppliers (e.g. eBioscience CO USA). In some embodiments, T cells may be activated by exposure to anti-αCD3 antibodies and IL2. More preferably, T cells are activated by exposure to anti-αCD3 antibodies and anti-αCD28 antibodies. The activation may occur in the presence or absence of CD14+ monocytes. Preferably, the T cells may be activated with anti-CD3 and anti-CD28 antibody coated beads. For example, PBMCs or T cell subsets including CD4+ and/or CD8+ cells may be activated, without feeder cells (antigen presenting cells) or antigen, using antibody coated beads, for example magnetic beads coated with anti-CD3 and anti-CD28 antibodies, such as Dynabeads® Human T-Activator CD3/CD28 (ThermoFisher Scientific).

Following isolation and activation, the T cells may be modified to incorporate the nucleic acid construct.

The bioactive molecule and antigen receptor expressed in the modified T cell are recombinant proteins that are encoded by heterologous nucleic acid i.e. the bioactive molecule and the antigen receptor are expressed from encoding nucleic acid that has been incorporated into the T cell by recombinant techniques.

Modification of a T cell to express the bioactive molecule and the antigen receptor may comprise introducing the nucleic acid construct into the T cell. Suitable methods for the introduction and expression of heterologous nucleic acids into T cells are well-known in the art and described in more detail below.

The bioactive molecule may be a growth factor or a cytokine, preferably Interleukin 7 (IL-7). Interleukin 7 (IL-7) may be human IL-7 and may have the amino acid sequence of SEQ ID NO: 3.

Expression of IL-7 from the inducible promoter is induced by T-cell activation.

The inducible promoter may comprise a nuclear factor of activated T cells (NFAT)/AP1 transcriptional response element (TRE). Upon recognition of the cognate peptide MHC1 complex, NFAT undergoes Ca2+ dependent translocation to the nucleus where it promotes transcription of genes which harbour an NFAT TRE. Suitable NFAT TREs are well-known in the art and include the human IL2 promoter NFAT TRE (Macian et al (2001) Oncogene. 2001 Apr. 30; 20(19):2476-89) which has the sequence of SEQ ID NO: 14 or a variant thereof.

The inducible promoter may comprise one, two, three or more repeats of the NFAT TRE.

The inducible promoter may further comprise additional promoter elements, for example a minimal viral promoter such as CMV. Suitable promoter elements are well known in the art and include the minimal CMV promoter of SEQ ID NO: 15 or a variant thereof.

A suitable inducible promoter sequence operably linked to a nucleotide sequence encoding IL-7 may comprise the nucleotide sequence of SEQ ID NO: 1 or a variant thereof Expression from the constitutive promoter does not vary in response to transcription factors and the second nucleic acid sequence is expressed continuously in the T cell. Suitable constitutive promoters are well known in the art and include mammalian promoters, such as Human elongation factor-1 alpha (EF1α).

A suitable antigen receptor may bind specifically to target cells, preferably cancer cells.

The antigen receptor may be a T cell receptor (TCR). TCRs are disulphide-linked membrane anchored heterodimeric proteins, typically comprising highly variable alpha (α) and beta (β) chains expressed as a complex with invariant CD3 chain molecules. T cells expressing these type of TCRs are referred to as α:β (or αβ) T cells. A minority of T cells express an alternative TCR comprising variable gamma (γ) and delta (δ) chains and are referred to as γδ T cells.

Suitable TCRs bind specifically to a major histocompatibility complex (MHC) on the surface of cancer cells that displays a peptide fragment of a tumour antigen. An MHC is a set of cell-surface proteins which allow the acquired immune system to recognise 'foreign' molecules. Proteins are intracellularly degraded and presented on the surface of cells by the MHC. MHCs displaying 'foreign' peptides, such a viral or cancer associated peptides, are recognised by T cells with the appropriate TCRs, prompting cell destruction pathways. MHCs on the surface of cancer cells may display peptide fragments of tumour antigen i.e. an antigen which is present on a cancer cell but not the corresponding non-cancerous cell. T cells which recognise these peptide fragments may exert a cytotoxic effect on the cancer cell.

Suitable TCRs are well known in the art and include the TCRs of SEQ ID NOs: 6 and 11 and variants thereof.

In some embodiments, the coding sequences for the individual chains of the TCR (e.g. TCRα and TCRβ chains) may be separated by a cleavage recognition sequence. This allows the chains of the TCR to be expressed as a single fusion which undergoes intracellular cleavage to generate the two separate proteins. Suitable cleavage recognition sequences are well known in the art and include 2A-furin sequence.

Preferably, the TCR is not naturally expressed by the T cells (i.e. the TCR is exogenous or heterologous). Heterologous TCRs may include αβTCR heterodimers. Suitable heterologous TCRs may bind specifically to cancer cells that express a tumour antigen. For example, the T cells may be modified to express a heterologous TCR that binds specifically to MHCs displaying peptide fragments of a tumour antigen expressed by the cancer cells in a specific cancer patient. Tumour antigens expressed by cancer cells in the cancer patient may identified using standard techniques.

A heterologous TCR may be a synthetic or artificial TCR i.e. a TCR that does not exist in nature. For example, a heterologous TCR may be engineered to increase its affinity or avidity for a tumour antigen (i.e. an affinity enhanced TCR). The affinity enhanced TCR may comprise one or more mutations relative to a naturally occurring TCR, for example, one or more mutations in the hypervariable complementarity determining regions (CDRs) of the variable regions of the TCR a and R chains. These mutations increase the affinity of the TCR for MHCs that display a peptide fragment of a tumour antigen expressed by cancer cells. Suitable methods of generated affinity enhanced TCRs include screening libraries of TCR mutants using phage or yeast display and are well known in the art (see for example Robbins et al J Immunol (2008) 180(9):6116; San Miguel et al (2015) Cancer Cell 28 (3) 281-283; Schmitt et al (2013) Blood 122 348-256; Jiang et al (2015) Cancer Discovery 5 901).

Preferred affinity enhanced TCRs may bind to cancer cells expressing one or more of the tumour antigens NY-ESO1, PRAME, alpha-fetoprotein (AFP), MAGE A4, MAGE A1, MAGE A10 and MAGE B2.

Alternatively, the antigen receptor may be a chimeric antigen receptor (CAR). CARs are artificial receptors that are engineered to contain an immunoglobulin antigen binding domain, such as a single-chain variable fragment (scFv). A CAR may, for example, comprise an scFv fused to a TCR CD3 transmembrane region and endodomain. An scFv is a fusion protein of the variable regions of the heavy ($V_H$) and light ($V_L$) chains of immunoglobulins, which may be connected with a short linker peptide of approximately 10 to 25 amino acids (Huston J. S. et al. Proc Natl Acad Sci USA 1988; 85(16):5879-5883). The linker may be glycine-rich for flexibility, and serine or threonine rich for solubility, and may connect the N-terminus of the $V_H$ to the C-terminus of the $V_L$, or vice versa. The scFv may be preceded by a signal peptide to direct the protein to the endoplasmic reticulum, and subsequently the T cell surface. In the CAR, the scFv may be fused to a TCR transmembrane and endodomain. A flexible spacer may be included between the scFv and the TCR transmembrane domain to allow for variable orientation and antigen binding. The endodomain is the functional signal-transmitting domain of the receptor. An endodomain of a CAR may comprise, for example, intracellular signalling domains from the CD3ζ-chain, or from receptors such as CD28, 41BB, or ICOS. A CAR may comprise multiple signalling domains, for example, but not limited to, CD3z-CD28-41BB or CD3z-CD28-OX40.

The CAR may bind specifically to a tumour-specific antigen expressed by cancer cells. For example, the T cells may be modified to express a CAR that binds specifically to a tumour antigen that is expressed by the cancer cells in a specific cancer patient. Tumour antigens expressed by cancer cells in the cancer patient may identified using standard techniques.

Expression of a heterologous antigen receptor, such as a heterologous TCR or CAR, may alter the immunogenic specificity of the T cells so that they recognise or display improved recognition for one or more tumour antigens that are present on the surface of the cancer cells of an individual with cancer.

In some embodiments, the T cells may display reduced binding or no binding to cancer cells in the absence of the heterologous antigen receptor. For example, expression of the heterologous antigen receptor may increase the affinity and/or specificity of the cancer cell binding of modified T cells relative to unmodified T cells.

The term "heterologous" refers to a polypeptide or nucleic acid that is foreign to a particular biological system, such as a host cell, and is not naturally present in that system. A heterologous polypeptide or nucleic acid may be introduced to a biological system by artificial means, for example using recombinant techniques. For example, heterologous nucleic acid encoding a polypeptide may be inserted into a suitable expression construct which is in turn used to transform a host cell to produce the polypeptide. A heterologous polypeptide or nucleic acid may be synthetic or artificial or may exist in a different biological system, such as a different species or cell type. An endogenous polypeptide or nucleic acid is native to a particular biological system, such as a host cell, and is naturally present in that system. A recombinant polypeptide is expressed from heterologous nucleic acid that has been introduced into a cell by artificial means, for example using recombinant techniques. A recombinant polypeptide may be identical to a polypeptide that is naturally present in the cell or may be different from the polypeptides that are naturally present in that cell.

A variant of a reference amino acid or nucleotide sequence set out herein may comprise a sequence having at least 50%, at least 60%, at least 70%, at least 80%, at least 90%, at least 95%, or at least 98% sequence identity to the reference sequence. Particular amino acid sequence variants may differ from a repeat domain shown above by insertion, addition, substitution or deletion of 1 amino acid, 2, 3, 4, 5, 6, 7, 8, 9, or 10 or more than 10 amino acids. Particular nucleotide sequence variants may differ from a reference sequence set out herein by insertion, addition, substitution or deletion of 1 amino acid, 2, 3, 4, 5, 6, 7, 8, 9, or 10 or more than 10 amino acids.

Sequence similarity and identity are commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm (*Nucl. Acids Res.* (1997) 25 3389-3402) may be used.

Sequence comparison may be made over the full-length of the relevant sequence described herein.

The heterologous antigen receptor encoded by the second nucleotide sequence may specifically bind to the cancer cells of a cancer patient. The cancer patient may be subsequently treated with the modified T cells. Suitable cancer patients for treatment with the modified T cells may be identified by a method comprising:

obtaining sample of cancer cells from an individual with cancer and;

identifying the cancer cells as binding to the antigen receptor encoded by the second nucleotide sequence and expressed by the modified T cells.

Cancer cells may be identified as binding to the antigen receptor encoded by the second nucleotide sequence by identifying one or more tumour antigens expressed by the cancer cells. Methods of identifying antigens on the surface of cancer cells obtained from an individual with cancer are well-known in the art.

In some embodiments, a heterologous antigen receptor suitable for the treatment of a specific cancer patient may be identified by;

obtaining sample of cancer cells from an individual with cancer and;

identifying an antigen receptor that specifically binds to the cancer cells.

An antigen receptor that specifically binds to the cancer cells may be identified for example by identifying one or more tumour antigens expressed by the cancer cells. Methods of identifying antigens on the surface of cancer cells obtained from an individual with cancer are well-known in the art. An antigen receptor which binds to the one or more tumour antigens or which binds to MHC-displayed peptide fragments of the one or more antigens may then be identified, for example from antigen receptors of known specificities or by screening a panel or library of antigen receptors with diverse specificities. Antigen receptors that specifically bind to cancer cells having one or more defined tumour antigens may be produced using routine techniques.

Nucleic acid encoding the identified antigen receptor may be used as the second nucleotide sequence in a nucleic acid construct as described herein.

The cancer cells of an individual suitable for treatment as described herein may express the antigen and may be of correct HLA type to bind the antigen receptor.

Cancer cells may be distinguished from normal somatic cells in an individual by the expression of one or more antigens (i.e. tumour antigens). Normal somatic cells in an individual may not express the one or more antigens or may express them in a different manner, for example at lower levels, in different tissue and/or at a different developmental stage. Tumour antigens may elicit immune responses in the individual. In particular, a tumour antigen may elicit a T cell-mediated immune response against cancer cells in the individual that express the tumour antigen. One or more tumour antigens expressed by cancer cells in a patient may be selected as a target antigen for heterologous receptors on modified T cells.

Tumour antigens expressed by cancer cells may include, for example, cancer-testis (CT) antigens encoded by cancer-germ line genes, such as MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-I, GAGE-2, GAGE-3, GAGE-4, GAGE-5, GAGE-6, GAGE-7, GAGE-8, BAGE-I, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-I, LAGE-I, SSX-I, SSX-2(HOM-MEL-40), SSX-3, SSX-4, SSX-5, SCP-I and XAGE and immunogenic fragments thereof (Simpson et al. Nature Rev (2005) 5, 615-625, Gure et al., Clin Cancer Res (2005) 11, 8055-8062; Velazquez et al., Cancer Immun (2007) 7, 1 1; Andrade et al., Cancer Immun (2008) 8, 2; Tinguely et al., Cancer Science (2008); Napoletano et al., Am J of Obstet Gyn (2008) 198, 99 e91-97).

Other tumour antigens include, for example, overexpressed, upregulated or mutated proteins and differentiation antigens particularly melanocyte differentiation antigens such as p53, ras, CEA, MUC1, PMSA, PSA, tyrosinase, Melan-A, MART-1, gp100, gp75, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA- A2, HLA-A11, hsp70-2, KIAAO205, Mart2, Mum-2, and 3, neo-PAP, myosin class I, OS-9, pml-RAR.alpha. fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, TPS and tyrosinase related proteins such as TRP-1, TRP-2.

Other tumour antigens include out-of-frame peptide-MHC complexes generated by the non-AUG translation initiation mechanisms employed by "stressed" cancer cells (Malarkannan et al. Immunity 1999 June; 10(6):681-90).

Other tumour antigens are well-known in the art (see for example WO00/20581; Cancer Vaccines and Immunotherapy (2000) Eds Stern, Beverley and Carroll, Cambridge University Press, Cambridge) The sequences of these tumour antigens are readily available from public databases but are also found in WO 1992/020356 A1, WO 1994/005304 A1, WO 1994/023031 A1, WO 1995/020974 A1, WO 1995/023874 A1 and WO 1996/026214 A1.

Preferred tumour antigens include NY-ESO1, PRAME, alpha-fetoprotein (AFP), MAGE A4, MAGE A1, MAGE A10 and MAGE B2, most preferably NY-ESO-1 and MAGE-A10. NY-ESO-1 is a human tumour antigen of the cancer/testis (CT) family and is frequently expressed in a wide variety of cancers, including melanoma, prostate, transitional cell bladder, breast, lung, thyroid, gastric, head and neck, and cervical carcinoma (van Rhee F. et al. Blood 2005; 105(10):3939-3944). In addition, expression of NY-ESO-1 is usually limited to germ cells and is not expressed in somatic cells (Scanlan M. J. et al. Cancer Immun. 2004; 4(1)). Suitable affinity enhanced TCRs that bind to cancer cells expressing NY-ESO-1 include NY-ESO-1 $c^{259}$.

NY-ESO-1 $c^{259}$ is an affinity enhanced TCR is mutated at positions 95 and 96 of the alpha chain 95:96LY relative to the wildtype TCR. NY-ESO-1 $c^{259}$ binds to a peptide corresponding to amino acid residues 157-165 of the human cancer testis Ag NY-ESO-1 (SLLMWITQC) in the context of the HLA-A2+ class 1 allele with increased affinity relative to the unmodified wild type TCR (Robbins et al J Immunol (2008) 180(9):6116).

MAGE-A10 is a highly immunogenic member of the MAGE-A family of CT antigens, and is expressed in germ cells but not in healthy tissue. MAGE-A10 is expressed in high percentages of cancer cells from a number of tumours (Schultz-Thater E. et al. Int J Cancer. 2011; 129(5):1137-1148).

The introduction of the nucleic acid construct into T cells and their subsequent expansion may be performed in vitro and/or ex vivo.

The first nucleotide sequence encoding the bioactive molecule and the second nucleotide sequence encoding the antigen receptor are introduced into the T cells in the same expression vector. This increases the proportion of T cells which express both genes after transduction.

The first nucleotide sequence may be configured for expression in a first direction and the second nucleotide sequence may be configured for expression in a second direction in the nucleic acid construct. For example, the first nucleotide sequence encoding IL-7 may be in the forward orientation in the nucleic acid construct and the second nucleotide sequence encoding the antigen receptor may be in the reverse orientation or the first nucleotide sequence encoding IL-7 may be in the reverse orientation and the second nucleotide sequence encoding the antigen receptor may be in the forward orientation. The first nucleotide sequence may be transcribed from the sense strand of the nucleic acid construct and the second nucleotide sequence may be transcribed from the antisense strand of the nucleic acid construct or the first nucleotide sequence may be transcribed from the antisense strand of the nucleic acid construct and the second nucleotide sequence may be transcribed from the sense strand of the nucleic acid construct.

The nucleic acid construct may include one or more unique restriction sites to facilitate further manipulation.

In some embodiments, the nucleic acid construct may be introduced directly until T cells using gene editing techniques.

In other embodiments, the nucleic acid construct may be incorporated into an expression vector. Suitable vectors are well known in the art and are described in more detail herein.

Examples of suitable vectors include AB1581 and ADB967 as described below. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in mammalian cells. A vector may also comprise sequences, such as origins of replication, promoter regions and selectable markers, which allow for its selection, expression and replication in bacterial hosts such as *E. coli*.

Preferably, the nucleic acid construct is contained in a viral vector, most preferably a gamma retroviral vector or a lentiviral vector, such as a VSVg-pseudotyped lentiviral vector. The T cells may be transduced by contact with a viral particle comprising the nucleic acid. Viral particles for transduction may be produced according to known methods. For example, HEK293T cells may be transfected with plasmids encoding viral packaging and envelope elements as well as a lentiviral vector comprising the coding nucleic acid. A VSVg-pseudotyped viral vector may be produced in combination with the viral envelope glycoprotein G of the Vesicular stomatitis virus (VSVg) to produce a pseudotyped virus particle A viral vector, such as a lentivirus, may be contained in a viral particle comprising the nucleic acid vector encapsulated by one or more viral proteins. A viral particle may be produced by a method comprising transducing mammalian cells with a viral vector as described herein and one or more viral packaging and envelope vectors and culturing the transduced cells in a culture medium, such that the cells produce lentiviral particles that are released into the medium.

Following release of viral particles, the culture medium comprising the viral particles may be collected and, optionally the viral particles may be concentrated.

Following production and optional concentration, the viral particles may be stored, for example by freezing at −80° C. ready for use in transducing T cells.

The nucleic acid construct or vector may be introduced into the T cells by any convenient method. When introducing or incorporating a heterologous nucleic acid into a T cell, certain considerations must be taken into account, well-known to those skilled in the art. The nucleic acid to be inserted should be assembled within a construct or vector which contains effective regulatory elements which will drive transcription in the T cell. Suitable techniques for transporting the constructor vector into the T cell are well known in the art and include calcium phosphate transfection, DEAE-Dextran, electroporation, liposome-mediated transfection and transduction using retrovirus or other virus, e.g. vaccinia or lentivirus. For example, solid-phase transduction may be performed without selection by culture on retronectin-coated, retroviral vector-preloaded tissue culture plates.

Many known techniques and protocols for manipulation and transformation of nucleic acid, for example in preparation of nucleic acid constructs, introduction of DNA into cells and gene expression are described in detail in Protocols in Molecular Biology, Second Edition, Ausubel et al. eds. John Wiley & Sons, 1992.

Following the introduction of nucleic acid into the T cells, the initial population of modified T cells may be cultured in vitro such that the modified T cells proliferate and expand the population.

The modified T cell population may for example be expanded using magnetic beads coated with anti-CD3 and anti-CD28. The modified T cells may be cultured using any convenient technique to produce the expanded population. Suitable culture systems include stirred tank fermenters, airlift fermenters, roller bottles, culture bags or dishes, and other bioreactors, in particular hollow fibre bioreactors. The use of such systems is well-known in the art.

Numerous culture media suitable for use in the proliferation of T cells ex vivo are available, in particular complete media, such as AIM-V, Iscoves medium and RPMI-1640 (Invitrogen-GIBCO). The medium may be supplemented with other factors such as serum, serum proteins and selective agents. For example, in some embodiments, RPMI-1640 medium containing 2 mM glutamine, 10% FBS, 25 mM HEPES, pH 7.2, 1% penicillin-streptomycin, and 55 µM β-mercaptoethanol and optionally supplemented with 20 ng/ml recombinant IL-2 may be employed. The culture medium may be supplemented with the agonistic or antagonist factors described above at standard concentrations which may readily be determined by the skilled person by routine experimentation.

Conveniently, cells are cultured at 37° C. in a humidified atmosphere containing 5% $CO_2$ in a suitable culture medium.

Methods and techniques for the culture of T cells and other mammalian cells are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52)

In some embodiments, it may be convenient to isolate and/or purify the modified T cells from the population. Any convenient technique may be used, including FACS and antibody coated magnetic particles.

Optionally, the population of modified T cells produced as described herein may be stored, for example by lyophilisation and/or cryopreservation, before use.

A population of modified T cells may be admixed with other reagents, such as buffers, carriers, diluents, preservatives and/or pharmaceutically acceptable excipients. Suitable reagents are described in more detail below. A method described herein may comprise admixing the population of modified T cells with a pharmaceutically acceptable excipient.

Pharmaceutical compositions suitable for administration (e.g. by infusion), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents. Examples of suitable isotonic vehicles for use in such formulations include Sodium Chloride Injection, Ringer's Solution, or Lactated Ringer's Injection. Suitable vehicles can be found in standard pharmaceutical texts, for example, Remington's Pharmaceutical Sciences, 18th edition, Mack Publishing Company, Easton, Pa., 1990.

In some preferred embodiments, the modified T cells may be formulated into a pharmaceutical composition suitable for intravenous infusion into an individual.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Other aspects of the invention provide a population of modified T cells expressing a nucleic construct or a vector as described herein and a population of T cells that constitutively express a heterologous antigen receptor and express IL-7 inducibly upon T cell activation.

The T cells may bind specifically to cancer cells. A suitable population may be produced by a method described above.

The population of modified T cells may be for use as a medicament. For example, a population of modified T cells as described herein may be used in cancer immunotherapy therapy, for example adoptive T cell therapy.

Other aspects of the invention provide the use of a population of modified T cells as described herein for the manufacture of a medicament for the treatment of cancer, a population of modified T cells as described herein for the treatment of cancer, and a method of treatment of cancer may comprise administering a population of modified T cells as described herein to an individual in need thereof.

The population of modified T cells may be autologous i.e. the modified T cells were originally obtained from the same individual to whom they are subsequently administered (i.e. the donor and recipient individual are the same). A suitable population of modified T cells for administration to the individual may be produced by a method comprising providing an initial population of T cells obtained from the individual, modifying the T cells to inducibly express IL-7 and constitutively express an antigen receptor which binds specifically to cancer cells in the individual as described herein, and culturing the modified T cells.

The population of modified T cells may be allogeneic i.e. the modified T cells were originally obtained from a different individual to the individual to whom they are subsequently administered (i.e. the donor and recipient individual are different). The donor and recipient individuals may be HLA matched to avoid GVHD and other undesirable immune effects. A suitable population of modified T cells for administration to a recipient individual may be produced by a method comprising providing an initial population of T cells obtained from a donor individual, modifying the T cells to inducibly express IL-7 and constitutively express an antigen receptor which binds specifically to cancer cells in the recipient individual, as described herein, and culturing the modified T cells.

Following administration of the modified T cells, the recipient individual may exhibit a T cell mediated immune response against cancer cells in the recipient individual. This may have a beneficial effect on the cancer condition in the individual.

Cancer conditions may be characterised by the abnormal proliferation of malignant cancer cells and may include leukaemias, such as AML, CML, ALL and CLL, lymphomas, such as Hodgkin lymphoma, non-Hodgkin lymphoma and multiple myeloma, and solid cancers such as sarcomas, skin cancer, melanoma, bladder cancer, brain cancer, breast cancer, uterus cancer, ovary cancer, prostate cancer, lung cancer, colorectal cancer, cervical cancer, liver cancer, head and neck cancer, oesophageal cancer, pancreas cancer, renal cancer, adrenal cancer, stomach cancer, testicular cancer, cancer of the gall bladder and biliary tracts, thyroid cancer, thymus cancer, cancer of bone, and cerebral cancer, as well as cancer of unknown primary (CUP).

Cancer cells within an individual may be immunologically distinct from normal somatic cells in the individual (i.e. the cancerous tumour may be immunogenic). For example, the cancer cells may be capable of eliciting a systemic immune response in the individual against one or more antigens expressed by the cancer cells. The tumour antigens that elicit the immune response may be specific to cancer cells or may be shared by one or more normal cells in the individual.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In preferred embodiments, the individual is a human. In other preferred embodiments, non-human mammals, especially mammals that are conventionally used as models for demonstrating therapeutic efficacy in humans (e.g. murine, primate, porcine, canine, or rabbit animals) may be employed.

In some embodiments, the individual may have minimal residual disease (MRD) after an initial cancer treatment.

An individual with cancer may display at least one identifiable sign, symptom, or laboratory finding that is sufficient to make a diagnosis of cancer in accordance with clinical standards known in the art. Examples of such clinical standards can be found in textbooks of medicine such as Harrison's Principles of Internal Medicine, 15th Ed., Fauci A S et al., eds., McGraw-Hill, New York, 2001. In some instances, a diagnosis of a cancer in an individual may include identification of a particular cell type (e.g. a cancer cell) in a sample of a body fluid or tissue obtained from the individual.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment may also be prophylactic (i.e. prophylaxis). For example, an individual susceptible to or at risk of the occurrence or re-occurrence of cancer may be treated as described herein. Such treatment may prevent or delay the occurrence or re-occurrence of cancer in the individual.

In particular, treatment may include inhibiting cancer growth, including complete cancer remission, and/or inhibiting cancer metastasis. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of T cells, and a decrease in levels of tumour-specific antigens. Administration of T cells modified as described herein may improve the capacity of the individual to resist cancer growth, in particular growth of a cancer already present the subject and/or decrease the propensity for cancer growth in the individual.

The modified T cells or the pharmaceutical composition comprising the modified T cells may be administered to a subject by any convenient route of administration, whether systemically/peripherally or at the site of desired action, including but not limited to; parenteral, for example, by infusion. Infusion involves the administration of the T cells in a suitable composition through a needle or catheter. Typically, T cells are infused intravenously or subcutaneously, although the T cells may be infused via other non-oral routes, such as intramuscular injections and epidural routes. Suitable infusion techniques are known in the art and commonly used in therapy (see, e.g., Rosenberg et al., New Eng. J. of Med., 319:1676, 1988).

Typically, the number of cells administered is from about $10^5$ to about $10^{10}$ per Kg body weight, typically $2 \times 10^8$ to $2 \times 10^{10}$ cells per individual, typically over the course of 30 minutes, with treatment repeated as necessary, for example at intervals of days to weeks. It will be appreciated that appropriate dosages of the modified T cells, and compositions comprising the modified T cells, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular cells, the route of administration, the time of administration, the rate of loss or inactivation of the cells, the duration of the treatment, other drugs, compounds, and/or materials used in combination, and the age, sex, weight, condition, general health, and prior medical history of the patient. The amount of cells and the route of administration will ultimately be at the discretion of the physician, although generally the dosage will be to achieve local concentrations at the site of action which achieve the desired effect without causing substantial harmful or deleterious side-effects.

While the modified T cells may be administered alone, in some circumstances the modified T cells may be administered cells in combination with the target antigen, APCs displaying the target antigen, and/or IL-2 to promote expansion in vivo of the population of modified T cells. The population of modified T cells may be administered in combination with one or more other therapies, such as cytokines e.g. IL-2, cytotoxic chemotherapy, radiation and immuno-oncology agents, including checkpoint inhibitors, such as anti-B7-H3, anti-B7-H4, anti-TIM3, anti-KIR, anti-LAG3, anti-PD-1, anti-PD-L1, and anti-CTLA4 antibodies.

The one or more other therapies may be administered by any convenient means, preferably at a site which is separate from the site of administration of the modified T cells.

Administration of modified T cells can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. Preferably, the modified T cells are administered in a single transfusion of a least $1 \times 10^9$ T-cells.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Other aspects and embodiments of the invention provide the aspects and embodiments described above with the term "comprising" replaced by the term "consisting of" and the aspects and embodiments described above with the term "comprising" replaced by the term "consisting essentially of".

Certain aspects and embodiments of the invention will now be illustrated by way of example and with reference to the figures described above.

EXPERIMENTS

1. Methods 1.1 Design and Production of IL-7 Expression Constructs

A lentiviral expression vector was designed that permitted the inducible expression of IL-7 following recognition of the cognate peptide MHC1 complex. The inducible element was based on NFAT/AP1 transcriptional response element (TRE) that is present in the human IL2 promoter (Macian et al., 2001 Oncogene). The selective inducible expression of IL-7 is a result of TCR activation, and $Ca^{2+}$ dependent translocation of NFAT to the nucleus where it can promote transcription of genes which harbour an NFAT TRE.

The IL-7 expression cassette was is composed of four elements as illustrated in FIG. 1.
1. 3 tandem repeats of the human IL2 promoter NFAT TRE highlighted in red (GGAGGAAAAACTGTTTCATACAGAAGGCGT)

2. Minimal CMV promoter (green)
3. Kozak sequence (GCCGCCACCATG) and codon optimised IL-7 coding sequence (Yellow). Supplementary FIG. 1 contains the wild-type nucleotide sequence
4. SV40 polyadenylation signal (purple)

The sequence upstream of the EcorV restriction (highlighted in green in FIG. 1) corresponds to the lentiviral vector backbone sequence and was included in the synthetic construct in order to maintain the coding sequence of the EF1A promoter. Additional unique restriction sites were also designed into the synthetic construct in order to permit further engineering of the construct should it be required. These include:
1. EcoRV (GATATC) and NSI-I (ATGCAT) restriction sites upstream of the NFAT IL-2 TRE
2. NdeI restriction site CATATG immediately upstream of the IL-7 CDS
3. XhoI (CTCGAG) immediately following the TGA stop codon in the IL-7 CDS
4. AatII restriction site (GACGTC) immediately upstream of the mCMV promoter.

This construct was designed to be cloned between the AgeI and MluI restriction sites within a construct expressing a TCR alone (FIG. 2) and will permit transcription of the IL-7 from the antisense strand and in reverse orientation to the SPEAR TCR. Additional constructs were designed that permitted the constitutive expression of IL-7 and the SPEAR TCR. These constructs encode IL-7 and the TCRα and TCRβ chains as a single open reading frame. The individual polypeptides are separated by self-cleaving 2A-like peptides that permit ribosomal skipping and the expression of multiple polypeptides from a single transcript.

1.2 Generation of ADB967 NFAT IL-7_TCR1

Figure 2:
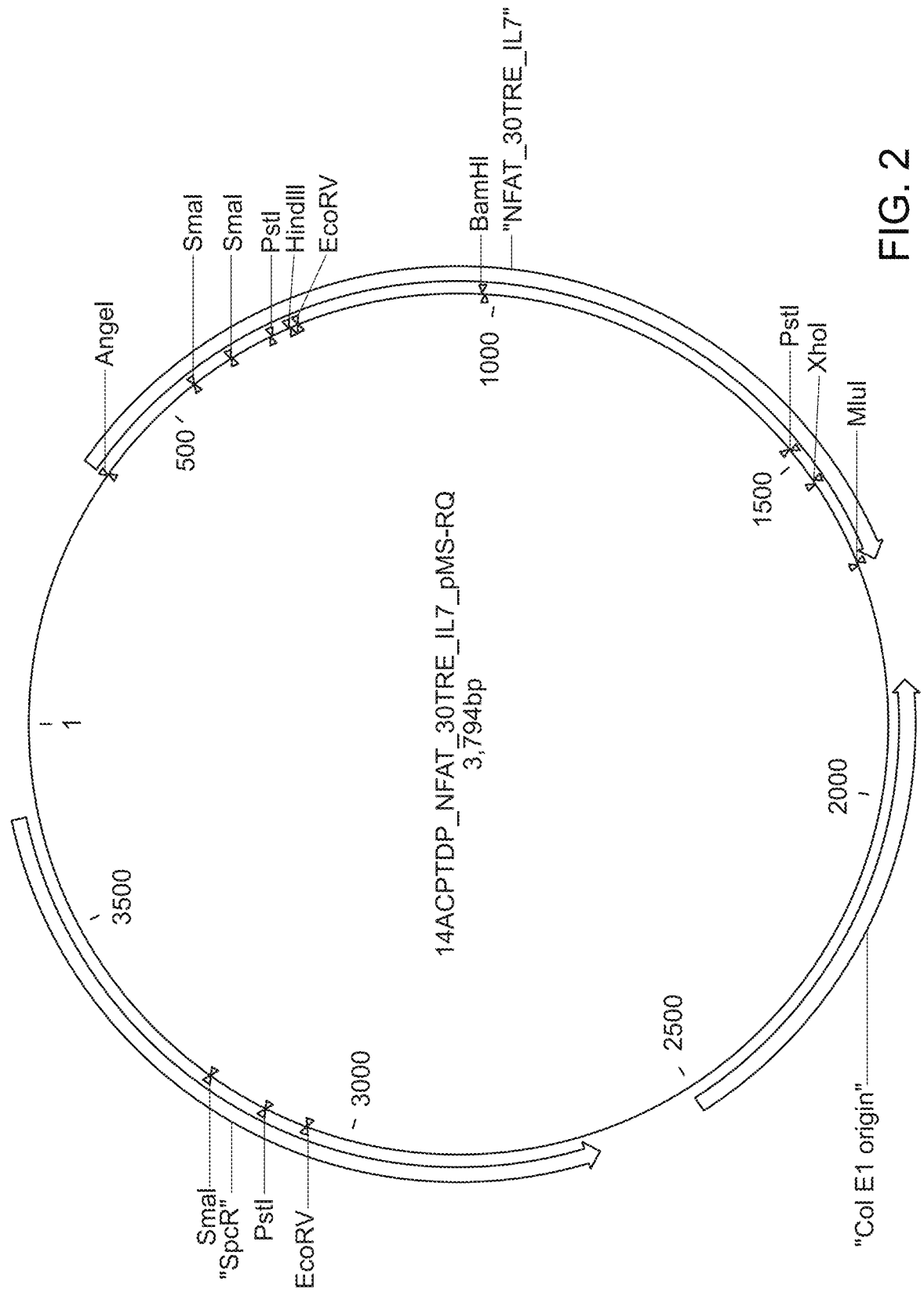
FIG. 2 shows a map of the NFAT-IL-7 plasmid supplied by GeneArt. The NFAT-IL-7 cassette was removed by digestion with AgeI and MluI.
Figure 3:
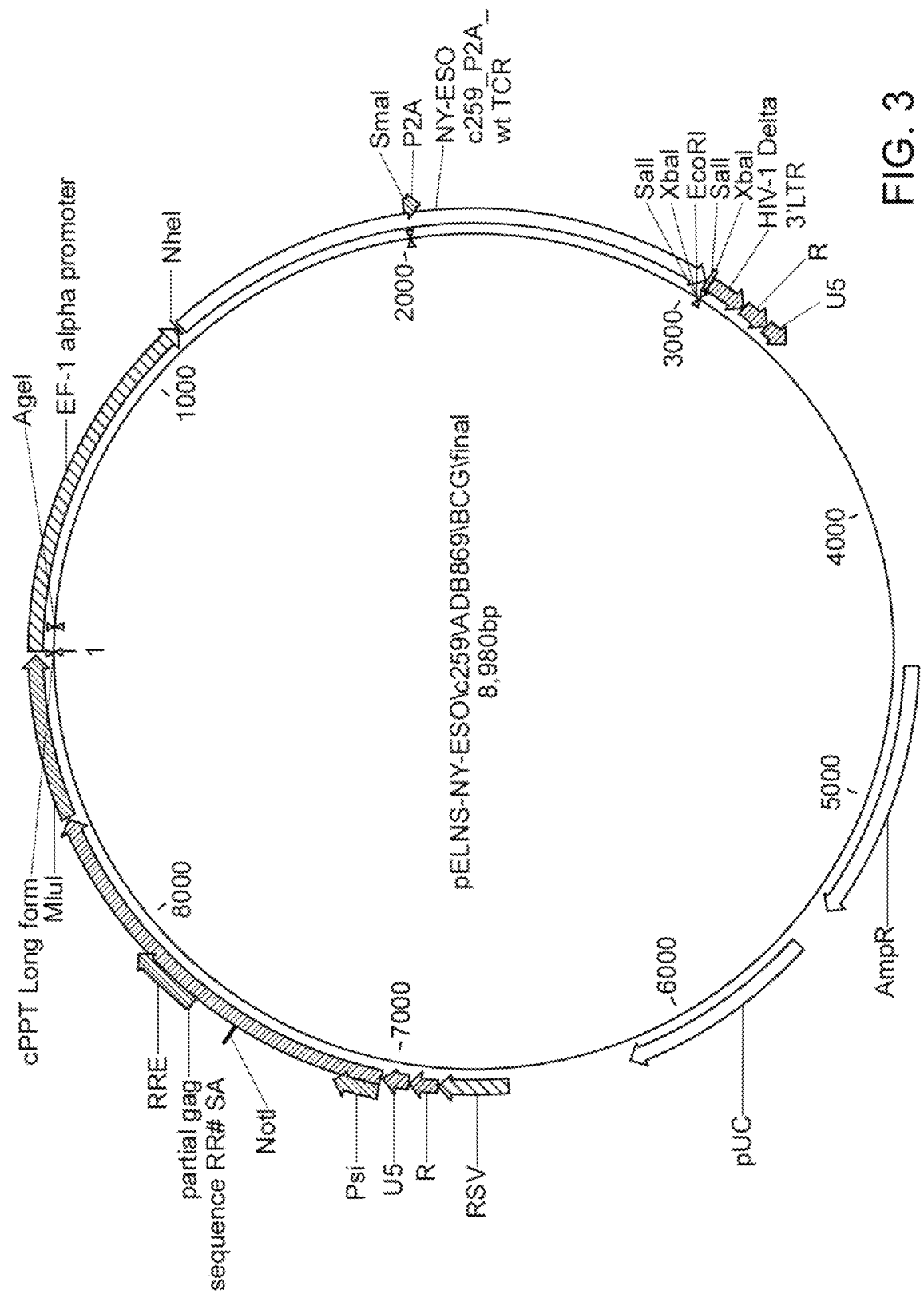
FIG. 3 shows a vector map of the lentiviral vector expressing the TCR1. Highlighted are the unique AgeI and MluI restriction
Figure 4:
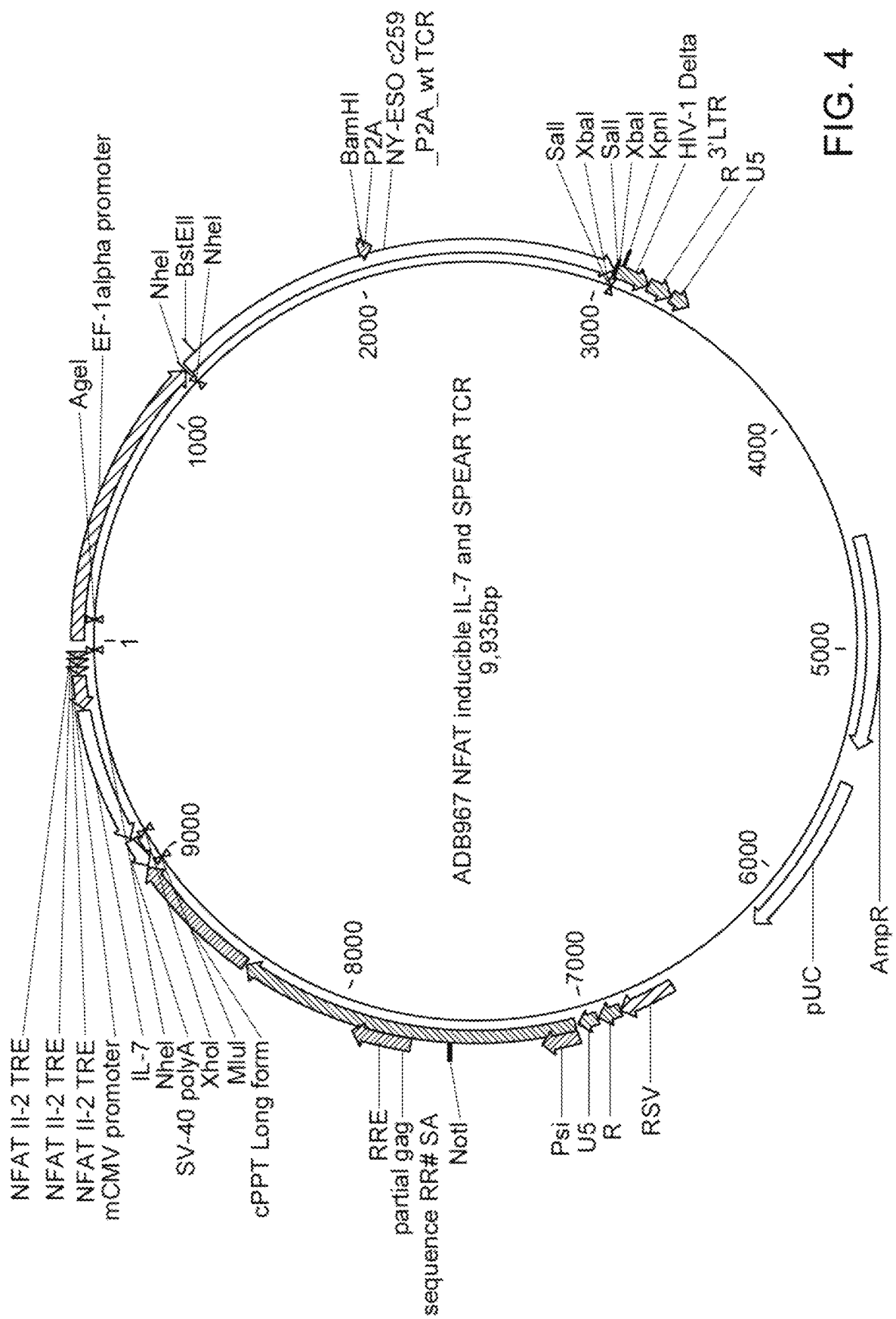
FIG. 4 shows a vector map of construct ADB967. The NFAT-IL-7 cassette was cloned between the AgeI and MluI restriction sites. Transcription of IL-7 occurs from the antisense strand and in a reverse orientation to that of the TCR1.

The NFAT_IL-7 cassette (SEQ ID NO: 1) was synthesised synthetically by GeneArt (Thermo Fisher Scientific) with 5' AgeI (ACCGGT) 3' MluI (ACGCGT) restriction sites and was provided in a standard cloning vector (pMS-RQ) (FIG. 2). The NFAT_IL-7 containing vectors and ADB934 (TCR1) were digested with AgeI and MluI and the fragments of interest were purified by gel extraction using a NucleoSpin® gel extraction kit according to manufacturer's instruction. Digested fragments were ligated using T4 DNA ligase (NEB) according to standard protocols. Clones were screened by restriction enzyme digest and verified by sequencing (see the vector map of FIG. 4).

1.3 Generation of ADB1099 Constitutive IL-7_TCR1

Figure 5:
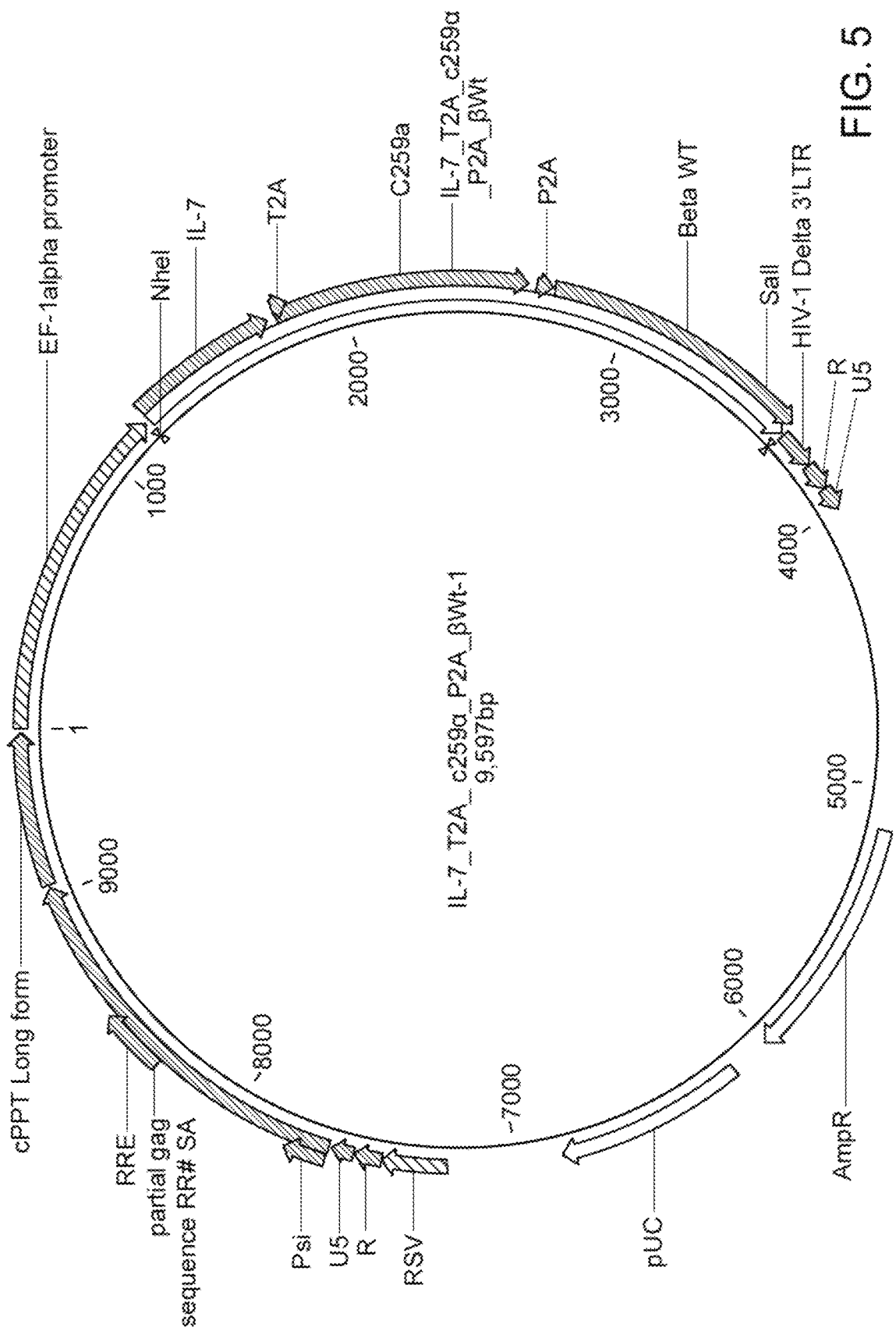
FIG. 5 shows a vector map of ADB1099 IL7_T2A_TCR1. IL7_T2A_TCR1 is expressed as a single ORF with IL-7, TCRα and TCRβ chains separated by 2A like skip sequences.

The IL-7_T2A_TCR1 insert was generated by overlapping PCR. The IL-7 CDS was amplified with primers NHEI_IL_7F and IL7_T2AR. The TCR1 CDS was amplified with the primers T2AF and BETA_SAL_REVIII. The TCR1 CDS was amplified from an existing in-house construct ADB951. PCR reactions were performed with Q5 DNA polymerase (NEB) according to standard protocols and PCR products were purified by gel extraction using a NucleoSpin® gel extraction kit according to manufacturer's instruction. The two fragments were fused together by overlapping PCR with the NHEI_IL_7F and BETA_SAL_REVIII primers which contain NheI (GCTAGC) and SalI (GTCGAC) restriction sites (underlined). Digested fragments were ligated using T4 DNA ligase (NEB) according to standard protocols. Clones were screened by restriction enzyme digest and verified by sequencing (see the vector map of FIG. 5).

| Primer | Sequence |
|---|---|
| NHEI_IL_7F | TAATGCTAGCGCCGCCACCATGTTCCACG |
| IL7T2AR | CAGCAGGCTGCCTCTGCCCTCGCCAGAGC CGCTTCTCTTGGCTCTGCTTCCGTGCTCT TTGGTGCCCATCAGG |
| T2AF | AGGGCAGAGGCAGCCTGCTG |
| BETA_SAL_REVIII | ATTATTGTCGACTTAGCCCCGGCTGTCCT TCCGCTTCACC |

1.4 Generation of ADB1581 NFAT IL-7_TCR2

The TCR2 insert was subcloned from in-house construct ADB1535 into ADB1224. ABD1535 and ADB1224 were digested with NheI and SalI restriction enzymes and fragments of interest were purified by gel extraction using a NucleoSpin® gel extraction kit according to manufacturer's instruction. Digested fragments were ligated using T4 DNA ligase (NEB) according to standard protocols. The NFAT IL-7 cassette was subcloned from ADB967 (NFAT-IL-7_TCR1) into this new TCR2 lentiviral expression vector between the AgeI and MluI restriction sites. Clones were screened by restriction enzyme digest and verified by sequencing (see the vector map of FIG. 6).

1.5 Generation of ADB1580 Constitutive IL-7_F2A_TCR2

Figure 7:
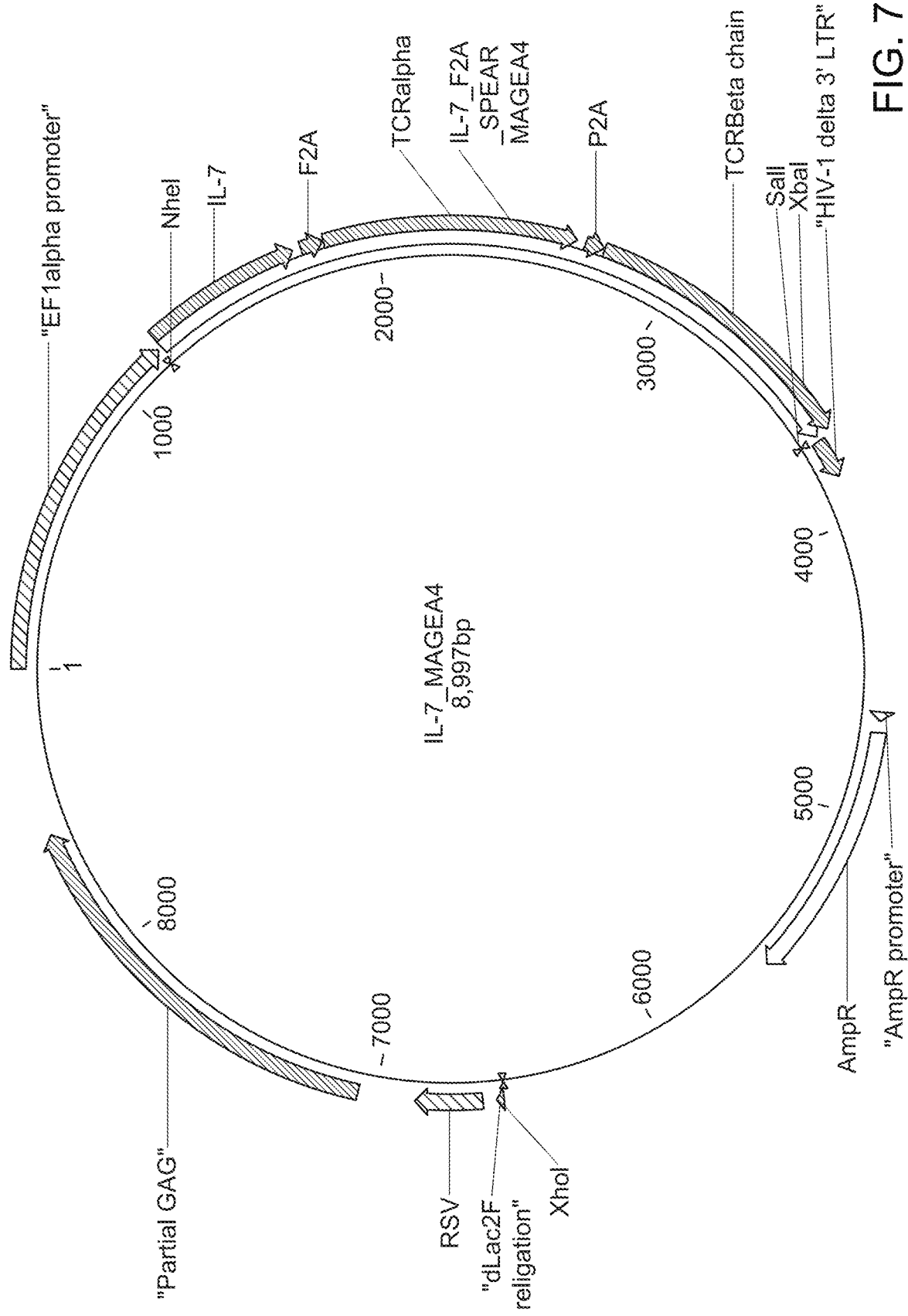
FIG. 7 shows a vector map of constitutive IL-7_TCR2. The IL-7_TCR2 was cloned into the vector AB1224 between the NheI and SalI sites.
Figure 8:
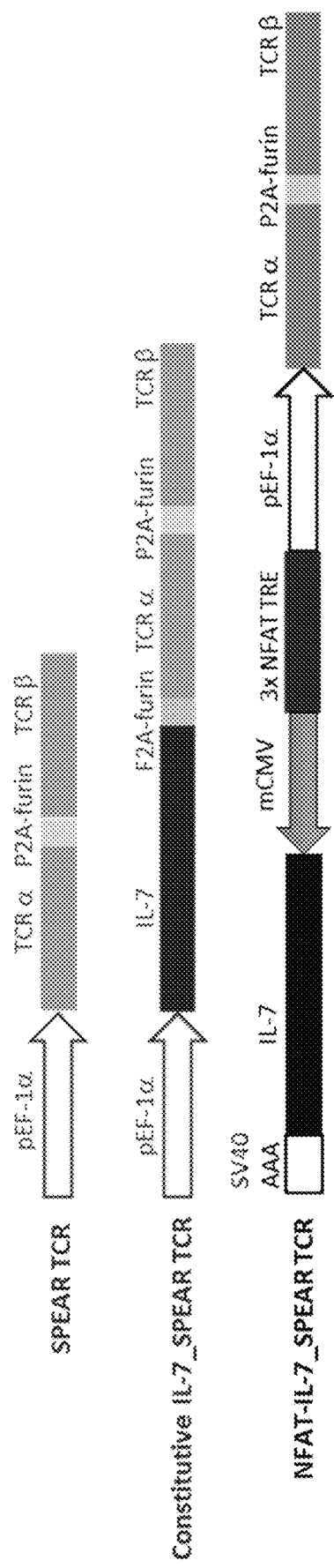
FIG. 8 shows a schematic of the design of the three main lentiviral constructs used in this study. Constructs were produced that express IL-7 under the control of 3 repeats of the NFAT promotor derived from the IL-2 promotor sequence in one direction or IL-7 constitutively in the presence SPEAR TCR and constitutive expression of the SPEAR TCR. Note: the sizes of the various components of the constructs are not shown to-scale.
Figure 9:
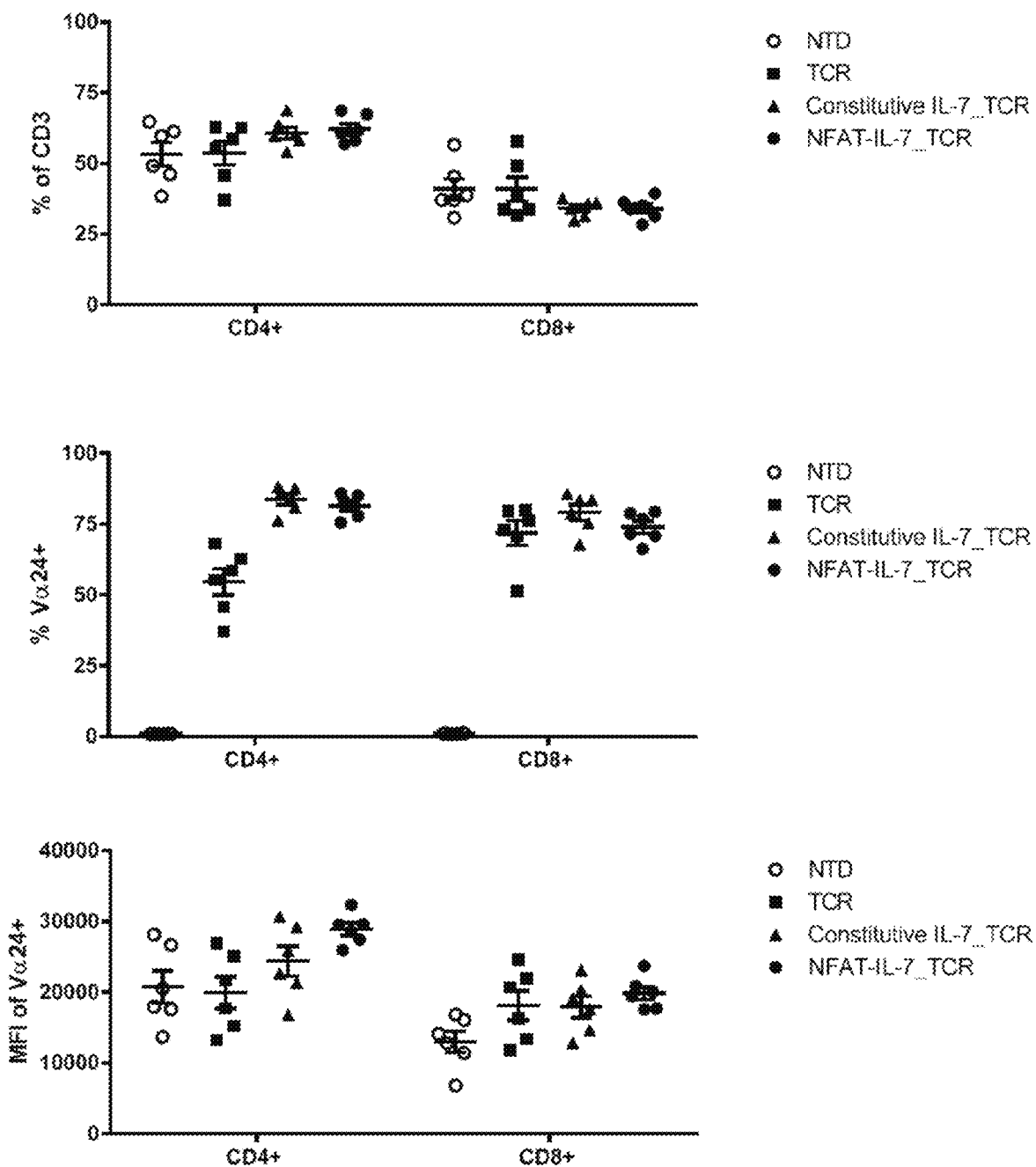
FIG. 9 shows an assessment of the percentage of CD4+ and CD8+ T cells and of T cell transduction efficiency. NTD T cells (white circles), T cells transduced with TCR (black squares), constitutive IL-7_TCR (black triangles) or with NFAT_IL-7_TCR (black circles). Data shows mean+/−SD. (A) The data are shown as the percentage of CD3+ T cells that were either CD4+ or CD8+. (B) The data are shown as the percentage of cells that were CD3+ and either CD4+ or CD8+ and that were TCR Vα24+. (C) The data are shown as the mean fluorescence intensity (MFI) in either CD4+ or CD8+Vα24+ population.
Figure 10:
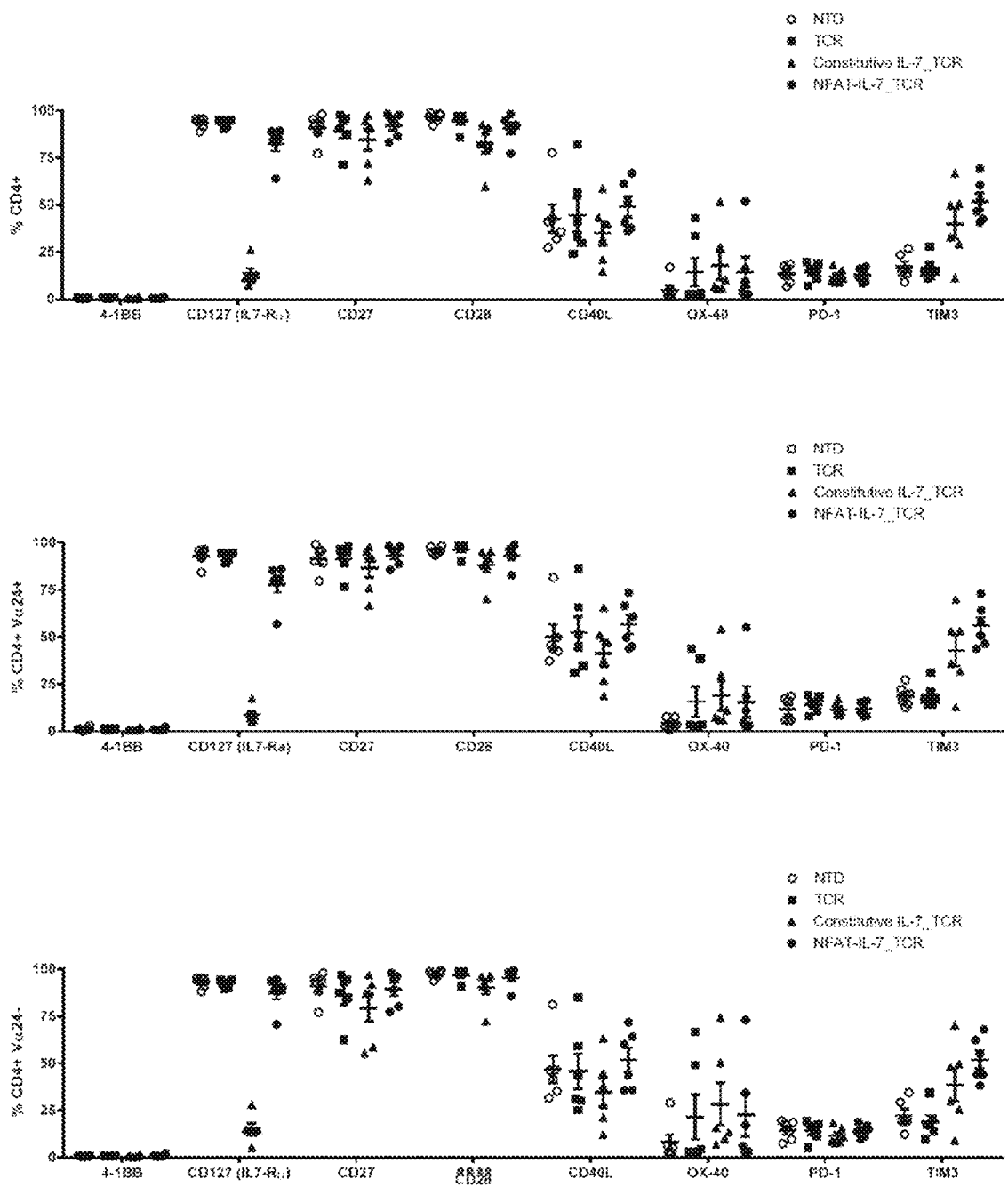
FIG. 10 shows an assessment of 4-1BB, CD127, CD27, CD28, CD40L, OX-40, PD-1 and TIM-3 expression on CD4+ T cells. NTD T cells (white circles), T cells transduced with TCR (black squares), constitutive IL-7_TCR (black triangles) or with NFAT_IL-7_TCR (black circles). Data shows mean+/−SD. The data are shown as the percentage of cells were either 4-1BB+, CD127+, CD27+, CD28+, CD40L+, OX-40+, PD-1+ or TIM-3+ and either (A) CD4+ (B) CD4+Vα24+ or (B) CD4+Vα24.
Figure 11:
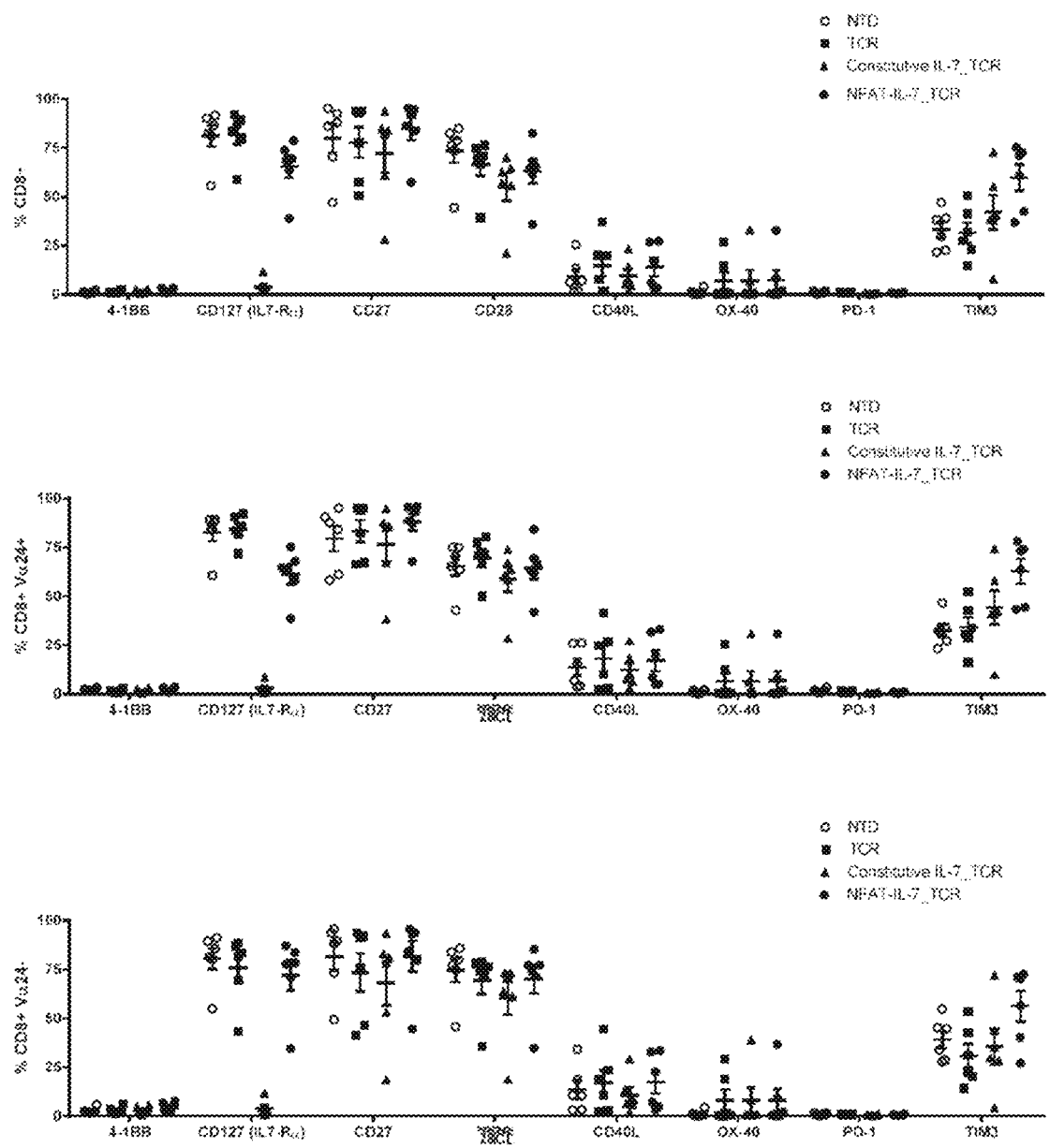
FIG. 11 shows an assessment of 4-1BB, CD127, CD27, CD28, CD40L, OX-40, PD-1 and TIM-3 expression on CD8+ T cells. NTD T cells (white circles), T cells transduced with MAGE-A4c1032 TCR (black squares), constitutive IL-7_MAGE-A4c1032 TCR (black triangles) or with NFAT_IL-7_MAGE-A4c1032TCR (black circles). Data shows mean+/−SD. The data are shown as the percentage of cells were either 41BB+, CD127+, CD27+, CD28+, CD40L+, OX-40+, PD-1+ or TIM-3+ and either (A) CD8+ (B) CD8+Vα24+ or (B) CD8+Vα24−.
Figure 12:
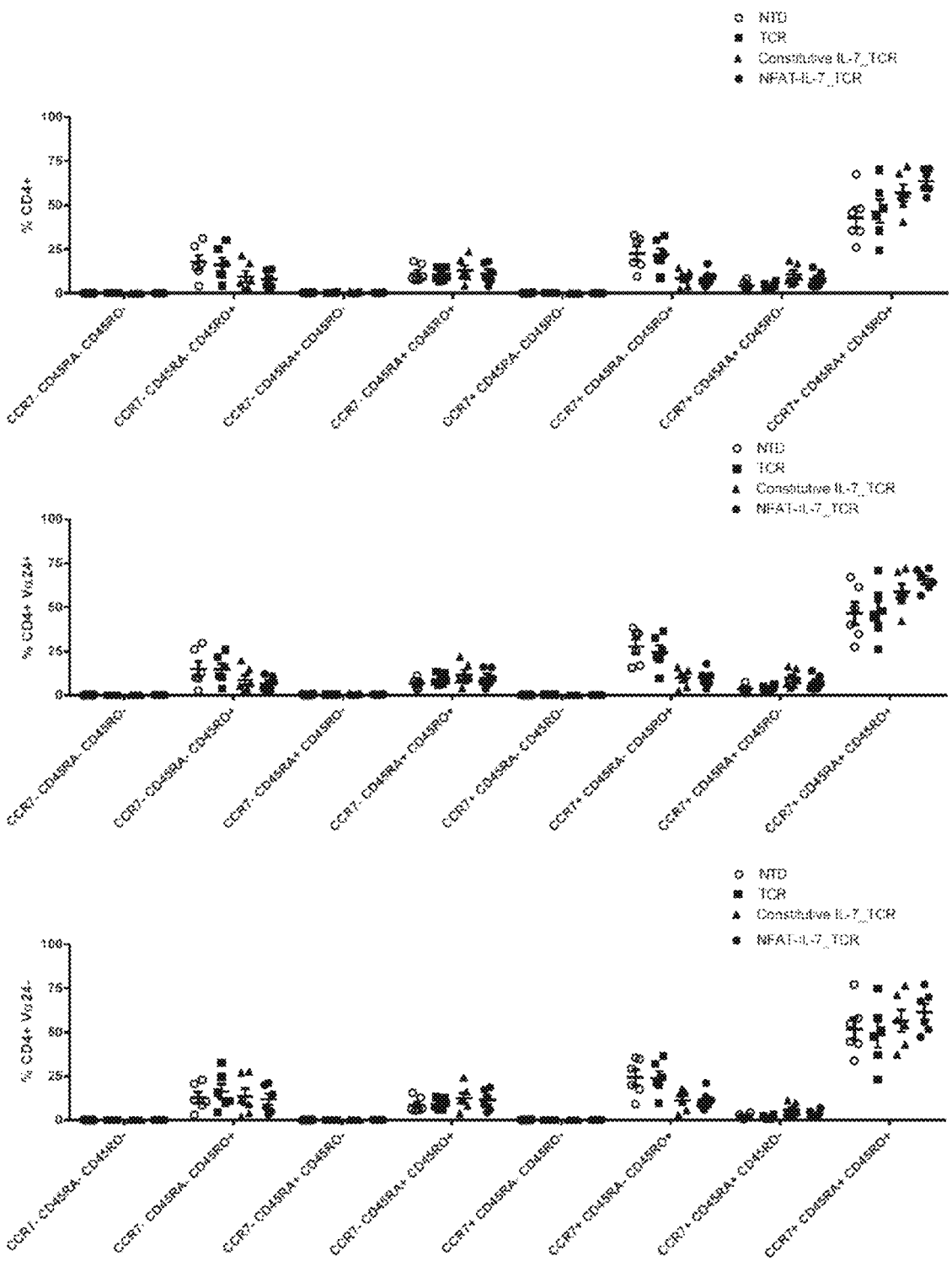
FIG. 12 shows an assessment of the proportions of naïve and memory CD4+ T cells. NTD T cells (white circles), T cells transduced with TCR (black squares), constitutive IL-7_TCR (black triangles) or with NFAT_IL-7_TCR (black circles). Data shows mean+/−SD. The data are shown as the percentage of cells were either CCR7− CD45RA− CD45RO−, CCR7− CD45RA− CD45RO+, CCR7− CD45RA+ CD45RO−, CCR7− CD45RA+ CD45RO+, CCR7+ CD45RA− CD45RO−, CCR7+CD45RA− CD45RO+, CCR7+CD45RA+CD45RO− or CCR7+ CD45RA+ CD45RO+ and either (A) CD4+(B) CD4+ Vα24+ or (B) CD4+Vα24−.
Figure 13:
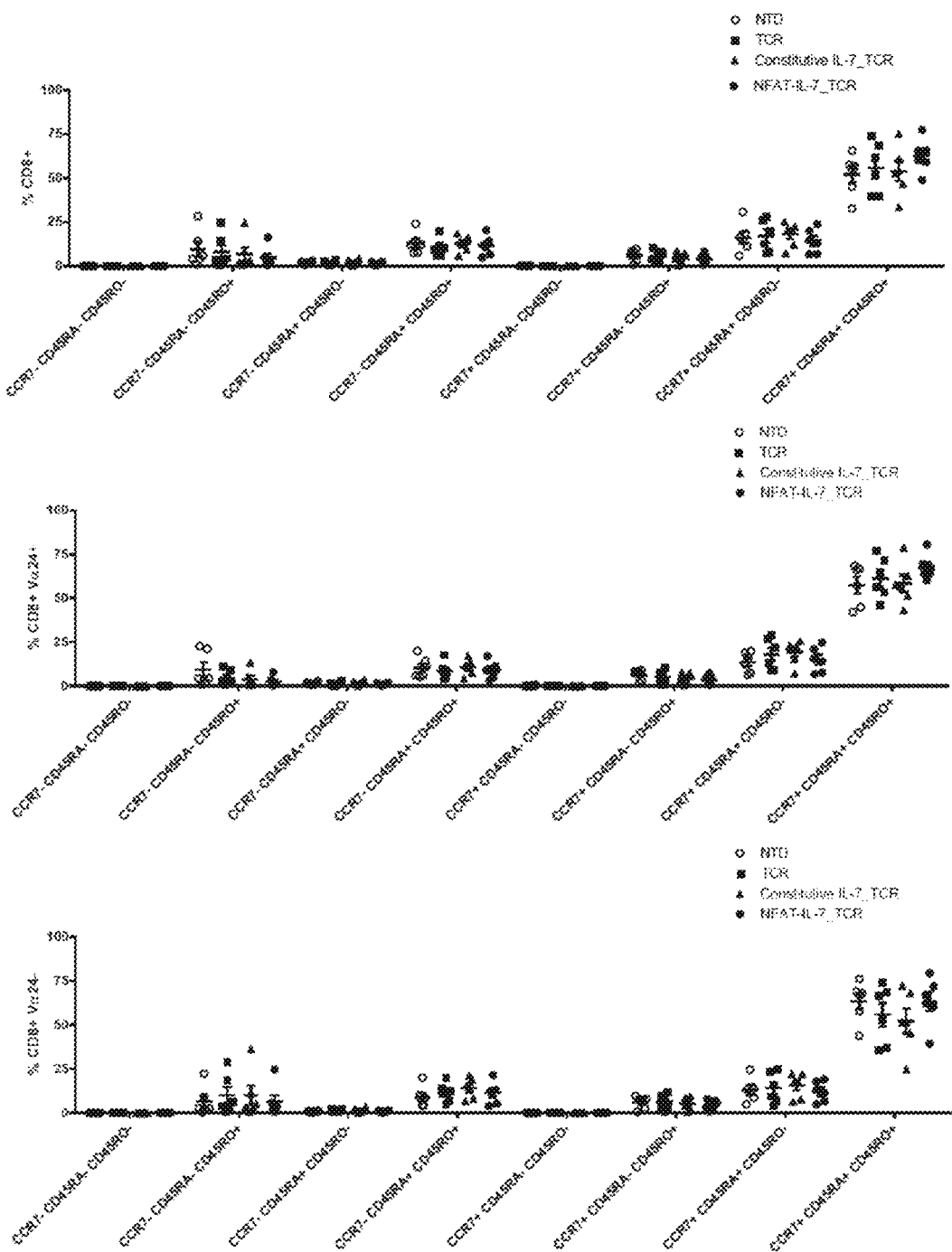
FIG. 13 shows an assessment of the proportions of naïve and memory CD8+ T cells. NTD T cells (white circles), T cells transduced with TCR (black squares), constitutive IL-7_TCR (black triangles) or with NFAT_IL-7_TCR (black circles). Data shows mean+/−SD. The data are shown as the percentage of cells were either CCR7− CD45RA− CD45RO−, CCR7− CD45RA− CD45RO+, CCR7− CD45RA+CD45RO−, CCR7− CD45RA+CD45RO+, CCR7+CD45RA− CD45RO−, CCR7+CD45RA− CD45RO+, CCR7+CD45RA+CD45RO− or CCR7+ CD45RA+ CD45RO+ and either (A) CD8+(B) CD8+ Vα24+ or (B) CD8+Vα24−.
Figure 14:
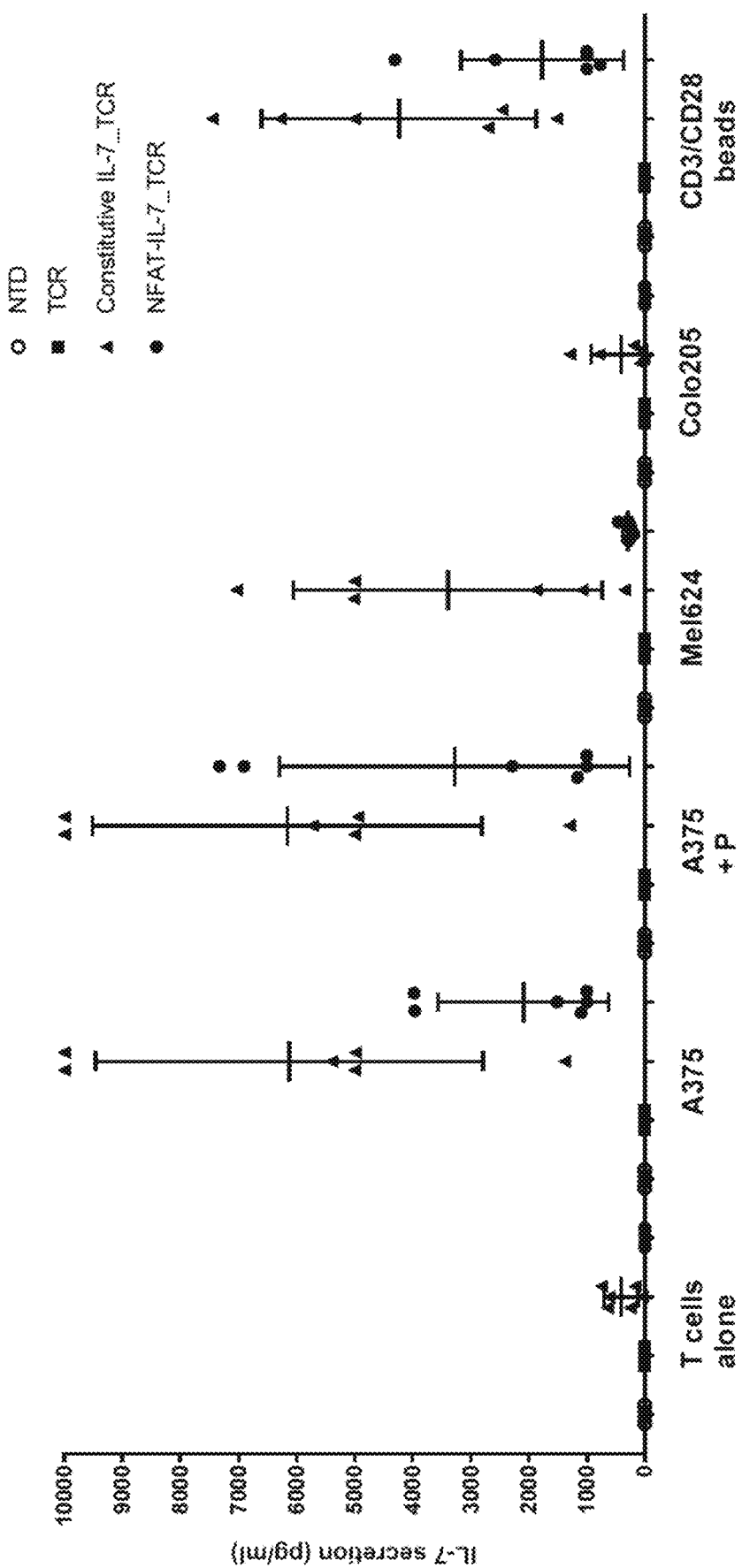
FIG. 14 shows IL-7 production by T cells in response to antigen positive and negative cells. NTD T cells (white circles), T cells transduced with TCR (black squares), constitutive IL-7_TCR (black triangles) or with NFAT_IL-7_TCR (black circles) were incubated 48 hours alone, or with A375, Mel624 or Colo205 cells. A375 cells pulsed with exogenous peptide or CD3/CD28 beads were included as controls. Data were from 6 donors. Supernatants from T cells were either diluted 1:5 of 1:10. The maximum concentration on the standard curve was 1000 pg/ml and as such any values>2000 pg/ml, 5000 pg/ml or 10.000 pg/ml were assigned a value of 2000 pg/ml, 5000 pg/ml or 10.000 pg/ml respectively. Data shows mean+/−SD of triplicate wells.
Figure 15:
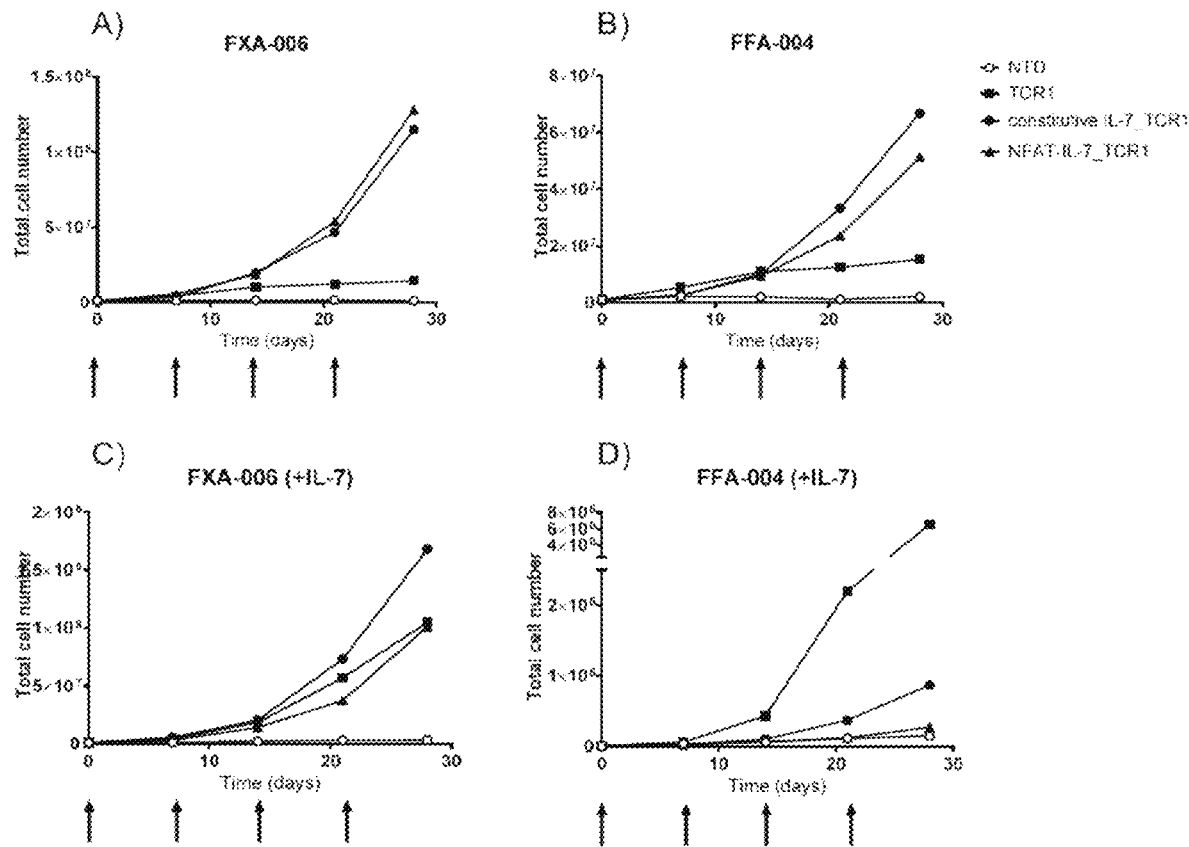
FIG. 15 shows total T cell counts from donors FXA-006 and FFA-004 in response to repeated stimulation with irradiated A375 cells (Assay ref. no.: ACF 1141). Total live cell counts (Trypan Blue negative cells) from co-cultures with NTD T cells (white circles), T cells transduced with TCR (black squares), constitutive IL-7_TCR (black triangles) or with NFAT_IL-7_TCR (black circles) that were restimulated weekly with irradiated A375 (HLA-A2+/NY-ESO+) cells in the presence or absence of 20 mg/ml IL-7. Restimulation was performed on days 0, 7, 14 and 21 and is indicated by the arrows. T cells were from donors (A) FXA-006 or (B) FFA-004 in the absence of IL-7 or from (C) FXA-006 or (D) FFA-004 in the presence of IL-7. The total cell count was assessed on days 7, 14, 21 and 28.

The IL-7 CDS was PCR amplified from ABD1099 with the following primers FWD-5' TAATGCTAGCGCCGC-CACCATGTTCCACGTGTCC 3' and Rev 5'-CTT-CACGGGCGCGCCAGAGCCGCTTCTCTTGG-3'. These include NheI (GCTAGC) and AscI (GGCGCGCC) restriction sites (underlined). PCR products were purified by gel extraction and purified by gel extraction using a Nucleo-Spin® gel extraction kit according to manufacturer's instruction. The PCR product and (ADB1488) were digested with NheI and AscI and fragments of interest purified by gel extraction using a NucleoSpin® gel extraction kit according to manufacturer's protocol. Digested fragments were ligated using T4 DNA ligase (NEB) according to standard protocols. Clones were screened by restriction enzyme digest and verified by sequencing (see the vector map of FIG. 7).

1.6 T Cell Production

PBLs from six donors were separated from whole blood with additional CD14 depletion (PBL) using MACS isolation kits and associated manufacturer's protocols. T cells were transduced with different lentiviral constructs including: TCR and NFAT_IL-7 TCR (see FIG. 1). T cell transductions were performed in the presence of 1 mg/ml F108 Poloxamer. The F108 Poloxamer had previously been dissolved in water to make a stock solution at 100 mg/ml and was then sterilised using a 0.2 m filter before storing at 4° C. 1 mg/ml F108 Poloxamer was added to each well of cells (including NTD cells) at the same time as addition of the lentiviral particles.

Transduced cells were expanded for 14 days. T cells were fed with 100 U/ml Proleukin on day 10 but fed with fresh media without Proleukin on day 12 to allow the cells more time to rest prior to use for assays, particularly for proliferation assays.

On day 14 cells were frozen. Non-transduced (NTD) T cells were produced at the same time as the transduced T cells but fresh virus medium (R10+Hepes) was added to the stimulated T cells in place of lentiviral particles.

1.7 Cytokine Secretion Assays for ELISA

Cytokine production assays were typically carried out as follows. On the day of the assay, A375, Mel624 and Colo205 cells were harvested, resuspended in R10 and counted. Some of the A375 cells were pulsed for 2 hours at 37° C./5% $CO_2$ with 10 M MAGE-A4 peptide, before washing three times. Target cells were typically plated out at 50,000 cells/well in a volume of 100 µl into 96 well flat bottom plates in triplicate wells. T cells were thawed, washed, resuspended in R10 at no less than $1\times10^6$ cells/ml and rested for 1-2 h at 37° C./5% $CO_2$. Non-transduced and transduced effector cells were counted and were plated at 120,000 cells per well in 100 µl assay medium, in triplicate wells, to give a final volume of 200 µl. Note: to account for differences in transduction between the different constructs, the cells were normalised by adding NTD T cells from the same donor to give equivalent transduction efficiencies. Plates were then put in the incubator at 37° C./5% $CO_2$ for 48 hours. After 48 hours, the assay plates were centrifuged and supernatant transferred to new 96 well plates, which were stored at −20° C. until analysis by ELISA which was performed at a later date.

1.8 IL-7 ELISA

This assay was performed in 96 well half area plates using the Duoset Human IL-7 ELISA kit according to the manufacturer's protocol with modifications. Briefly, as the 96 well half area plates were used, 25 µl/well (or 50 µl of blocking reagent) was used for all reagents instead of 100 µl as indicated in the protocol. In most cases the samples were used undiluted. If they were diluted they were diluted in assay medium. The assays were developed using commercial TMB substrate solution for approx. 10 minutes and the reaction stopped with 1N H2SO4. Assays were read using the Spectrastar Omega at 450 nm with wavelength correction set to 540 nm. Data were analysed using Spectrastar data analysis software. Data points greater than the top concentration on the standard curve were normally allocated the value of the top concentration. For most assays the standard curve was extended to provide a greater range than indicated by the manufacturer, with atop concentration of 1000 pg/ml. Samples and standard curves were either performed using duplicate or triplicate wells and the curve fitting was performed using four parameter logistic curve fitting where possible.

1.9 T Cell Phenotyping

On the day of the assay, the T cells were thawed, washed twice in PBS, counted and adjusted to $1\times10^6$ cells/ml in PBS. Flow cytometry was performed on T cells. The list of antibodies used can be found in Tables 1 and 2.

TABLE 1

List of antibodies and volumes used to identify proliferating
T cells at the end of the expansion phase (Panel 1)

| Antibody | Volume/test (µl) |
|---|---|
| CD45RA-PE Cy7 (BioLgend: 304126) | 1.25 µl |
| CD45RO-PerCP Cy5.5 (BioLegend: 304222) | 1.25 µl |
| CCR7-PE CF594 (BD Bioscience: 562381) | 5 µl |
| Vα24-PE (Beckman Coulter: IM2283) | 20 |
| PD-1-BV786 (BioLegend: 329929) | 2.5 µl |
| CD4-BV650 (BD Bioscience: 56875) | 2.5 µl |
| CD8-APC-ef780 (eBioscience: 47-0087-42) | 2.5 µl |
| CD3-FITC (eBioscience: 11-0036-42) | 2.5 µl |
| TIM-3-APC (R&D Systems: FAB2365A) | 5 µl |
| IL7Rα (CD127)-BV421 (BioLegend: 47-1278-42) | 5 µl |
| LIVE/DEAD ® Fixable Aqua Dead Cell Stain (Life Technologies: L34957) | 1/800 dilution |

TABLE 2

List of antibodies and volumes used to identify proliferating
T cells at the end of the expansion phase (Panel 2)

| Antibody | Volume/test (µl) |
|---|---|
| CD8-APC-ef780 (eBioscience: 47-0087-42) | 2.5 µl |
| CD4-BV650 (BD Bioscience: 56875) | 2.5 µl |
| CD45RA-PE Cy7 (BioLgend: 304126) | 1.25 µl |
| CCR7-PE CF594 (BD Bioscience: 562381) | 5 µl |
| Vα24-PE (Beckman Coulter: IM2283) | 20 |
| OX-40(CD134)-FITC (BD Bioscience: 555837) | 5 µl |
| CD40L (CD154)-BV421 (BD Bioscience: 563886) | 5 µl |
| CD28-PerCPCy5.5 (BD Bioscience: 560685) | 2.5 µl |
| CD27-BV786 (BD Bioscience: 563327) | 5 µl |
| 4-1BB-APC (BD Bioscience: 550890) | 2.5 µl |
| LIVE/DEAD ® Fixable Aqua Dead Cell Stain (Life Technologies: L34957) | 1/800 dilution |

1.10 Restimulation Assay

The restimulation assays were carried out as follows. On the first day of the assay (day 0) T cells were thawed, washed, resuspended in R10 at no less than $1\times10^6$ cells/ml and rested.

Cells were counted and in order to account for differences in transduction between the different lentiviral preparations, the cells were normalised by adding NTD T cells from the same donor to give equivalent transduction efficiencies within a batch of donor T cells.

T cells were plated out in R10 at $1\times10^6$/ml, with 1 ml of T cells per well in a 24 well plate. A375 target cells were harvested and then irradiated (48 Gy). A375 cells were resuspended at approximately $1\times10^6$/ml and 1 ml per well added to the wells containing T cells. This gave a final volume of 2 ml/well with 1:1 T cells and irradiated A375 cells. In control wells recombinant human IL-7 was added to the cells at a final concentration of 20 ng/ml. Co-cultures of T cells and irradiated A375 cells with or without exogenous IL-7 were then cultured for 7 days at 37° C./5% $CO_2$.

On days 7, 14, 21 and 28, T cells were harvested and counted using semi-automated counting with Trypan Blue positive cells (dead cells) excluded. For wells containing T cells that did not express the TCR1, not all the Trypan Blue-negative (live) cells were T cells, as they were much larger than T cells. These were most likely to be irradiated A375 targets that were not yet positive for Trypan Blue staining. As many as possible of the larger, obviously non-T cells (A375) were manually excluded from the counts but live T cell counts from those wells (containing NTD) are likely to be an overestimate as they still contained some "apparently" live A375 targets. This was also reflected by the larger average size of the cells from those samples as A375 cells are larger than T cells. However in wells containing T cells expressing the TCR1 there were few or no large, live A375 cells remaining, so absolute counts and cell sizes are likely to be more accurate. The total live T cell count was then calculated.

Once the total number of live T cells had been calculated, T cells were split as follows. If the T cells had proliferated, they were diluted to a concentration of $1\times10^6$/ml (to the nearest ml) by adding fresh R10 to the existing volume of T cells (in "old" R10) to the correct final concentration. "Old" R10 is defined as the media that the cells had been cultured in for the previous week. If however the T cells had contracted (i.e. the number of live T cells had reduced compared with the concentration originally plated out), cells were centrifuged (1500 rpm, 5 minutes) and then resuspended in the appropriate volume of "old" R10.

T cells were plated out at 1 ml/well (~$1\times10^6$ T cells/ml) in 24 well plates. Where possible, all the T cells were plated out as they expanded, so that the total number of T cells presented in the figures was actually the total number of T cells produced. In some instances, particularly at later time points as the number of T cells grew increasingly large (usually greater than $8\text{-}12\times10^6$ cells), only $8\text{-}12\times10^6$ T cells were plated out for restimulation. The total number of T cells for those samples at subsequent time-points was then re-calculated by factoring in the number of T cells that had been originally plated out at the previous time-point. For example, if we had counted $20\times10^6$ T cells on day 21, we would only plate out $8\times10^6$ of those cells on day 21 for restimulation. The total cell numbers on day 28, which would have been generated if we had plated out all 20×106 cells, would be re-calculated as follows:

1. Fold change in cell numbers=Cell count after restimulation (on day 28)/Cell number plated out for restimulation ($8\times10^6$ originally plated out on day 21)
2. Re-calculated total cell numbers on day 28=Fold change in cell numbers (between days 21-28)×total number of cells that were available for plating out on day 21 (e.g. $20\times10^6$)

A375 target cells were harvested and irradiated at 48 Gy to prevent their proliferation, and then added to the T cells at approximately $1\times10^6$/ml, 1 ml/well (1:1 T cell: A375) in R10. In control wells recombinant human IL-7 was added to the cells at a final concentration of 20 µg/ml (assuming that all the IL-7 had been "consumed" in the well). This restimulation process was repeated on days 7, 14 and 21.

1.11 In Vivo Studies

PBL from a Leukopak were depleted of CD14 using the methods previously described. T cells were transduced as previously described and expanded for 14 days before freezing. In addition to the NTD T cells and T cells transduced with constructs expressing TCR1, NFAT-IL-7_TCR1 or constitutive IL-7_TCR1, T cells were also transduced with a construct expressing NFAT-IL-7_irrelevant TCR.

On day 0, immunodeficient CIEA NOG (NOD.Cg-Prkdc$_{scid}$ Il2g$_{tmISug}$/JicTac) female mice aged 6-8 weeks were injected intravenously (i.v.) with $1\times10_6$ Mel624 tumour cells that had previously been transduced with a lentiviral construct expressing GFP/Luciferase. On day 6 post-tumour cell implantation, mice were imaged and randomised into 8 groups of 8 mice groups, based on luciferase signal strength so that each group had an equal mean total flux. On day 7, T cells were thawed and the frequency of transduced T cells between the different constructs was normalised using NTD T cells to ~42% TCR Vβ+/CD3+. Mice were then i.v. injected either with nothing (tumour only control) or with 2×10⁶ total T cells (NTD, TCR1, NFAT-IL-7_TCR1, Constitutive IL-7_TCR1, NFAT-IL-7_control TCR).

Animals were imaged using the Bruker In Vivo Xtreme imaging system on day 6 and then once weekly to measure disease burden and follow disease progression. At later stages in the study animals were imaged twice weekly. Prior to imaging, animals were injected i.p. with 150 mg/kg of luciferin (5 ml/kg) and anaesthetised with isoflurane. After the exposure an X-ray picture was taken to aid orientation and organ positioning. At the time of analysis, images were converted to photons/second/mm$^2$ (P/s/mm$^2$) which allows comparison of images acquired using different exposure times, the scale was adjusted and the bioluminescence image was superimposed upon the X-ray image. A region of interest was set to measure the bioluminescence signal from the whole animal. The size of the ROI was kept identical for all images. Mice were also weighed at least 3 times per week and were culled when either weight loss or poor condition indicated.

Results

Figure 16:
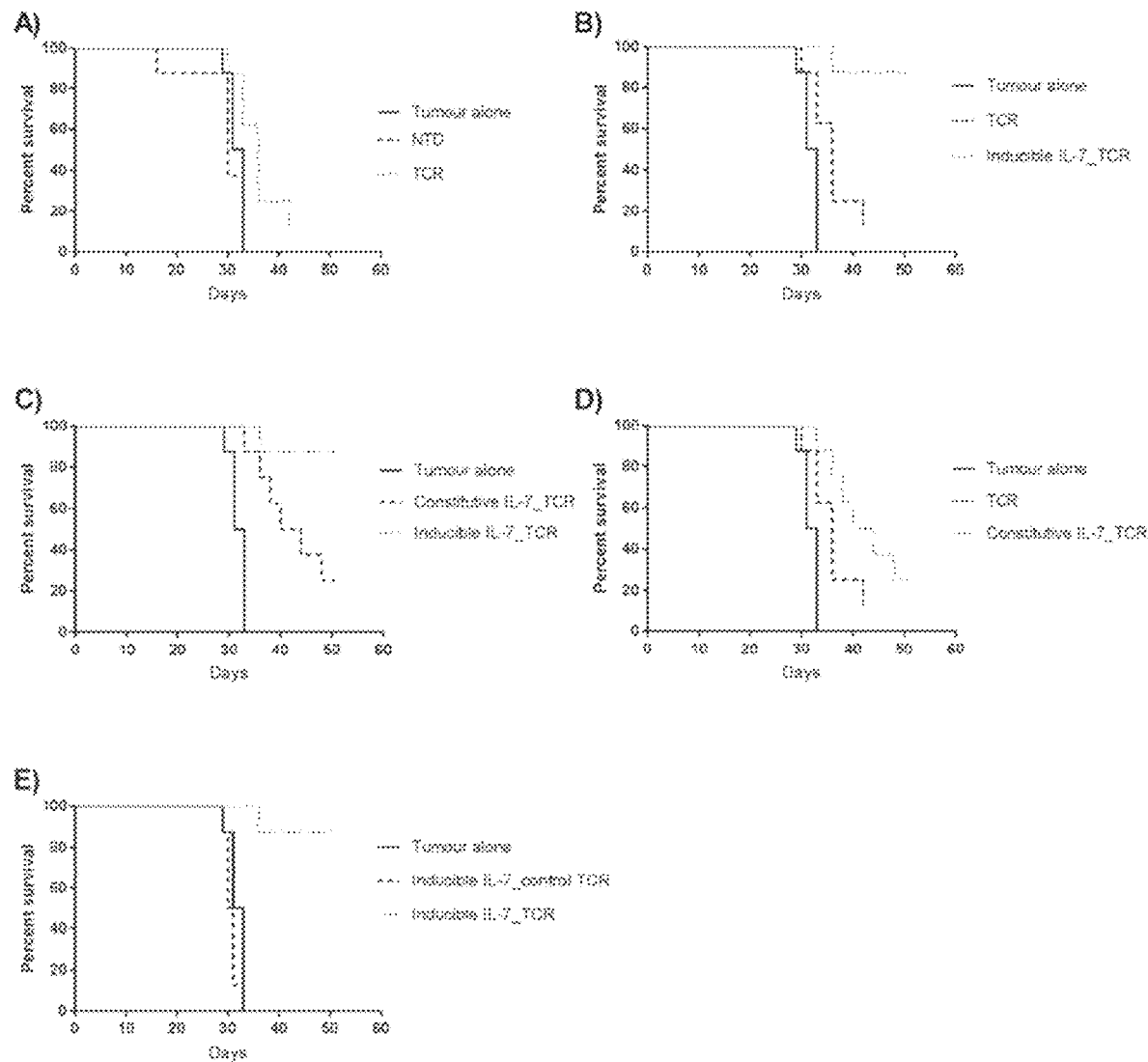
FIG. 16 shows that the survival of mice injected with T cells co-expressing inducible IL-7 with an engineered TCR compared with T cells expressing TCR alone or TCR together with constitutive IL-7. Survival curves are shown for mice injected i.v. with 1×10⁶ Mel624 tumour cells on day 0, followed by i.v. injection of 2×10⁶ total T cells on day 7 as indicated. The percentage of transduced T cells (TCR Vβ+/CD3+) were normalised to ~42% prior to injection using NTD T cells. Mice were culled as poor condition/weight loss required and the graphs indicate the percent survival of each group over the time of the study. (A-E) Percentage survival of mice injected with tumour alone (solid line) or the various T cells as indicated (dashed and dotted lines).

Mice injected with T cells co-expressing inducible IL-7 with an engineered TCR were found to show improved survival compared with cells expressing TCR alone or TCR together with constitutive IL-7 (FIG. 16).

Sequences:

Nucleotide sequence of the NFAT IL-7 inducible cassette.

SEQ ID NO: 1

ACCGGTTCAATTGCCGACCCCTCCCCCCAACTTCTCGGGGACTGTGGGCGATGTGCGCTCTGCCCACTGACGGGC

ACCGGAGCCTCACGATGCATGATATCGGCCTAACTGGCCGGTACCTGAGCTCGCTAGCGGAGGAAAAACTGTTTC

ATACAGAAGGCGTGGAGGAAAAACTGTTTCATACAGAAGGCGTGGAGGAAAAACTGTTTCATACAGAAGGCGTga cgtcTAGGCGTGTACGGTGGGAGGCCTATATAAGCAGAGCTCGTTTAGTGAACCGTCAGATCGCCTGGAGACGCC

ATCCACGCTGTTTTGACCTCCATAGAAGACACCGGGACCGATCCAGCCTCTCGACATTCGTTGGATCCATATGGC

CGCCACCATGTTCCATGTTTCTTTTAGGTATATCTTTGGACTTCCTCCCCTGATCCTTGTTCTGTTGCCAGTAGC

ATCATCTGATTGTGATATTGAAGGTAAAGATGGCAAACAATATGAGAGTGTTCTAATGGTCAGCATCGATCAATT

ATTGGACAGCATGAAAGAAATTGGTAGCAATTGCCTGAATAATGAATTTAACTTTTTTAAAAGACATATCTGTGA

TGCTAATAAGGAAGGTATGTTTTTATTCCGTGCTGCTCGCAAGTTGAGGCAATTTCTTAAAATGAATAGCACTGG

TGATTTTGATCTCCACTTATTAAAAGTTTCAGAAGGCACAACAATACTGTTGAACTGCACTGGCCAGGTTAAAGG

AAGAAAACCAGCTGCCCTGGGTGAAGCCCAACCAACAAAGAGTTTGGAAGAAAATAAATCTTTAAAGGAACAGAA

AAAACTGAATGACTTGTGTTTCCTAAAGAGACTATTACAAGAGATAAAAACTTGTTGGAATAAAATTTTGATGGG

CACTAAAGAACACTGACTCGAGAACTTGTTTATTGCAGCTTATAATGGTTACAAATAAAGCAATAGCATCACAAA

TTTCACAAATAAAGCATTTTTTTCACTGCATTCTACTTGTGGTTTGTCCAAACTCATCAATGTATCTTAACGCGT

Key:
Full underline = Tandem repeats of the human IL2 promoter NFAT TRE (GGAGGAAAAACTGTTTCATACAGAAGGCGT).
Dashed underline = Minimal CMV promoter.
No underline = The Kozak sequence (GCCGCCACCATG) and codon optimised IL-7 coding sequence.
Dotted underline = The SV40 polyadenylation signal.

Translated nucleotide sequence (SEQ ID NO: 2) and protein sequence (SEQ ID NO: 3) of codon optimised IL-7 atgttccatgtttcttttaggtatatctttggacttcctcccctgatccttgttctgttg

M  F  H  V  S  F  R  Y  I  F  G  L  P  P  L  I  L  V  L  L ccagtagcatcatctgattgtgatattgaaggtaaagatggcaaacaatatgagagtgtt

P  V  A  S  S  D  C  D  I  E  G  K  D  G  K  Q  Y  E  S  V ctaatggtcagcatcgatcaattattggacagcatgaaagaaattggtagcaattgcctg

L  M  V  S  I  D  Q  L  L  D  S  M  K  E  I  G  S  N  C  L aataatgaatttaacttttttaaaagacatatctgtgatgctaataaggaaggtatgttt Sequences:

```
  N   N   E   F   N   F   F   K   R   H   I   C   D   A   N   K   E   G   M   F
ttattccgtgctgctcgcaagttgaggcaatttcttaaaatgaatagcactggtgatttt
  L   F   R   A   A   R   K   L   R   Q   F   L   K   M   N   S   T   G   D   F
gatctccacttattaaaagtttcagaaggcacaacaatactgttgaactgcactggccag
  D   L   H   L   L   K   V   3   E   G   T   T   I   L   L   N   C   T   G   Q
gttaaaggaagaaaaccagctgccctgggtgaagcccaaccaacaaagagtttggaagaa
  V   K   G   R   K   P   A   A   L   G   E   A   Q   P   T   K   S   L   E   E
aataaatctttaaaggaacagaaaaaactgaatgacttgtgtttcctaaagagactatta
  N   K   S   L   K   E   Q   K   K   L   N   D   L   C   F   L   K   R   L   L
caagagataaaaacttgttggaataaaattttgatgggcactaaagaacactga
  Q   E   I   K   T   C   W   N   K   I   L   M   G   T   K   E   H   -
```

IL-7 protein sequence
SEQ ID NO: 3

MFHVSFRYIFGLPPLILVLLPVASSDCDIEGKDGKQYESVLMVSIDQLLDSMKEIGSNCLNNEFNFFK

RHICDANKEGMFLFRAARKLRQFLKMNSTGDFDLHLLKVSEGTTILLNCTGQVKGRKPAALGEAQPTK

SLEENKSLKEQKKLNDLCFLKRLLQEIKTCWNKILMGTKEH*

Nucleotide sequence between the NheI and SalI sites
SEQ ID NO: 4

ATGGAGACCCTGCTGGGCCTGCTGATCCTGTGGCTGCAGCTCCAGTGGGTGTCCAGCAAGCAGGAGGT

GACCCAGATCCCTGCCGCCCTGAGCGTGCCCGAGGGCGAGAACCTGGTGCTGAACTGCAGCTTCACCG

ACTCCGCCATCTACAACCTGCAGTGGTTCCGGCAGGACCCCGGCAAGGGCCTGACCAGCCTGCTGCTG

ATCCAGAGCAGCCAGCGGGAGCAGACCAGCGGACGGCTGAACGCCAGCCTGGACAAGAGCAGCGGCCG

GAGCACCCTGTACATCGCCGCCAGCCAGCCCGGCGACAGCGCCACCTACCTGTGCGCTGTGCGGCCTC

TGTACGGCGGCAGCTACATCCCCACCTTCGGCAGAGGCACCAGCCTGATCGTGCACCCCTACATCCAG

AACCCCGACCCCGCCGTGTACCAGCTGCGGGACAGCAAGAGCAGCGACAAGTCTGTGTGCCTGTTCAC

CGACTTCGACAGCCAGACCAATGTGAGCCAGAGCAAGGACAGCGACGTGTACATCACCGACAAGACCG

TGCTGGACATGCGGAGCATGGACTTCAAGAGCAACAGCGCCGTGGCCTGGAGCAACAAGAGCGACTTC

GCCTGCGCCAACGCCTTCAACAACAGCATTATCCCCGAGGACACCTTCTTCCCCAGCCCCGAGAGCAG

CTGCGACGTGAAACTGGTGGAGAAGAGCTTCGAGACCGACACCAACCTGAACTTCCAGAACCTGAGCG

TGATCGGCTTCAGAATCCTGCTGCTGAAGGTGGCCGGATTCAACCTGCTGATGACCCTGCGGCTGTGG

AGCAGCGGCTCCCGGGCCAAGAGAAGCGGATCCGGCGCCACCAACTTCAGCCTGCTGAAGCAGGCCGG

AGACGTGGAAGAAAACCCTGGCCCTAGGATGAGCATCGGCCTGCTGTGCTGCGCCGCCCTGAGCCTGC

TGTGGGCAGGACCCGTGAACGCCGGAGTGACCCAGACCCCCAAGTTCCAGGTGCTGAAAACCGGCCAG

AGCATGACCCTGCAGTGCGCCCAGGACATGAACCACGAGTACATGAGCTGGTATCGGCAGGACCCCGG

CATGGGCCTGCGGCTGATCCACTACTCTGTGGGAGCCGGAATCACCGACCAGGGCGAGGTGCCCAACG

GCTACAATGTGAGCCGGAGCACCACCGAGGACTTCCCCCTGCGGCTGCTGAGCGCTGCCCCCAGCCAG

ACCAGCGTGTACTTCTGCGCCAGCAGCTATGTGGGCAACACCGGCGAGCTGTTCTTCGGCGAGGGCTC

CAGGCTGACCGTGCTGGAGGACCTGAAGAACGTGTTCCCCCCCGAGGTGGCCGTGTTCGAGCCCAGCG

AGGCCGAGATCAGCCACACCCAGAAGGCCACACTGGTGTGTCTGGCCACCGGCTTCTACCCCGACCAC

GTGGAGCTGTCCTGGTGGGTGAACGGCAAGGAGGTGCACAGCGGCGTGTCTACCGACCCCCAGCCCCT

GAAGGAGCAGCCCGCCCTGAACGACAGCCGGTACTGCCTGTCCTCCAGACTGAGAGTGAGCGCCACCT

| Sequences: | |
|---|---|
| TCTGGCAGAACCCCCGGAACCACTTCCGGTGCCAGGTGCAGTTCTACGGCCTGAGCGAGAACGACGAG<br>TGGACCCAGGACCGGGCCAAGCCCGTGACCCAGATTGTGAGCGCCGAGGCCTGGGGCAGGGCCGACTG<br>CGGCTTCACCAGCGAGAGCTACCAGCAGGGCGTGCTGAGCGCCACCATCCTGTACGAGATCCTGCTGG<br>GCAAGGCCACCCTGTACGCCGTGCTGGTGTCTGCCCTGGTGCTGATGGCTATGGTGAAGCGGAAGGAC<br>AGCCGGGGCTAAGTCGAC | |
| Protein sequence of TCR1 | SEQ ID NO: 5 |
| METLLGLLILWLQLQWVSSKQEVTQIPAALSVPEGENLVLNCSFTDSAIYNLQWFRQDPGKGLTSLLL<br>IQSSQREQTSGRLNASLDKSSGRSTLYIAASQPGDSATYLCAVRPLYGGSYIPTFGRGTSLIVHPYIQ<br>NPDDPAVYQLRDSKSSDKSVCLFTDFDSQTNVSQSKDSDVYITDKTVLDMRSMDFKSNSAVAWSNKSDF<br>ACANAFNNSIIPEDTFFPSPESSCDVKLVEKSFETDTNLNFQNLSVIGFRILLLKVAGFNLLMTLRLW<br>SSGSRAKRSGSGATNFSLLKQAGDVEENPGPRMSIGLLCCAALSLLWAGPVNAGVTQTPKFQVLKTGQ<br>SMTLQCAQDMNHEYMSWYRQDPGMGLRLIHYSVGAGITDQGEVPNGYNVSRSTTEDFPLRLLSAAPSQ<br>TSVYFCASSYVGNTGELFFGEGSRLTVLEDLKNVFPPEVAVFEPSEAEISHTQKATLVCLATGFYPDH<br>VELSWWVNGKEVHSGVSTDPQPLKEQPALNDSRYCLSSRLRVSATFWQNPRNHFRCQVQFYGLSENDE<br>WTQDRAKPVTQIVSAEAWGRADCGFTSESYQQGVLSATILYEILLGKATLYAVLVSALVLMAMVKRKD<br>SRG*V | |
| TCR1 CDS | SEQ ID NO: 6 |
| METLLGLLILWLQLQWVSSKQEVTQIPAALSVPEGENLVLNCSFTDSAIYNLQWFRQDPGKGLTSLLL<br>IQSSQREQTSGRLNASLDKSSGRSTLYIAASQPGDSATYLCAVRPLYGGSYIPTFGRGTSLIVHPYIQ<br>NPDDPAVYQLRDSKSSDKSVCLFTDFDSQTNVSQSKDSDVYITDKTVLDMRSMDFKSNSAVAWSNKSDF<br>ACANAFNNSIIPEDTFFPSPESSCDVKLVEKSFETDTNLNFQNLSVIGFRILLLKVAGFNLLMTLRLW<br>SSGSRAKRSGSGATNFSLLKQAGDVEENPGPRMSIGLLCCAALSLLWAGPVNAGVTQTPKFQVLKTGQ<br>SMTLQCAQDMNHEYMSWYRQDPGMGLRLIHYSVGAGITDQGEVPNGYNVSRSTTEDFPLRLLSAAPSQ<br>TSVYFCASSYVGNTGELFFGEGSRLTVLEDLKNVFPPEVAVFEPSEAEISHTQKATLVCLATGFYPDH<br>VELSWWVNGKEVHSGVSTDPQPLKEQPALNDSRYCLSSRLRVSATFWQNPRNHFRCQVQFYGLSENDE<br>WTQDRAKPVTQIVSAEAWGRADCGFTSESYQQGVLSATILYEILLGKATLYAVLVSALVLMAMVKRKD<br>SRG | |
| Sense strand 5' to 3' sequence spanning the region between the MluI<br>and SalI restriction sites. | SEQ ID NO: 7 |
| ACGCGTTAAGATACATTGATGAGTTTGGACAAACCACAACTAGAATGCAGTGAAAAAAATGCTTTATT<br>TGTGAAATTTGTGATGCTATTGCTTTATTTGTAACCATTATAAGCTGCAATAAACAAGTTCTCGAGTC<br>AGTGCTCTTTGGTGCCCATCAGGATCTTGTTCCAGCAGGTCTTGATTTCCTGCAGCAGCCGCTTCAGG<br>AAGCACAGGTCGTTCAGTTTCTTCTGCTCTTTCAGGGACTTGTTCTCTTCCAGGCTCTTGGTAGGCTG<br>GGCTTCTCCCAGGGCGGCAGGCTTTCTGCCCTTCACTTGGCCGGTGCAATTCAGCAGGATGGTGGTGC<br>CCTCGGACACTTTCAGCAGATGCAGGTCGAAGTCGCCGGTGCTGTTCATCTTCAGGAACTGCCGCAGC<br>TTTCTGGCGGCTCTGAACAGGAACATGCCTTCTTTGTTGGCGTCGCAGATGTGCCGCTTGAAGAAGTT<br>GAACTCGTTGTTCAGGCAGTTGCTGCCGATTTCCTTCATGCTGTCCAGCAGCTGGTCGATGGACACCA<br>TCAGCACGCTCTCGTACTGCTTGCCGTCCTTGCCCTCGATGTCGCAGTCGCTGCTGGCCACAGGCAGC<br>AGCACCAGGATCAGGGGGGGCAGGCCGAAGATGTACCGGAAGGACACGTGGAACATGGTGGCGGCCAT | |

| Sequences: |
|---|
| ATGGATCCAACGAATGTCGAGAGGCTGGATCGGTCCCGGTGTCTTCTATGGAGGTCAAAACAGCGTGG |
| ATGGCGTCTCCAGGCGATCTGACGGTTCACTAAACGAGCTCTGCTTATATAGGCCTCCCACCGTACAC |
| GCCTAGACGTCACGCCTTCTGTATGAAACAGTTTTTCCTCCACGCCTTCTGTATGAAACAGTTTTTCC |
| TCCACGCCTTCTGTATGAAACAGTTTTTCCTCCGCTAGCGAGCTCAGGTACCGGCCAGTTAGGCCGAT |
| ATCATGCATCGTGAGGCTCCGGTGCCCGTCAGTGGGCAGAGCGCACATCGCCCACAGTCCCCGAGAAG |
| TTGGGGGGAGGGGTCGGCAATTGAACCGGTGCCTAGAGAAGGTGGCGCGGGGTAAACTGGGAAAGTGA |
| TGTCGTGTACTGGCTCCGCCTTTTTCCCGAGGGTGGGGGAGAACCGTATATAAGTGCAGTAGTCGCCG |
| TGAACGTTCTTTTTCGCAACGGGTTTGCCGCCAGAACACAGGTAAGTGCCGTGTGTGGTTCCCGCGGG |
| CCTGGCCTCTTTACGGGTTATGGCCCTTGCGTGCCTTGAATTACTTCCACCTGGCTGCAGTACGTGAT |
| TCTTGATCCCGAGCTTCGGGTTGGAAGTGGGTGGGAGAGTTCGAGGCCTTGCGCTTAAGGAGCCCCTT |
| CGCCTCGTGCTTGAGTTGAGGCCTGGCCTGGGCGCTGGGGCCGCCGCGTGCGAATCTGGTGGCACCTT |
| CGCGCCTGTCTCGCTGCTTTCGATAAGTCTCTAGCCATTTAAAATTTTTGATGACCTGCTGCGACGCT |
| TTTTTTCTGGCAAGATAGTCTTGTAAATGCGGGCCAAGATCTGCACACTGGTATTTCGGTTTTTGGGG |
| CCGCGGGCGGCGACGGGCCCGTGCGTCCCAGCGCACATGTTCGGCGAGGCGGGGCCTGCGAGCGCGG |
| CCACCGAGAATCGGACGGGGGTAGTCTCAAGCTGGCCGGCCTGCTCTGGTGCCTGGCCTCGCGCCGCC |
| GTGTATCGCCCCGCCCTGGGCGGCAAGGCTGGCCCGGTCGGCACCAGTTGCGTGAGCGGAAAGATGGC |
| CGCTTCCCGGCCCTGCTGCAGGGAGCTCAAAATGGAGGACGCGGCGCTCGGGAGAGCGGGCGGGTGAG |
| TCACCCACACAAAGGAAAAGGGCCTTTCCGTCCTCAGCCGTCGCTTCATGTGACTCCACTGAGTACCG |
| GGCGCCGTCCAGGCACCTCGATTAGTTCTCGTGCTTTTGGAGTACGTCGTCTTTAGGTTGGGGGAGG |
| GGTTTTATGCGATGGAGTTTCCCCACACTGAGTGGGTGGAGACTGAAGTTAGGCCAGCTTGGCACTTG |
| ATGTAATTCTCCTTGGAATTTGCCCTTTTTGAGTTTGGATCTTGGTTCATTCTCAAGCCTCAGACAGT |
| GGTTCAAAGTTTTTTTCTTCCATTTCAGGTGTCGTGAGCTAGCCGCCACCATGGAGACCCTGCTGGGC |
| CTGCTGATCCTGTGGCTGCAGCTCCAGTGGGTGTCCAGCAAGCAGGAGGTGACCCAGATCCCTGCCGC |
| CCTGAGCGTGCCCGAGGGCGAGAACCTGGTGCTGAACTGCAGCTTCACCGACTCCGCCATCTACAACC |
| TGCAGTGGTTCCGGCAGGACCCCGGCAAGGGCCTGACCAGCCTGCTGCTGATCCAGAGCAGCCAGCGG |
| GAGCAGACCAGCGGACGGCTGAACGCCAGCCTGGACAAGAGCAGCGGCCGGAGCACCCTGTACATCGC |
| CGCCAGCCAGCCCGGCGACAGCGCCACCTACCTGTGCGCTGTGCGGCCTCTGTACGGCGGCAGCTACA |
| TCCCCACCTTCGGCAGAGGCACCAGCCTGATCGTGCACCCCTACATCCAGAACCCCGACCCCGCCGTG |
| TACCAGCTGCGGGACAGCAAGAGCAGCGACAAGTCTGTGTGCCTGTTCACCGACTTCGACAGCCAGAC |
| CAATGTGAGCCAGAGCAAGGACAGCGACGTGTACATCACCGACAAGACCGTGCTGGACATGCGGAGCA |
| TGGACTTCAAGAGCAACAGCGCCGTGGCCTGGAGCAACAAGAGCGACTTCGCCTGCGCCAACGCCTTC |
| AACAACAGCATTATCCCCGAGGACACCTTCTTCCCCAGCCCCGAGAGCAGCTGCGACGTGAAACTGGT |
| GGAGAAGAGCTTCGAGACCGACACCAACCTGAACTTCCAGAACCTGAGCGTGATCGGCTTCAGAATCC |
| TGCTGCTGAAGGTGGCCGGATTCAACCTGCTGATGACCCTGCGGCTGTGGAGCAGCGGCTCCCGGGCC |
| AAGAGAAGCGGATCCGGCGCCACCAACTTCAGCCTGCTGAAGCAGGCCGGAGACGTGGAAGAAAACCC |
| TGGCCCTAGGATGAGCATCGGCCTGCTGTGCTGCGCCGCCCTGAGCCTGCTGTGGGCAGGACCCGTGA |
| ACGCCGGAGTGACCCAGACCCCCAAGTTCCAGGTGCTGAAAACCGGCCAGAGCATGACCCTGCAGTGC |
| GCCCAGGACATGAACCACGAGTACATGAGCTGGTATCGGCAGGACCCCGGCATGGGCCTGCGGCTGAT |

| Sequences: |
|---|
| CCACTACTCTGTGGGAGCCGGAATCACCGACCAGGGCGAGGTGCCCAACGGCTACAATGTGAGCCGGA |
| GCACCACCGAGGACTTCCCCCTGCGGCTGCTGAGCGCTGCCCCCAGCCAGACCAGCGTGTACTTCTGC |
| GCCAGCAGCTATGTGGGCAACACCGGCGAGCTGTTCTTCGGCGAGGGCTCCAGGCTGACCGTGCTGGA |
| GGACCTGAAGAACGTGTTCCCCCCCGAGGTGGCCGTGTTCGAGCCCAGCGAGGCCGAGATCAGCCACA |
| CCCAGAAGGCCACACTGGTGTGTCTGGCCACCGGCTTCTACCCCGACCACGTGGAGCTGTCCTGGTGG |
| GTGAACGGCAAGGAGGTGCACAGCGGCGTGTCTACCGACCCCCAGCCCCTGAAGGAGCAGCCCGCCCT |
| GAACGACAGCCGGTACTGCCTGTCCTCCAGACTGAGAGTGAGCGCCACCTTCTGGCAGAACCCCCGGA |
| ACCACTTCCGGTGCCAGGTGCAGTTCTACGGCCTGAGCGAGAACGACGAGTGGACCCAGGACCGGGCC |
| AAGCCCGTGACCCAGATTGTGAGCGCCGAGGCCTGGGGCAGGGCCGACTGCGGCTTCACCAGCGAGAG |
| CTACCAGCAGGGCGTGCTGAGCGCCACCATCCTGTACGAGATCCTGCTGGGCAAGGCCACCCTGTACG |
| CCGTGCTGGTGTCTGCCCTGGTGCTGATGGCTATGGTGAAGCGGAAGGACAGCCGGGGCTAA<u>GTCGAC</u> |

Nucleotide sequence of Constitutive-IL-7_T2A_TCR1. This sequence covers
the region between the NheI and SalI restriction sites.

SEQ ID NO: 8

| |
|---|
| <u>GCTAGC</u>GCCGCCACCATGTTCCACGTGTCCTTCCGGTACATCTTCGGCCTGCCCCCCCTGATCCTGGT |
| GCTGCTGCCTGTGGCCAGCAGCGACTGCGACATCGAGGGCAAGGACGGCAAGCAGTACGAGAGCGTGC |
| TGATGGTGTCCATCGACCAGCTGCTGGACAGCATGAAGGAAATCGGCAGCAACTGCCTGAACAACGAG |
| TTCAACTTCTTCAAGCGGCACATCTGCGACGCCAACAAAGAAGGCATGTTCCTGTTCAGAGCCGCCAG |
| AAAGCTGCGGCAGTTCCTGAAGATGAACAGCACCGGCGACTTCGACCTGCATCTGCTGAAAGTGTCCG |
| AGGGCACCACCATCCTGCTGAATTGCACCGGCCAAGTGAAGGGCAGAAAGCCTGCCGCCCTGGGAGAA |
| GCCCAGCCTACCAAGAGCCTGGAAGAGAACAAGTCCCTGAAAGAGCAGAAGAAACTGAACGACCTGTG |
| CTTCCTGAAGCGGCTGCTGCAGGAAATCAAGACCTGCTGGAACAAGATCCTGATGGGCACCAAAGAGC |
| ACGGAAGCAGAGCCAAGAGAAGCGGCTCTGGCGAGGGCAGAGGCAGCCTGCTGACATGTGGCGACGTG |
| GAAGAAAACCCTGGCCCTATGGAGACCCTGCTGGGCCTGCTGATCCTGTGGCTGCAGCTCCAGTGGGT |
| GTCCAGCAAGCAGGAGGTGACCCAGATCCCTGCCGCCCTGAGCGTGCCCGAGGGCGAGAACCTGGTGC |
| TGAACTGCAGCTTCACCGACTCCGCCATCTACAACCTGCAGTGGTTCCGGCAGGACCCCGGCAAGGGC |
| CTGACCAGCCTGCTGCTGATCCAGAGCAGCCAGCGGGAGCAGACCAGCGGACGGCTGAACGCCAGCCT |
| GGACAAGAGCAGCGGCCGGAGCACCCTGTACATCGCCGCCAGCCAGCCCGGCGACAGCGCCACCTACC |
| TGTGCGCTGTGCGGCCTCTGTACGGCGGCAGCTACATCCCCACCTTCGGCAGAGGCACCAGCCTGATC |
| GTGCACCCCTACATCCAGAACCCCGACCCCGCCGTGTACCAGCTGCGGGACAGCAAGAGCAGCGACAA |
| GTCTGTGTGCCTGTTCACCGACTTCGACAGCCAGACCAATGTGAGCCAGAGCAAGGACAGCGACGTGT |
| ACATCACCGACAAGACCGTGCTGGACATGCGGAGCATGGACTTCAAGAGCAACAGCGCCGTGGCCTGG |
| AGCAACAAGAGCGACTTCGCCTGCGCCAACGCCTTCAACAACAGCATTATCCCCGAGGACACCTTCTT |
| CCCCAGCCCCGAGAGCAGCTGCGACGTGAAACTGGTGGAGAAGAGCTTCGAGACCGACACCAACCTGA |
| ACTTCCAGAACCTGAGCGTGATCGGCTTCAGAATCCTGCTGCTGAAGGTGGCCGGATTCAACCTGCTG |
| ATGACCCTGCGGCTGTGGAGCAGCGGCTCCCGGGCCAAGAGAAGCGGATCCGGCGCCACCAACTTCAG |
| CCTGCTGAAGCAGGCCGGAGACGTGGAAGAAAACCCTGGCCCTAGGATGAGCATCGGCCTGCTGTGCT |
| GCGCCGCCCTGAGCCTGCTGTGGGCAGGACCCGTGAACGCCGGAGTGACCCAGACCCCCAAGTTCCAG |
| GTGCTGAAAACCGGCCAGAGCATGACCCTGCAGTGCGCCCAGGACATGAACCACGAGTACATGAGCTG |
| GTATCGGCAGGACCCCGGCATGGGCCTGCGGCTGATCCACTACTCTGTGGGAGCCGGAATCACCGACC |

-continued

Sequences:

AGGGCGAGGTGCCCAACGGCTACAATGTGAGCCGGAGCACCACCGAGGACTTCCCCCTGCGGCTGCTG
AGCGCTGCCCCCAGCCAGACCAGCGTGTACTTCTGCGCCAGCAGCTATGTGGGCAACACCGGCGAGCT
GTTCTTCGGCGAGGGCTCCAGGCTGACCGTGCTGGAGGACCTGAAGAACGTGTTCCCCCCCGAGGTGG
CCGTGTTCGAGCCCAGCGAGGCCGAGATCAGCCACACCCAGAAGGCCACACTGGTGTGTCTGGCCACC
GGCTTCTACCCCGACCACGTGGAGCTGTCCTGGTGGGTGAACGGCAAGGAGGTGCACAGCGGCGTGTC
TACCGACCCCCAGCCCCTGAAGGAGCAGCCCGCCCTGAACGACAGCCGGTACTGCCTGTCCTCCAGAC
TGAGAGTGAGCGCCACCTTCTGGCAGAACCCCCGGAACCACTTCCGGTGCCAGGTGCAGTTCTACGGC
CTGAGCGAGAACGACGAGTGGACCCAGGACCGGGCCAAGCCCGTGACCCAGATTGTGAGCGCCGAGGC
CTGGGGCAGGGCCGACTGCGGCTTCACCAGCGAGAGCTACCAGCAGGGCGTGCTGAGCGCCACCATCC
TGTACGAGATCCTGCTGGGCAAGGCCACCCTGTACGCCGTGCTGGTGTCTGCCCTGGTGCTGATGGCT
ATGGTGAAGCGGAAGGACAGCCGGGGCTAAGTCGAC

Protein sequence of constitutive IL-7_TCR1 IL7 is underlined, TCR is italicised.

SEQ ID NO: 9

<u>MFHVSFRYIFGLPPLILVLLPVASSDCDIEGKDGKQYESVLMVSIDQLLDSMKEIGSNCLNNEFNFFK</u>
<u>RHICDANKEGMFLFRAARKLRQFLKMNSTGDFDLHLLKVSEGTTILLNCTGQVKGRKPAALGEAQPTK</u>
<u>SLEENKSLKEQKKLNDLCFLKRLLQEIKTCWNKILMGTKEH</u>GSRAKRSGSGEGRGS*LLTCGDVEENPG*
*PMETLLGLLILWLQLQWVSSKQEVTQIPAALSVPEGENLVLNCSFTDSAIYNLQWFRQDPGKGLTSLL*
*LIQSSQREQTSGRLNASLDKSSGRSTLYIAASQPGDSATYLCAVRPLYGGSYIPTFGRGTSLIVHPYI*
*QNPDPAVYQLRDSKSSDKSVCLFTDFDSQTNVSQSKDSDVYITDKTVLDMRSMDFKSNSAVAWSNKSD*
*FACANAFNNSIIPEDTFFPSPESSCDVKLVEKSFETDTNLNFQNLSVIGFRILLLKVAGFNLLMTLRL*
*WSSGSRAKRSGSGATNFSLLKQAGDVEENPGPRMSIGLLCCAALSLLWAGPVNAGVTQTPKFQVLKTG*
*QSMTLQCAQDMNHEYMSWYRQDPGMGLRLIHYSVGAGITDQGEVPNGYNVSRSTTEDFPLRLLSAAPS*
*QTSVYFCASSYVGNTGELFFGEGSRLTVLEDLKNVFPPEVAVFEPSEAEISHTQKATLVCLATGFYPD*
*HVELSWWVNGKEVHSGVSTDPQPLKEQPALNDSRYCLSSRLRVSATFWQNPRNHFRCQVQFYGLSEND*
*EWTQDRAKPVTQIVSAEAWGRADCGFTSESYQQGVLSATILYEILLGKATLYAVLVSALVLMAMVKRK*
*DSRG*

Figure 6:
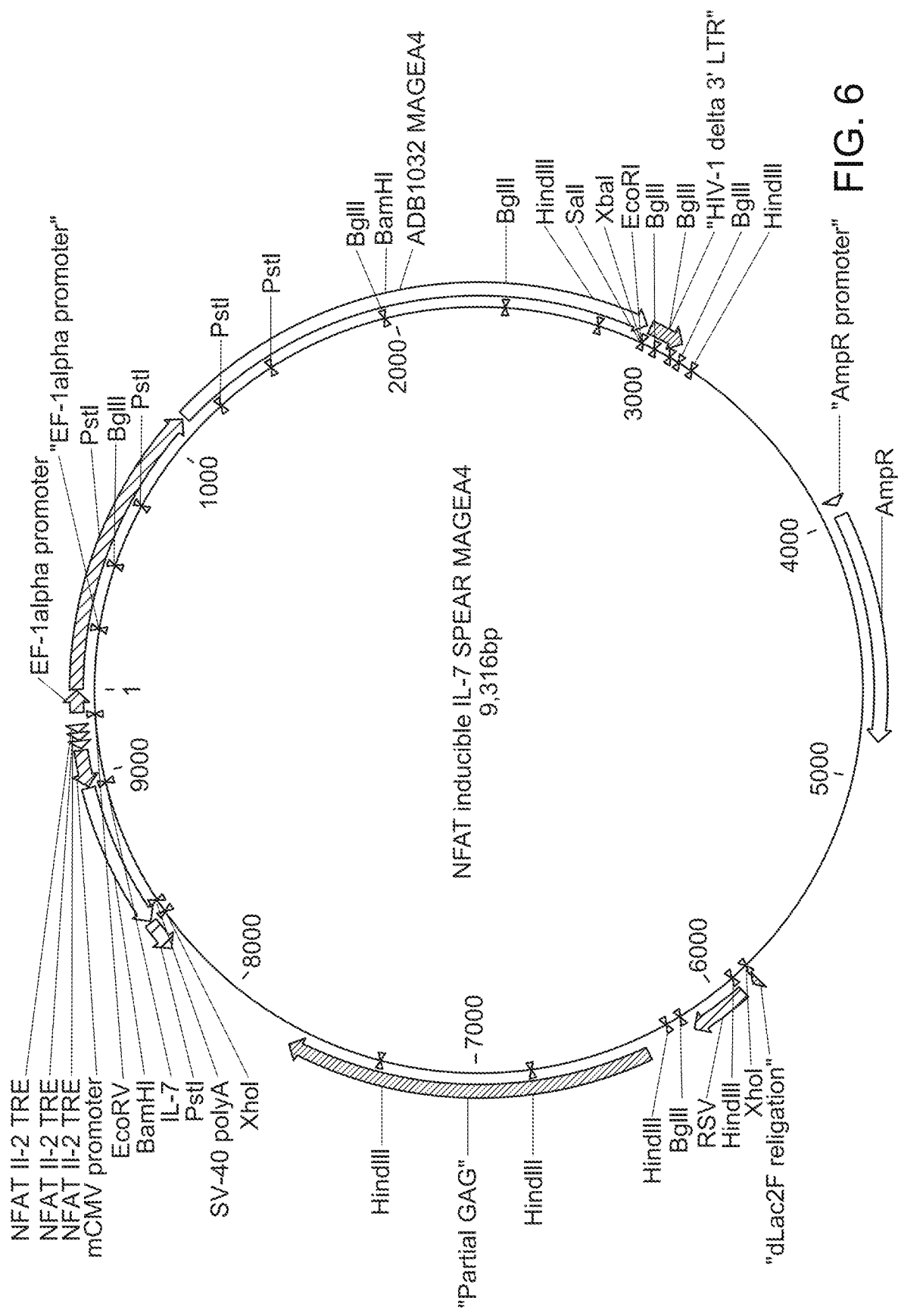
FIG. 6 shows a plasmid map for NFAT inducible IL-7 TCR2

Sense strand 5' to 3' sequence spanning the region between the Mlul and SalI restriction sites (see FIG. 6).

SEQ ID NO: 10

ACGCGTTAAGATACATTGATGAGTTTGGACAAACCACAACTAGAATGCAGTGAAAAAAATGCTTTATT
TGTGAAATTTGTGATGCTATTGCTTTATTTGTAACCATTATAAGCTGCAATAAACAAGTTCTCGAGTC
AGTGCTCTTTGGTGCCCATCAGGATCTTGTTCCAGCAGGTCTTGATTTCCTGCAGCAGCCGCTTCAGG
AAGCACAGGTCGTTCAGTTTCTTCTGCTCTTTCAGGGACTTGTTCTCTTCCAGGCTCTTGGTAGGCTG
GGCTTCTCCCAGGGCGGCAGGCTTTCTGCCCTTCACTTGGCCGGTGCAATTCAGCAGGATGGTGGTGC
CCTCGGACACTTTCAGCAGATGCAGGTCGAAGTCGCCGGTGCTGTTCATCTTCAGGAACTGCCGCAGC
TTTCTGGCGGCTCTGAACAGGAACATGCCTTCTTTGTTGGCGTCGCAGATGTGCCGCTTGAAGAAGTT
GAACTCGTTGTTCAGGCAGTTGCTGCCGATTTCCTTCATGCTGTCCAGCAGCTGGTCGATGGACACCA
TCAGCACGCTCTCGTACTGCTTGCCGTCCTTGCCCTCGATGTCGCAGTCGCTGCTGGCCACAGGCAGC
AGCACCAGGATCAGGGGGGGCAGGCCGAAGATGTACCGGAAGGACACGTGGAACATGGTGGCGGCCAT
ATGGATCCAACGAATGTCGAGAGGCTGGATCGGTCCCGGTGTCTTCTATGGAGGTCAAAACAGCGTGG
ATGGCGTCTCCAGGCGATCTGACGGTTCACTAAACGAGCTCTGCTTATATAGGCCTCCCACCGTACAC

-continued

Sequences:

GCCTAGACGTCACGCCTTCTGTATGAAACAGTTTTTCCTCCACGCCTTCTGTATGAAACAGTTTTTCC

TCCACGCCTTCTGTATGAAACAGTTTTTCCTCCGCTAGCGAGCTCAGGTACCGGCCAGTTAGGCCGAT

ATCATGCATCGTGAGGCTCCGGTGCCCGTCAGTGGGCAGAGCGCACATCGCCCACAGTCCCCGAGAAG

TTGGGGGAGGGGTCGGCAATTGAACCGGTGCCTAGAGAAGGTGGCGCGGGGTAAACTGGGAAAGTGA

TGTCGTGTACTGGCTCCGCCTTTTTCCCGAGGGTGGGGGAGAACCGTATATAAGTGCAGTAGTCGCCG

TGAACGTTCTTTTTCGCAACGGGTTTGCCGCCAGAACACAGGTAAGTGCCGTGTGTGGTTCCCGCGGG

CCTGGCCTCTTTACGGGTTATGGCCCTTGCGTGCCTTGAATTACTTCCACCTGGCTGCAGTACGTGAT

TCTTGATCCCGAGCTTCGGGTTGGAAGTGGGTGGGAGAGTTCGAGGCCTTGCGCTTAAGGAGCCCCTT

CGCCTCGTGCTTGAGTTGAGGCCTGGCCTGGGCGCTGGGGCCGCCGCGTGCGAATCTGGTGGCACCTT

CGCGCCTGTCTCGCTGCTTTCGATAAGTCTCTAGCCATTTAAAATTTTTGATGACCTGCTGCGACGCT

TTTTTTCTGGCAAGATAGTCTTGTAAATGCGGGCCAAGATCTGCACACTGGTATTTCGGTTTTTGGGG

CCGCGGGCGGCGACGGGGCCCGTGCGTCCCAGCGCACATGTTCGGCGAGGCGGGGCCTGCGAGCGCGG

CCACCGAGAATCGGACGGGGGTAGTCTCAAGCTGGCCGGCCTGCTCTGGTGCCTGGCCTCGCGCCGCC

GTGTATCGCCCCGCCCTGGGCGGCAAGGCTGGCCCGGTCGGCACCAGTTGCGTGAGCGGAAAGATGGC

CGCTTCCCGGCCCTGCTGCAGGGAGCTCAAAATGGAGGACGCGGCGCTCGGGAGAGCGGGCGGGTGAG

TCACCCACACAAAGGAAAAGGGCCTTTCCGTCCTCAGCCGTCGCTTCATGTGACTCCACTGAGTACCG

GGCGCCGTCCAGGCACCTCGATTAGTTCTCGTGCTTTTGGAGTACGTCGTCTTTAGGTTGGGGGAGG

GGTTTTATGCGATGGAGTTTCCCCACACTGAGTGGGTGGAGACTGAAGTTAGGCCAGCTTGGCACTTG

ATGTAATTCTCCTTGGAATTTGCCCTTTTTGAGTTTGGATCTTGGTTCATTCTCAAGCCTCAGACAGT

GGTTCAAAGTTTTTTTCTTCCATTTCAGGTGTCGTGAGCTAGCCGCCACCATGAAGAAGCACCTGACC

ACCTTTCTCGTGATCCTGTGGCTGTACTTCTACCGGGGCAACGGCAAGAACCAGGTGGAACAGAGCCC

CCAGAGCCTGATCATCCTGGAAGGCAAGAACTGCACCCTGCAGTGCAACTACACCGTGTCCCCCTTCA

GCAACCTGCGGTGGTACAAGCAGGACACCGGCAGAGGCCCTGTGTCCCTGACCATCCTGACCTTCAGC

GAGAACACCAAGAGCAACGGCCGGTACACCGCCACCCTGGACGCCGATACAAAGCAGAGCAGCCTGCA

CATCACCGCCAGCCAGCTGAGCGATAGCGCCAGCTACATCTGCGTGGTGTCCGGCGGCACAGACAGCT

GGGGCAAGCTGCAGTTTGGCGCCGGAACACAGGTGGTCGTGACCCCCGACATCCAGAACCCTGACCCT

GCCGTGTACCAGCTGCGGGACAGCAAGAGCAGCGACAAGAGCGTGTGCCTGTTCACCGACTTCGACAG

CCAGACCAACGTGTCCCAGAGCAAGGACAGCGACGTGTACATCACCGACAAGACCGTGCTGGACATGC

GGAGCATGGACTTCAAGAGCAATAGCGCCGTGGCCTGGTCCAACAAGAGCGACTTCGCCTGCGCCAAC

GCCTTCAACAACAGCATTATCCCCGAGGACACATTCTTCCCAAGCCCCGAGAGCAGCTGCGACGTCAA

GCTGGTGGAAAAGAGCTTCGAGACAGACACCAACCTGAACTTCCAGAACCTGAGCGTGATCGGCTTCA

GAATCCTGCTGCTGAAGGTGGCCGGCTTCAACCTGCTGATGACCCTGAGACTGTGGTCCAGCGGCAGC

CGGGCCAAGAGATCTGGATCCGGCGCTACCAACTTTAGCCTGCTGAAGCAGGCCGGGGACGTGGAAGA

AAACCCTGGCCCTAGGATGGCCAGCCTGCTGTTCTTCTGCGGCGCCTTCTACCTGCTGGGCACCGGCT

CTATGGATGCCGACGTGACCCAGACCCCCCGGAACAGAATCACCAAGACCGGCAAGCGGATCATGCTG

GAATGCTCCCAGACCAAGGGCCACGACCGGATGTACTGGTACAGACAGGACCCTGGCCTGGGCCTGCG

GCTGATCTACTACAGCTTCGACGTGAAGGACATCAACAAGGGCGAGATCAGCGACGGCTACAGCGTGT

CCAGACAGGCTCAGGCCAAGTTCAGCCTGTCCCTGGAAAGCGCCATCCCCAACCAGACCGCCCTGTAC

| Sequences: | |
|---|---|
| TTTTGTGCCACAAGCGGCCAGGGCGCCTACGAGGAGCAGTTCTTTTGGCCCTGGCACCCGGCTGACAGT GCTGGAAGATCTGAAGAACGTGTTCCCCCCAGAGGTGGCCGTGTTCGAGCCTTCTGAGGCCGAAATCA GCCACACCCAGAAAGCCACACTCGTGTGTCTGGCCACCGGCTTCTACCCCGACCACGTGGAACTGTCT TGGTGGGTCAACGGCAAAGAGGTGCACAGCGGCGTGTCCACCGATCCCCAGCCTCTGAAAGAACAGCC CGCCCTGAACGACAGCCGGTACTGCCTGAGCAGCAGACTGAGAGTGTCCGCCACCTTCTGGCAGAACC CCAGAAACCACTTCAGATGCCAGGTGCAGTTTTACGGCCTGAGCGAGAACGACGAGTGGACCCAGGAC AGAGCCAAGCCCGTGACACAGATCGTGTCTGCCGAAGCTTGGGGCGCGCCGATTGTGGCTTTACCAG CGAGAGCTACCAGCAGGGCGTGCTGAGCGCCACCATCCTGTACGAGATCCTGCTGGGAAAGGCCACAC TGTACGCCGTGCTGGTGTCTGCCCTGGTGCTGATGGCCATGGTCAAGCGGAAGGACAGCCGGGGCTAA TAAGTCGAC | |
| TCR2 sequence | SEQ ID NO: 11 |
| MKKHLTTFLVILWLYFYRGNGKNQVEQSPQSLIILEGKNCTLQCNYTVSPFSNLRWYKQDTGRGPVSL TILTFSENTKSNGRYTATLDADTKQSSLHITASQLSDSASYICVVSGGTDSWGKLQFGAGTQVVVTPD IQNPDPAVYQLRDSKSSDKSVCLFTDFDSQTNVSQSKDSDVYITDKTVLDMRSMDFKSNSAVAWSNKS DFACANAFNNSIIPEDTFFPSPESSCDVKLVEKSFETDTNLNFQNLSVIGFRILLLKVAGFNLLMTLR LWSSGSRAKRSGSGATNFSLLKQAGDVEENPGPRMASLLFFCGAFYLLGTGSMDADVTQTPRNRITKT GKRIMLECSQTKGHDRMYWYRQDPGLGLRLIYYSFDVKDINKGEISDGYSVSRQAQAKFSLSLESAIP NQTALYFCATSGQGAYEEQFFGPGTRLTVLEDLKNVFPPEVAVFEPSEAEISHTQKATLVCLATGFYP DHVELSWWVNGKEVHSGVSTDPQPLKEQPALNDSRYCLSSRLRVSATFWQNPRNHFRCQVQFYGLSEN DEWTQDRAKPVTQIVSAEAWGRADCGFTSESYQQGVLSATILYEILLGKATLYAVLVSALVLMAMVKR KDSRG | |
| Nucleotide sequence covering the region between the NheI and SalI restriction sites. | SEQ ID NO: 12 |
| GCTAGCGCCGCCACCATGTTCCACGTGTCCTTCCGGTACATCTTCGGCCTGCCCCCCCTGATCCTGGT GCTGCTGCCTGTGGCCAGCAGCGACTGCGACATCGAGGGCAAGGACGGCAAGCAGTACGAGAGCGTGC TGATGGTGTCCATCGACCAGCTGCTGGACAGCATGAAGGAAATCGGCAGCAACTGCCTGAACAACGAG TTCAACTTCTTCAAGCGGCACATCTGCGACGCCAACAAAGAAGGCATGTTCCTGTTCAGAGCCGCCAG AAAGCTGCGGCAGTTCCTGAAGATGAACAGCACCGGCGACTTCGACCTGCATCTGCTGAAAGTGTCCG AGGGCACCACCATCCTGCTGAATTGCACCGGCCAAGTGAAGGGCAGAAAGCCTGCCGCCCTGGGAGAA GCCCAGCCTACCAAGAGCCTGGAAGAGAACAAGTCCCTGAAAGAGCAGAAGAAACTGAACGACCTGTG CTTCCTGAAGCGGCTGCTGCAGGAAATCAAGACCTGCTGGAACAAGATCCTGATGGGCACCAAAGAGC ACGGAAGCAGAGCCAAGAGAAGCGGCTCTGGCGCGCCCGTGAAGCAGACCCTGAACTTCGACCTGCTG AAACTGGCCGGCGACGTGGAAAGCAACCCTGGCCCTATGAAGAAGCACCTGACCACCTTTCTCGTGAT CCTGTGGCTGTACTTCTACCGGGGCAACGGCAAGAACCAGGTGGAACAGAGCCCCCAGAGCCTGATCA TCCTGGAAGGCAAGAACTGCACTCTGCAGTGCAACTACACCGTGTCCCCCTTCAGCAACCTGCGCTGG TACAAGCAGGATACCGGCAGAGGCCCTGTGTCCCTGACCATCCTGACCTTCAGCGAGAACACCAAGAG CAACGGCCGGTACACCGCCACCCTGGACGCCGATACAAAGCAGAGCAGCCTGCACATCACCGCCTCCC AGCTGAGCGATAGCGCCAGCTACATCTGCGTGGTGTCCGGCGGCACAGACAGCTGGGGCAAGCTGCAG TTTGGCGCCGGAACACAGGTGGTCGTGACCCCCGACATCCAGAACCCTGACCCTGCCGTGTACCAGCT | |

| Sequences: |
|---|
| GCGGGACAGCAAGAGCAGCGACAAGAGCGTGTGCCTGTTCACCGACTTCGACTCCCAGACCAACGTGT |
| CCCAGAGCAAGGACAGCGACGTGTACATCACCGACAAGACCGTGCTGGATATGCGGAGCATGGACTTC |
| AAGAGCAATAGCGCCGTGGCCTGGTCTAACAAGAGCGACTTCGCCTGCGCCAACGCCTTCAACAACAG |
| CATTATCCCCGAGGACACATTCTTCCCAAGCCCCGAGAGCAGCTGCGACGTGAAACTGGTGGAAAAGA |
| GCTTCGAGACAGACACCAACCTGAATTTCCAGAACCTGAGCGTGATCGGCTTCCGGATCCTGCTGCTG |
| AAGGTGGCCGGATTCAACCTGCTGATGACCCTGCGGCTGTGGTCCTCTGGCTCTCGGGCCAAGAGAAG |
| CGGCAGCGGCGCCACCAATTTCAGCCTGCTGAAGCAGGCAGGGGATGTGGAAGAGAATCCCGGCCCTA |
| GAATGGCCTCCCTGCTGTTTTTCTGCGGCGCCTTCTACCTGCTGGGGACCGGCAGCATGGACGCTGAC |
| GTGACCCAGACCCCCCGGAACAGAATCACCAAGACCGGCAAGCGGATCATGCTGGAATGCAGCCAGAC |
| AAAGGGCCACGACCGGATGTACTGGTACAGACAGGATCCAGGACTGGGCCTGAGGCTGATCTACTACA |
| GCTTCGATGTGAAGGACATCAACAAGGGCGAGATCAGCGACGGCTACAGCGTGTCCAGACAGGCCCAG |
| GCCAAGTTCTCCCTGAGCCTGGAAAGCGCCATCCCCAACCAGACCGCCCTGTACTTTTGTGCCACAAG |
| CGGCCAGGGCGCCTACGAGGAACAGTTCTTTGGCCCTGGCACCCGGCTGACAGTGCTGGAAGATCTGA |
| AGAACGTGTTCCCCCCAGAGGTGGCAGTGTTCGAGCCTAGCGAGGCCGAGATCTCCCACACCCAGAAA |
| GCCACACTCGTGTGTCTGGCCACCGGATTCTACCCCGACCATGTGGAACTGTCTTGGTGGGTCAACGG |
| CAAAGAGGTGCACAGCGGCGTGTCCACCGATCCCCAGCCTCTGAAAGAACAGCCCGCCCTGAACGACA |
| GCCGGTACTGCCTGAGCAGCAGACTGAGAGTGTCCGCCACCTTCTGGCAGAACCCCAGAAATCACTTC |
| AGATGCCAGGTGCAGTTTTACGGCCTGAGCGAGAACGACGAGTGGACCCAGGATAGGGCCAAGCCCGT |
| GACTCAGATCGTGTCTGCCGAAGCCTGGGGCAGAGCCGATTGCGGCTTTACCAGCGAGAGCTACCAGC |
| AGGGCGTGCTGAGCGCCACCATCCTGTACGAGATCCTGCTGGGCAAGGCCACACTGTACGCCGTGCTG |
| GTGTCTGCCCTGGTGCTGATGGCCATGGTCAAGCGGAAGGACAGCCGGGCTGATGAGGTCGAC |

Translated protein sequence of constitutive IL-7_TCR2

SEQ ID NO: 13

MFHVSFRYIFGLPPLILVLLPVASSDCDIEGKDGKQYESVLMVSIDQLLDSMKEIGSNCLNNEFNFFK
RHICDANKEGMFLFRAARKLRQFLKMNSTGDFDLHLLKVSEGTTILLNCTGQVKGRKPAALGEAQPTK
SLEENKSLKEQKKLNDLCFLKRLLQEIKTCWNKILMGTKEHGSRAKRSGSGAPVKQTLNFDLLKLAGD
VESNPGPMKKHLTTFLVILWLYFRGNGKNQVEQSPQSLIILEGKNCTLQCNYTVSPFSNLRWYKQDT
GRGPVSLTILTFSENTKSNGRYTATLDADTKQSSLHITASQLSDSASYICVVSGGTDSWGKLQFGAGT
QVVVTPDIQNPDPAVYQLRDSKSSDKSVCLFTDFDSQTNVSQSKDSDVYITDKTVLDMRSMDFKSNSA
VAWSNKSDFACANAFNNSIIPEDTFFPSPESSCDVKLVEKSFETDTNLNFQNLSVIGFRILLLKVAGF
NLLMTLRLWSSGSRAKRSGSGATNFSLLKQAGDVEENPGPRMASLLFFCGAFYLLGTGSMDADVTQTP
RNRITKTGKRIMLECSQTKGHDRMYWYRQDPGLGLRLIYYSFDVKDINKGEISDGYSVSRQAQAKFSL
SLESAIPNQTALYFCATSGQGAYEEQFFGPGTRLTVLEDLKNVFPPEVAVFEPSEAEISHTQKATLVC
LATGFYPDHVELSWWVNGKEVHSGVSTDPQPLKEQPALNDSRYCLSSRLRVSATFWQNPRNHFRCQVQ
FYGLSENDEWTQDRAKPVTQIVSAEAWGRADCGFTSESYQQGVLSATILYEILLGKATLYAVLVSALV
LMAMVKRKDSRG**

| Sequences: | |
|---|---|
| human IL2 promoter NFAT TRE<br><br>GGAGGAAAAACTGTTTCATACAGAAGGCGT | SEQ ID NO: 14 |
| minimal CMV promoter<br><br>TAGGCGTGTACGGTGGGAGGCCTATATAAGCAGAGCTCGTTTAGTGAACCGTCAGATCGCCTGGAGAC<br><br>GCCATCCACGCTGTTTTGACCTCCATAGAAGACACCGGGACCGATCCAGCCTCTCGACATTCGTTGGA<br><br>TC | SEQ ID NO: 15 |

The invention claimed is:

1. A nucleic acid construct comprising:
   (i) a first nucleotide sequence encoding IL-7,
   (ii) a second nucleotide sequence encoding an antigen receptor, wherein the antigen receptor is a chimeric antigen receptor (CAR) that binds to a tumor antigen, or is a T cell receptor (TCR) that binds to an MHC-displayed peptide fragment of the tumor antigen;
   (iii) an inducible promoter operably linked to the first nucleotide sequence and
   (iv) a constitutive promoter operably linked to the second nucleotide.

2. The nucleic acid construct according to claim 1 wherein the expression from the inducible promoter is induced by the activation of T cells.

3. The nucleic acid construct according to claim 1 wherein the inducible promoter comprises a nuclear factor of activated T cells (NFAT) transcriptional response element (TRE).

4. The nucleic acid construct according to claim 3 wherein the NFAT TRE comprises the nucleic acid sequence of SEQ ID NO: 14 or a variant thereof.

5. The nucleic acid construct according to claim 3 wherein the inducible promoter comprises three or more copies of the NFAT TRE.

6. The nucleic acid construct according to claim 1 wherein the nucleic acid construct comprises the sequence of SEQ ID NO: 1.

7. The nucleic acid construct according to claim 1 wherein the constitutive promoter is the Human elongation factor-1 alpha promoter.

8. The nucleic acid construct according to claim 1 wherein the IL-7 is human IL-7.

9. The nucleic acid construct according to claim 1 wherein the antigen receptor is a T cell receptor (TCR).

10. The nucleic acid construct according to claim 9 wherein the TCR is an affinity enhanced TCR.

11. The nucleic acid construct according to claim 9 wherein the TCR comprises the amino acid sequence of any one of SEQ ID NOs: 5, 6 or 11.

12. The nucleic acid construct according to claim 1 wherein the antigen receptor is a chimeric antigen receptor (CAR).

13. The nucleic acid construct according to claim 12 wherein the tumor antigen is NY-ESO1, PRAME, alpha-fetoprotein (AFP), MAGE A4, MAGE A1, MAGE A10 or MAGE B2.

14. The nucleic acid construct according to claim 1 wherein the first nucleotide sequence is configured for expression in a first direction and the second nucleotide sequence is configured for expression in a first direction.

15. A vector comprising a nucleic acid construct according to claim 1.

16. A viral particle comprising a vector according to claim 15.

17. A population of T cells each comprising a nucleic construct-according to claim 1.

18. A pharmaceutical composition comprising a population of T cells according to claim 17 a pharmaceutically acceptable excipient.

19. The nucleic acid construct according to claim 10 wherein the tumor antigen is NY-ESO1, PRAME, alpha-fetoprotein (AFP), MAGE A4, MAGE A1, MAGE A10 or MAGE B2.

* * * * *